(12) United States Patent
Aboytes et al.

(10) Patent No.: US 12,053,182 B2
(45) Date of Patent: *Aug. 6, 2024

(54) DEVICES AND METHODS FOR THE TREATMENT OF VASCULAR DEFECTS

(71) Applicant: Covidien LP, Mansfield, MA (US)

(72) Inventors: Maria Aboytes, Palo Alto, CA (US); Arturo S. Rosqueta, San Jose, CA (US)

(73) Assignee: Covidien LP, Mansfield, MA (US)

( * ) Notice: Subject to any disclaimer, the term of this patent is extended or adjusted under 35 U.S.C. 154(b) by 665 days.

This patent is subject to a terminal disclaimer.

(21) Appl. No.: 17/247,765

(22) Filed: Dec. 22, 2020

(65) Prior Publication Data

US 2021/0244420 A1 Aug. 12, 2021

Related U.S. Application Data

(63) Continuation of application No. 16/156,536, filed on Oct. 10, 2018, now Pat. No. 10,939,916, which is a
(Continued)

(51) Int. Cl.
*A61B 17/12* (2006.01)
*A61B 17/00* (2006.01)
*A61M 29/00* (2006.01)

(52) U.S. Cl.
CPC .. *A61B 17/12113* (2013.01); *A61B 17/12163* (2013.01); *A61B 17/12168* (2013.01);
(Continued)

(58) Field of Classification Search
CPC ........ A61B 17/12031; A61B 17/12113; A61B 17/1214; A61B 17/12145;
(Continued)

(56) References Cited

U.S. PATENT DOCUMENTS 5,250,071 A 10/1993 Palermo
5,354,295 A 10/1994 Guglielmi et al.
(Continued)

FOREIGN PATENT DOCUMENTS

CA 2812012 A1 3/2012
CN 200991273 Y 12/2007
(Continued)

OTHER PUBLICATIONS

Extended European Search Report dated Jun. 17, 2020; European Application No. 19207991.1; 14 pages.
(Continued)

*Primary Examiner* — Robert A Lynch
(74) *Attorney, Agent, or Firm* — Fortem IP LLP

(57) ABSTRACT

Devices and methods for treating vascular defects, such as, for example, balloon-type aneurysms, are described herein. In one embodiment, an apparatus includes an insertion portion and an expandable implant. The expandable implant is configured to be deployed in an aneurysm and is coupled to the insertion portion. The expandable implant has a first portion and a second portion coupled to the first portion. The expandable implant is movable between a first configuration in which the first portion and the second portion are substantially linearly aligned and a second configuration in which the second portion at least partially overlaps the first portion.

20 Claims, 42 Drawing Sheets

Related U.S. Application Data continuation of application No. 16/147,883, filed on Oct. 1, 2018, now Pat. No. 10,898,200, which is a continuation of application No. 15/846,964, filed on Dec. 19, 2017, now Pat. No. 10,675,037, which is a continuation of application No. 15/162,073, filed on May 23, 2016, now Pat. No. 10,064,627, which is a continuation of application No. 14/661,233, filed on Mar. 18, 2015, now Pat. No. 9,855,051, which is a continuation of application No. 13/727,029, filed on Dec. 26, 2012, now Pat. No. 8,998,947, which is a continuation-in-part of application No. 13/421,122, filed on Mar. 15, 2012, now abandoned, which is a continuation-in-part of application No. 13/230,628, filed on Sep. 12, 2011, now Pat. No. 8,974,512.

(60) Provisional application No. 61/381,770, filed on Sep. 10, 2010.

(52) U.S. Cl.
CPC ....... *A61B 17/12172* (2013.01); *A61M 29/00* (2013.01); *H05K 999/99* (2013.01); *A61B 2017/00867* (2013.01); *A61B 2017/12054* (2013.01); *A61B 17/1214* (2013.01)

(58) Field of Classification Search
CPC ........ A61B 17/12163; A61B 17/12168; A61B 17/12172; A61B 2017/00867; A61B 2017/1205; A61B 2017/12054; A61M 29/00
See application file for complete search history.

(56) References Cited

U.S. PATENT DOCUMENTS

| | | |
|---|---|---|
| 5,645,558 A | 7/1997 | Horton |
| 5,669,931 A | 9/1997 | Kupiecki et al. |
| 5,725,552 A | 3/1998 | Kotula et al. |
| 5,733,294 A | 3/1998 | Forber et al. |
| 5,741,333 A | 4/1998 | Frid |
| 5,749,891 A | 5/1998 | Ken et al. |
| 5,749,919 A | 5/1998 | Blanc |
| 5,814,062 A | 9/1998 | Sepetka et al. |
| 5,911,731 A | 6/1999 | Pham et al. |
| 5,916,235 A | 6/1999 | Guglielmi |
| 5,925,060 A | 7/1999 | Forber |
| 5,928,260 A | 7/1999 | Chin et al. |
| 5,935,148 A | 8/1999 | Villar et al. |
| 5,944,738 A | 8/1999 | Amplatz et al. |
| 5,951,599 A | 9/1999 | McCrory |
| 5,964,797 A | 10/1999 | Ho |
| 5,976,169 A | 11/1999 | Imran |
| 5,980,554 A | 11/1999 | Lenker et al. |
| 6,022,374 A | 2/2000 | Imran |
| 6,033,423 A | 3/2000 | Ken et al. |
| 6,036,720 A | 3/2000 | Abrams et al. |
| 6,059,812 A | 5/2000 | Clerc et al. |
| 6,063,070 A | 5/2000 | Eder |
| 6,063,104 A | 5/2000 | Villar et al. |
| 6,086,577 A | 7/2000 | Ken et al. |
| 6,090,125 A | 7/2000 | Horton |
| 6,093,199 A | 7/2000 | Brown et al. |
| 6,096,021 A | 8/2000 | Helm et al. |
| 6,123,715 A | 9/2000 | Amplatz |
| 6,139,564 A | 10/2000 | Teoh |
| 6,152,144 A | 11/2000 | Lesh et al. |
| 6,159,531 A | 12/2000 | Dang et al. |
| 6,168,615 B1 | 1/2001 | Ken et al. |
| 6,168,622 B1 | 1/2001 | Mazzocchi |
| 6,309,367 B1 | 10/2001 | Boock |
| 6,344,048 B1 | 2/2002 | Chin et al. |
| 6,346,117 B1 | 2/2002 | Greenhalgh |
| 6,350,270 B1 | 2/2002 | Roue |
| 6,368,339 B1 | 4/2002 | Amplatz |
| 6,371,980 B1 | 4/2002 | Rudakov et al. |
| 6,375,668 B1 | 4/2002 | Gifford et al. |
| 6,383,174 B1 | 5/2002 | Eder |
| 6,391,037 B1 | 5/2002 | Greenhalgh |
| 6,428,558 B1 | 8/2002 | Jones et al. |
| 6,447,531 B1 | 9/2002 | Amplatz |
| 6,451,050 B1 | 9/2002 | Rudakov et al. |
| 6,454,780 B1 | 9/2002 | Wallace |
| 6,494,884 B2 | 12/2002 | Gifford et al. |
| 6,506,204 B2 | 1/2003 | Mazzocchi |
| 6,511,468 B1 | 1/2003 | Cragg et al. |
| 6,547,804 B2 | 4/2003 | Porter et al. |
| 6,551,303 B1 | 4/2003 | Van et al. |
| 6,579,303 B2 | 6/2003 | Amplatz |
| 6,585,748 B1 | 7/2003 | Jeffree |
| 6,589,256 B2 | 7/2003 | Forber |
| 6,589,265 B1 | 7/2003 | Palmer et al. |
| 6,599,308 B2 | 7/2003 | Amplatz |
| 6,602,261 B2 | 8/2003 | Greene et al. |
| 6,605,101 B1 | 8/2003 | Schaefer et al. |
| 6,605,102 B1 | 8/2003 | Mazzocchi et al. |
| 6,605,111 B2 | 8/2003 | Bose et al. |
| 6,613,074 B1 | 9/2003 | Mitelberg et al. |
| 6,626,939 B1 | 9/2003 | Burnside et al. |
| 6,635,068 B1 | 10/2003 | Dubrul et al. |
| 6,652,556 B1 | 11/2003 | Vantassel et al. |
| 6,666,882 B1 | 12/2003 | Bose et al. |
| 6,669,721 B1 | 12/2003 | Bose et al. |
| 6,682,546 B2 | 1/2004 | Amplatz |
| 6,689,486 B2 | 2/2004 | Ho et al. |
| 6,730,108 B2 | 5/2004 | Van et al. |
| 6,746,468 B1 | 6/2004 | Sepetka et al. |
| 6,746,890 B2 | 6/2004 | Gupta et al. |
| 6,780,196 B2 | 8/2004 | Chin et al. |
| 6,802,851 B2 | 10/2004 | Jones et al. |
| 6,811,560 B2 | 11/2004 | Jones et al. |
| 6,855,153 B2 | 2/2005 | Saadat |
| 6,855,154 B2 | 2/2005 | Abdel-Gawwad |
| 6,878,384 B2 | 4/2005 | Cruise et al. |
| 6,905,503 B2 | 6/2005 | Gifford et al. |
| 6,936,055 B1 | 8/2005 | Ken et al. |
| 6,991,617 B2 | 1/2006 | Hektner et al. |
| 6,994,092 B2 | 2/2006 | Van et al. |
| 6,994,717 B2 | 2/2006 | Konya et al. |
| 7,011,671 B2 | 3/2006 | Welch |
| 7,029,487 B2 | 4/2006 | Greene et al. |
| 7,083,632 B2 | 8/2006 | Avellanet et al. |
| 7,128,073 B1 | 10/2006 | Van et al. |
| 7,128,736 B1 | 10/2006 | Abrams et al. |
| 7,169,177 B2 | 1/2007 | Obara |
| 7,195,636 B2 | 3/2007 | Avellanet et al. |
| 7,229,461 B2 | 6/2007 | Chin et al. |
| 7,232,461 B2 | 6/2007 | Ramer |
| 7,326,225 B2 | 2/2008 | Ferrera et al. |
| 7,331,980 B2 | 2/2008 | Dubrul et al. |
| 7,419,503 B2 | 9/2008 | Pulnev et al. |
| 7,597,704 B2 | 10/2009 | Frazier et al. |
| 7,601,160 B2 | 10/2009 | Richter |
| 7,708,754 B2 | 5/2010 | Balgobin et al. |
| RE42,625 E | 8/2011 | Guglielmi |
| 8,043,326 B2 | 10/2011 | Hancock et al. |
| 8,142,456 B2 | 3/2012 | Rosqueta et al. |
| 8,211,160 B2 | 7/2012 | Garrison et al. |
| 8,333,783 B2 | 12/2012 | Braun et al. |
| 8,343,167 B2 | 1/2013 | Henson |
| 8,361,104 B2 | 1/2013 | Jones et al. |
| 8,361,138 B2 | 1/2013 | Adams |
| 8,425,541 B2 | 4/2013 | Masters et al. |
| 8,470,013 B2 | 6/2013 | Duggal et al. |
| 8,715,317 B1 | 5/2014 | Janardhan et al. |
| 8,834,515 B2 | 9/2014 | Win et al. |
| 8,906,057 B2 | 12/2014 | Connor et al. |
| 8,974,487 B2 * | 3/2015 | Connor ............ A61B 17/12022 606/198 |
| 8,974,512 B2 | 3/2015 | Aboytes et al. |
| 8,998,947 B2 | 4/2015 | Aboytes et al. |
| 9,211,202 B2 | 12/2015 | Strother et al. |

(56) References Cited

U.S. PATENT DOCUMENTS

| | | |
|---|---|---|
| 9,393,022 B2 * | 7/2016 | Becking .......... A61B 17/12159 |
| 9,486,224 B2 | 11/2016 | Riina et al. |
| 9,833,309 B2 | 12/2017 | Levi et al. |
| 9,844,380 B2 | 12/2017 | Furey |
| 9,844,382 B2 | 12/2017 | Aboytes et al. |
| 9,855,051 B2 | 1/2018 | Aboytes et al. |
| 9,907,684 B2 | 3/2018 | Connor et al. |
| 9,962,146 B2 | 5/2018 | Hebert et al. |
| 10,028,745 B2 | 7/2018 | Morsi |
| 10,617,426 B2 | 4/2020 | Aboytes et al. |
| 10,675,037 B2 * | 6/2020 | Aboytes .......... A61B 17/12172 |
| 10,939,916 B2 | 3/2021 | Aboytes et al. |
| 2001/0000797 A1 | 5/2001 | Mazzocchi |
| 2001/0001835 A1 | 5/2001 | Greene et al. |
| 2002/0062145 A1 | 5/2002 | Rudakov et al. |
| 2002/0169473 A1 | 11/2002 | Sepetka et al. |
| 2002/0193812 A1 | 12/2002 | Patel et al. |
| 2002/0193813 A1 | 12/2002 | Helkowski et al. |
| 2003/0004533 A1 | 1/2003 | Dieck et al. |
| 2003/0004568 A1 | 1/2003 | Ken et al. |
| 2003/0018294 A1 | 1/2003 | Cox |
| 2003/0028209 A1 | 2/2003 | Teoh et al. |
| 2003/0040772 A1 | 2/2003 | Hyodoh et al. |
| 2003/0055440 A1 | 3/2003 | Jones et al. |
| 2003/0093111 A1 | 5/2003 | Ken et al. |
| 2003/0113478 A1 | 6/2003 | Dang et al. |
| 2003/0114918 A1 | 6/2003 | Garrison et al. |
| 2004/0064093 A1 | 4/2004 | Hektner et al. |
| 2004/0115164 A1 | 6/2004 | Pierce et al. |
| 2004/0161451 A1 | 8/2004 | Pierce et al. |
| 2004/0172056 A1 | 9/2004 | Guterman et al. |
| 2005/0085836 A1 | 4/2005 | Raymond |
| 2005/0222580 A1 | 10/2005 | Gifford et al. |
| 2005/0267511 A1 | 12/2005 | Marks et al. |
| 2005/0277978 A1 | 12/2005 | Greenhalgh |
| 2006/0052816 A1 | 3/2006 | Bates et al. |
| 2006/0064151 A1 | 3/2006 | Guterman et al. |
| 2006/0089618 A1 | 4/2006 | McFerran et al. |
| 2006/0116709 A1 | 6/2006 | Sepetka et al. |
| 2006/0116712 A1 | 6/2006 | Sepetka et al. |
| 2006/0116713 A1 | 6/2006 | Sepetka et al. |
| 2006/0116714 A1 | 6/2006 | Sepetka et al. |
| 2006/0155323 A1 | 7/2006 | Porter et al. |
| 2006/0190025 A1 * | 8/2006 | Lehe .................. A61B 17/12109 606/200 |
| 2006/0190070 A1 | 8/2006 | Dieck et al. |
| 2006/0200234 A1 | 9/2006 | Hines |
| 2006/0206140 A1 | 9/2006 | Shaolian et al. |
| 2006/0206198 A1 | 9/2006 | Churchwell et al. |
| 2006/0206199 A1 | 9/2006 | Churchwell et al. |
| 2006/0241686 A1 | 10/2006 | Ferrera et al. |
| 2006/0247680 A1 | 11/2006 | Amplatz et al. |
| 2006/0271162 A1 | 11/2006 | Vito et al. |
| 2007/0010850 A1 | 1/2007 | Balgobin et al. |
| 2007/0083226 A1 | 4/2007 | Buiser et al. |
| 2007/0100426 A1 | 5/2007 | Rudakov et al. |
| 2007/0167876 A1 | 7/2007 | Euteneuer et al. |
| 2007/0167877 A1 | 7/2007 | Euteneuer et al. |
| 2007/0167972 A1 | 7/2007 | Euteneuer et al. |
| 2007/0175536 A1 | 8/2007 | Monetti et al. |
| 2007/0179520 A1 | 8/2007 | West |
| 2007/0185442 A1 | 8/2007 | Euteneuer et al. |
| 2007/0185443 A1 | 8/2007 | Euteneuer et al. |
| 2007/0185444 A1 | 8/2007 | Euteneuer et al. |
| 2007/0185457 A1 | 8/2007 | Euteneuer et al. |
| 2007/0191924 A1 | 8/2007 | Rudakov |
| 2007/0219619 A1 | 9/2007 | Dieck et al. |
| 2007/0265656 A1 * | 11/2007 | Amplatz .......... A61B 17/12122 606/200 |
| 2007/0276426 A1 | 11/2007 | Euteneuer |
| 2007/0276427 A1 | 11/2007 | Euteneuer |
| 2007/0282373 A1 | 12/2007 | Ashby et al. |
| 2007/0288083 A1 | 12/2007 | Hines |
| 2008/0082176 A1 | 4/2008 | Slazas |
| 2008/0114391 A1 | 5/2008 | Dieck et al. |
| 2008/0114436 A1 | 5/2008 | Dieck et al. |
| 2008/0200945 A1 | 8/2008 | Amplatz et al. |
| 2008/0200979 A1 | 8/2008 | Dieck et al. |
| 2008/0221600 A1 | 9/2008 | Dieck et al. |
| 2008/0281350 A1 * | 11/2008 | Sepetka .......... A61B 17/12172 606/200 |
| 2009/0043375 A1 | 2/2009 | Rudakov et al. |
| 2009/0062841 A1 | 3/2009 | Amplatz et al. |
| 2009/0062899 A1 | 3/2009 | Dang et al. |
| 2009/0112251 A1 * | 4/2009 | Qian .................. A61B 17/1215 606/194 |
| 2009/0187214 A1 | 7/2009 | Amplatz et al. |
| 2009/0264978 A1 | 10/2009 | Dieck et al. |
| 2009/0275974 A1 | 11/2009 | Marchand et al. |
| 2009/0287291 A1 | 11/2009 | Becking et al. |
| 2009/0287292 A1 | 11/2009 | Becking et al. |
| 2009/0287294 A1 * | 11/2009 | Rosqueta .......... A61B 17/12159 623/1.15 |
| 2009/0318892 A1 | 12/2009 | Aboytes et al. |
| 2009/0318941 A1 | 12/2009 | Sepetka et al. |
| 2009/0319023 A1 | 12/2009 | Hildebrand et al. |
| 2010/0030200 A1 | 2/2010 | Strauss et al. |
| 2010/0036410 A1 | 2/2010 | Krolik et al. |
| 2010/0139465 A1 | 6/2010 | Christian et al. |
| 2010/0144895 A1 | 6/2010 | Porter |
| 2010/0174269 A1 | 7/2010 | Tompkins et al. |
| 2010/0185271 A1 | 7/2010 | Zhang |
| 2010/0256527 A1 | 10/2010 | Lippert et al. |
| 2010/0256528 A1 | 10/2010 | Lippert et al. |
| 2010/0256601 A1 | 10/2010 | Lippert et al. |
| 2010/0256602 A1 | 10/2010 | Lippert et al. |
| 2010/0256603 A1 | 10/2010 | Lippert et al. |
| 2010/0256604 A1 | 10/2010 | Lippert et al. |
| 2010/0256605 A1 | 10/2010 | Lippert et al. |
| 2010/0256606 A1 | 10/2010 | Lippert et al. |
| 2010/0262014 A1 | 10/2010 | Huang |
| 2010/0268201 A1 | 10/2010 | Tieu et al. |
| 2011/0022149 A1 | 1/2011 | Cox et al. |
| 2011/0046658 A1 | 2/2011 | Connor et al. |
| 2011/0077620 A1 | 3/2011 | Debeer |
| 2011/0137332 A1 | 6/2011 | Sepetka et al. |
| 2011/0137405 A1 | 6/2011 | Wilson et al. |
| 2011/0144669 A1 | 6/2011 | Becking et al. |
| 2011/0152993 A1 | 6/2011 | Marchand et al. |
| 2011/0202085 A1 * | 8/2011 | Loganathan ...... A61B 17/12113 606/200 |
| 2011/0208227 A1 | 8/2011 | Becking |
| 2011/0224776 A1 | 9/2011 | Sepetka et al. |
| 2011/0265943 A1 | 11/2011 | Rosqueta et al. |
| 2011/0319926 A1 | 12/2011 | Becking et al. |
| 2012/0022572 A1 | 1/2012 | Braun et al. |
| 2012/0041472 A1 | 2/2012 | Tan et al. |
| 2012/0101510 A1 | 4/2012 | Lenker et al. |
| 2012/0116350 A1 | 5/2012 | Strauss et al. |
| 2012/0165919 A1 | 6/2012 | Cox et al. |
| 2012/0197283 A1 | 8/2012 | Marchand et al. |
| 2012/0239074 A1 | 9/2012 | Aboytes et al. |
| 2012/0283769 A1 | 11/2012 | Cruise et al. |
| 2012/0316598 A1 | 12/2012 | Becking et al. |
| 2012/0316632 A1 | 12/2012 | Gao |
| 2012/0330341 A1 | 12/2012 | Becking et al. |
| 2012/0330347 A1 | 12/2012 | Becking et al. |
| 2012/0330348 A1 | 12/2012 | Strauss et al. |
| 2013/0066357 A1 | 3/2013 | Aboytes et al. |
| 2013/0066360 A1 | 3/2013 | Becking et al. |
| 2013/0085522 A1 | 4/2013 | Becking et al. |
| 2013/0116722 A1 | 5/2013 | Aboytes et al. |
| 2013/0274866 A1 | 10/2013 | Cox et al. |
| 2014/0012307 A1 | 1/2014 | Franano et al. |
| 2014/0058420 A1 | 2/2014 | Hannes et al. |
| 2014/0316012 A1 | 10/2014 | Freyman et al. |
| 2014/0371734 A1 | 12/2014 | Truckai |
| 2015/0216684 A1 | 8/2015 | Enzmann et al. |
| 2015/0250628 A1 | 9/2015 | Monstadt et al. |
| 2015/0272590 A1 | 10/2015 | Aboytes et al. |
| 2015/0313737 A1 | 11/2015 | Tippett et al. |
| 2015/0327843 A1 | 11/2015 | Garrison |
| 2015/0342613 A1 | 12/2015 | Aboytes et al. |
| 2016/0066921 A1 | 3/2016 | Seifert et al. |

(56) References Cited

U.S. PATENT DOCUMENTS

| | | |
|---|---|---|
| 2016/0135984 A1 | 5/2016 | Rudakov et al. |
| 2016/0206320 A1 | 7/2016 | Connor |
| 2016/0206321 A1 | 7/2016 | Connor |
| 2016/0262766 A1 | 9/2016 | Aboytes et al. |
| 2017/0150971 A1 | 6/2017 | Hines |
| 2017/0156903 A1 | 6/2017 | Shobayashi |
| 2017/0189035 A1 | 7/2017 | Porter |
| 2017/0266023 A1 | 9/2017 | Thomas |
| 2017/0340333 A1 | 11/2017 | Badruddin et al. |
| 2017/0367708 A1 | 12/2017 | Mayer et al. |
| 2018/0036012 A1 | 2/2018 | Aboytes et al. |
| 2018/0049859 A1 | 2/2018 | Stoppenhagen et al. |
| 2018/0125686 A1 | 5/2018 | Lu |
| 2018/0140305 A1 | 5/2018 | Connor |
| 2018/0161185 A1 | 6/2018 | Kresslein et al. |
| 2018/0193025 A1 | 7/2018 | Walzman |
| 2018/0193026 A1 | 7/2018 | Yang et al. |
| 2018/0206852 A1 | 7/2018 | Moeller |
| 2019/0053811 A1 | 2/2019 | Garza et al. |
| 2021/0378681 A1 | 12/2021 | Aboytes et al. |

FOREIGN PATENT DOCUMENTS

| | | |
|---|---|---|
| DE | 102011102933 A1 | 12/2012 |
| EP | 0717969 A2 | 6/1996 |
| EP | 1295563 A1 | 3/2003 |
| EP | 1813213 A2 | 8/2007 |
| EP | 2208483 A1 | 7/2010 |
| EP | 2609888 A1 | 7/2013 |
| FR | 2890306 A1 | 3/2007 |
| JP | H06319743 A | 11/1994 |
| JP | 2005261951 A | 9/2005 |
| JP | 2008521492 A | 6/2008 |
| JP | 2010523260 A | 7/2010 |
| JP | 2018149392 A | 9/2018 |
| WO | 9406502 A2 | 3/1994 |
| WO | 9409705 A1 | 5/1994 |
| WO | 9907294 A1 | 2/1999 |
| WO | 9929260 A1 | 6/1999 |
| WO | 0164112 A1 | 9/2001 |
| WO | 02054980 A2 | 7/2002 |
| WO | 02089863 A1 | 11/2002 |
| WO | 2005099634 A1 | 10/2005 |
| WO | 2006034149 A2 | 3/2006 |
| WO | 2007121405 A2 | 10/2007 |
| WO | 2008036156 A1 | 3/2008 |
| WO | 2008074027 A1 | 6/2008 |
| WO | 2009014528 A1 | 1/2009 |
| WO | 2010009019 A1 | 1/2010 |
| WO | 2010027363 A1 | 3/2010 |
| WO | 2010077599 A1 | 7/2010 |
| WO | 2011066962 A1 | 6/2011 |
| WO | 2011095966 A1 | 8/2011 |
| WO | 2012034135 A1 | 3/2012 |
| WO | 2013112944 A1 | 8/2013 |
| WO | 2013138615 A2 | 9/2013 |
| WO | 2014105932 A1 | 7/2014 |
| WO | 2013138615 A3 | 9/2014 |
| WO | 2017074411 A1 | 5/2017 |
| WO | 2018051187 A1 | 3/2018 |

OTHER PUBLICATIONS

Extended European Search Report dated Sep. 19, 2019; European Patent Application No. 19183387.0; 6 pages.
Extended European Search Report dated Jul. 1, 2016 in European Patent Application No. 13867906.3; 9 pages.
Extended European Search Report dated Mar. 2, 2016 in European Patent Application No. 137616710.0; 13 pages.
Extended European Search Report dated Jan. 30, 2017 in European Patent Application No. 16190494.1; 9 pages.
Extended European Search Report dated Jan. 7, 2015 in European Patent Application No. 11824250.2, 7 pages.
International Search Report and Written Opinion for International Application No. PCT/US2013/077767, dated Mar. 19, 2014, 9 pages.
International Search Report and Written Opinion for International Application No. PCT/US2013/031466, dated Jun. 25, 2014, 11 pages.
International Search Report and Written Opinion for International Application No. PCT/US11/51268, dated Jan. 2, 2012, 10 pages.
Prosecution History for U.S. Appl. No. 13/230,628.
Prosecution History for U.S. Appl. No. 14/603,998.
Prosecution History for U.S. Appl. No. 14/693,417.
Prosecution History for U.S. Appl. No. 15/831,974.
Prosecution History for U.S. Appl. No. 15/832,394.
Prosecution History for U.S. Appl. No. 13/421,122.
Prosecution History for U.S. Appl. No. 14/661,233.
Prosecution History for U.S. Appl. No. 15/162,073.
Prosecution History for U.S. Appl. No. 15/228,278.
Prosecution History for U.S. Appl. No. 15/683,627.
Prosecution History for U.S. Appl. No. 16/147,883.

* cited by examiner

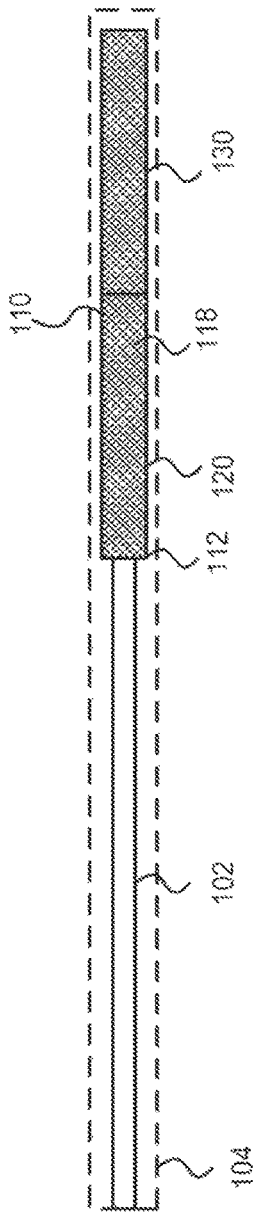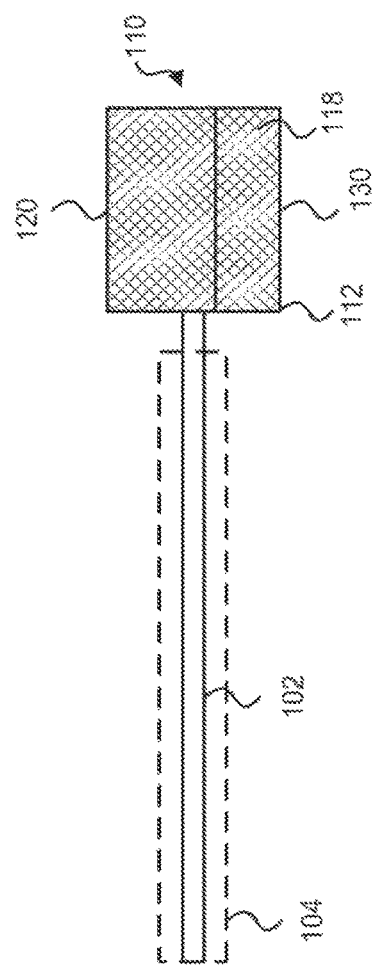

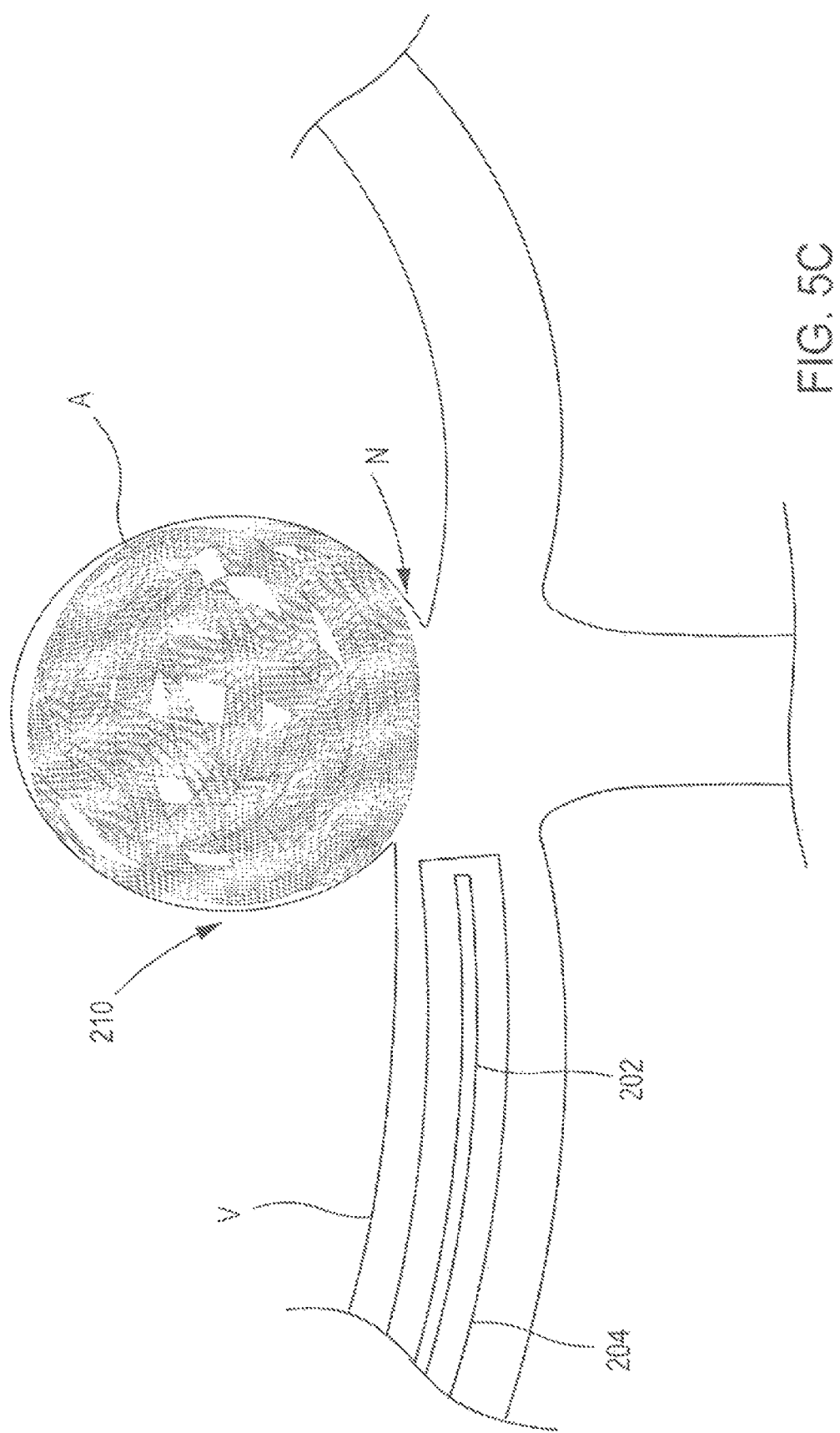

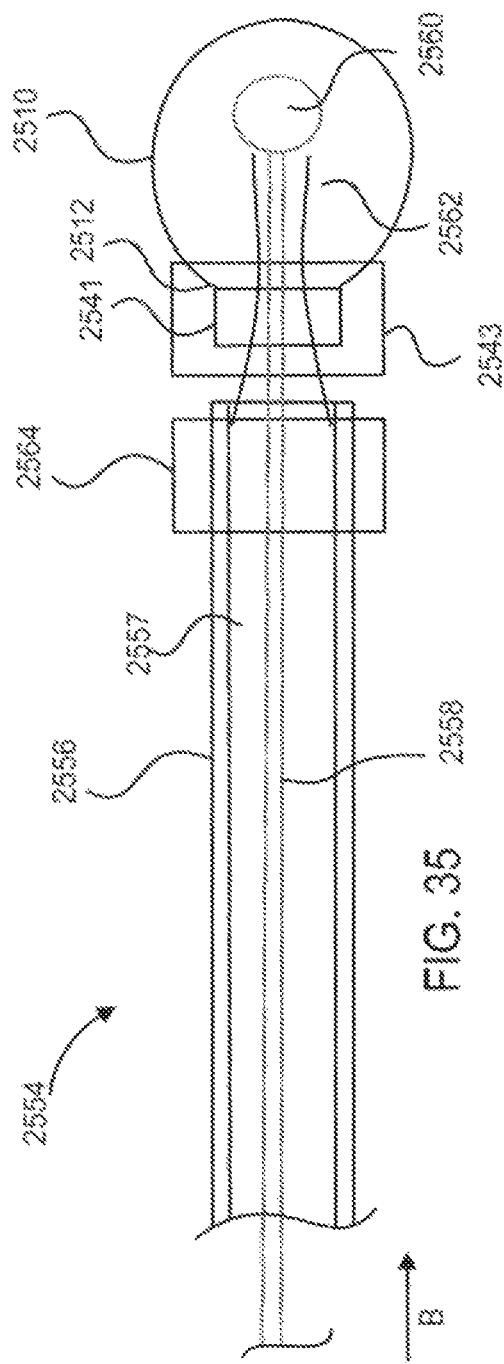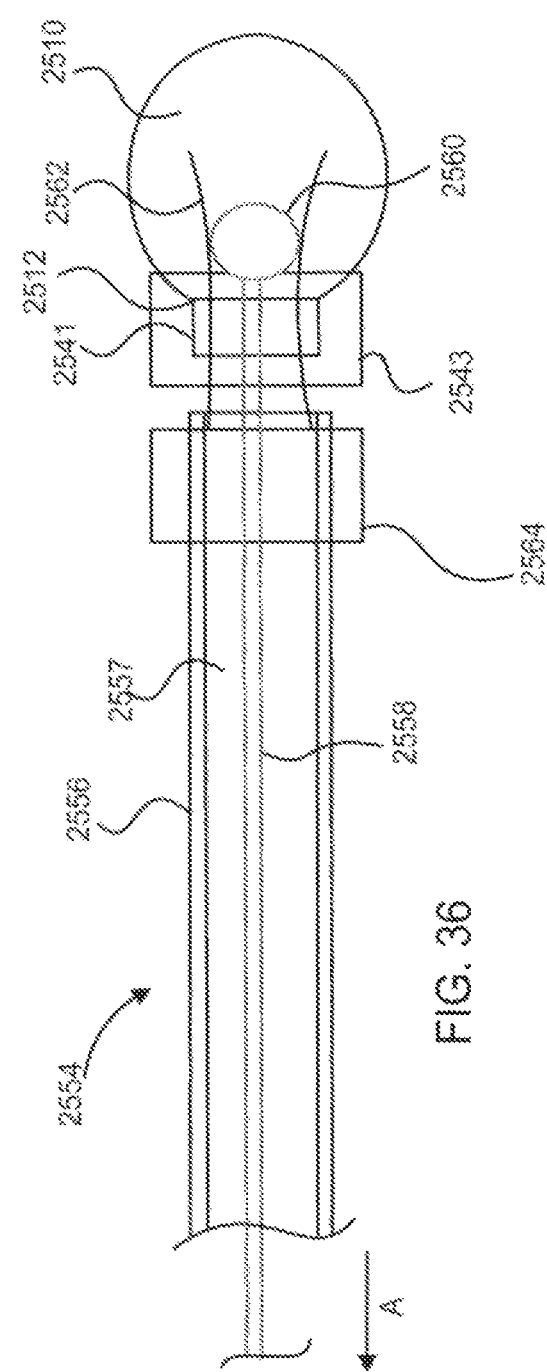

DEVICES AND METHODS FOR THE TREATMENT OF VASCULAR DEFECTS

CROSS-REFERENCE TO RELATED APPLICATIONS

This application is a continuation of U.S. patent application Ser. No. 16/156,536, filed Oct. 10, 2018, which is a continuation of U.S. patent application Ser. No. 16/147,883, filed Oct. 1, 2018, which is a continuation of U.S. patent application Ser. No. 15/846,964, filed Dec. 19, 2017, now U.S. Pat. No. 10,675,037, which is a continuation of U.S. patent application Ser. No. 15/162,073, filed May 23, 2016, now U.S. Pat. No. 10,064,627, which is continuation of U.S. patent application Ser. No. 14/661,233, filed Mar. 18, 2015, now U.S. Pat. No. 9,855,051, both of which are continuations of U.S. patent application Ser. No. 13/727,029, filed Dec. 26, 2012, now U.S. Pat. No. 8,998,947, which is a continuation-in-part of U.S. patent application Ser. No. 13/421,122, filed Mar. 15, 2012, now abandoned, which is a continuation-in-part of U.S. patent application Ser. No. 13/230,628, filed Sep. 12, 2011, now U.S. Pat. No. 8,974,512, which claims priority to and the benefit of U.S. Provisional Patent Application No. 61/381,770, filed Sep. 10, 2010. All of the foregoing disclosures are hereby incorporated by reference herein in their entireties.

BACKGROUND

The invention relates generally to medical devices and more particularly to expandable medical devices and methods for treating vascular defects. For example, the invention can relate to expandable medical devices and methods for treating an aneurysm. Aneurysms are dilations in a blood vessel caused from weakening of a blood vessel wall. The dilation is produced by the pressure exerted by normal blood flow, which can cause the weakened segment of the blood vessel to swell. In some cases, this swelling results in a sac, or balloon-like polyp protruding from the main or parent vessel. Continued growth and/or eventual rupture of the ballooned arterial wall can have devastating results for a patient. As such, unruptured aneurysms should be treated to prevent hemorrhage. Additionally, ruptured aneurysms can be treated to avert a subsequent rupture and/or additional damage.

Some known medical devices and treatment methods used for treating an aneurysm include delivering a platinum coil to the sac of the aneurysm. The platinum coil is electrolytically separated from a delivery wire, thus inducing a charge in the coil which can cause a thrombotic effect in the aneurysm. In known procedures, about 30% of the volume of the aneurysm is packed with coils. Such known devices and methods, however, often have an about 30% recanalization rate, meaning blood flow returns to the aneurysm again and can cause the coil-packed aneurysm to swell further. Additionally, such known devices and methods require prolonged procedure times for the patient and correspondingly increased exposure to radiation for the patient. Moreover, such devices and methods do not treat the neck of the aneurysm, which is the area between the parent blood vessel and the sac of the aneurysm.

Another known treatment method includes the use of both a coil and a stent. The coil is delivered to the sac of the aneurysm as described above, and the stent is positioned within the parent blood vessel such that a portion of the stent is disposed over the neck of the aneurysm. Such procedures have several drawbacks. For one, delivery of two separate types of devices (i.e., coil(s) and a stent) is a more complex procedure, often resulting in a longer procedure time for the patient. The stent may lead to intra-stent stenosis of the blood vessel. Additionally, a patient would likely be required to take a blood thinner indefinitely following the procedure. Moreover, such devices and methods are not suitable for treatment of aneurysms positioned at a bifurcation of the blood vessel (i.e., between adjacent branches of a vessel).

Another known device and treatment method includes the use of a flow diverter delivered to the parent blood vessel adjacent the neck of the aneurysm. Generally, the flow diverter is positioned within the parent blood vessel over the neck of the aneurysm to prevent additional blood flow into the aneurysm from the vessel. In current procedures, more than one flow diverter is required per aneurysm to ensure blood flow is appropriately diverted from the aneurysm. Such a device and treatment method has similar drawbacks to the use of a stent, described above. Specifically, the flow diverter may lead to stenosis of the blood vessel and the patient would likely be required to take a blood thinner indefinitely following the procedure. Additionally, known flow diverters are not suitable for treating an aneurysm positioned at a bifurcation of the blood vessel. Moreover, long term follow-up of patients treated using a flow diverter is showing an increased rate of recanalization to the aneurysm.

Thus, there is a need for improved systems, devices and methods for treating vascular defects, such as balloon-type aneurysms, as described herein.

SUMMARY

Devices and methods for treating vascular defects, such as, for example, balloon-type aneurysms, are described herein. In one embodiment, an apparatus includes an insertion portion and an expandable implant. The expandable implant is configured to be deployed in an aneurysm and is coupled to the insertion portion. The expandable implant has a first portion and a second portion coupled to the first portion. The expandable implant is movable between a first configuration in which the first portion and the second portion are substantially linearly aligned and a second configuration in which the second portion at least partially overlaps the first portion.

BRIEF DESCRIPTION OF THE DRAWINGS

FIG. 1 is a schematic illustration of a medical device according to an embodiment in a first configuration.

FIG. 2 is a schematic illustration of a medical device according to an embodiment in a second configuration.

FIG. 5C is a view of the medical device of FIG. 3 in a third configuration during insertion into an aneurysm.

FIG. 35 is a schematic illustration of a portion of an insertion device, according to an embodiment, shown in a first configuration and coupled to a schematic illustration of a portion of an expandable implant.

FIG. 36 is a schematic illustration of the portion of the insertion device and expandable implant of FIG. 35, shown in a second configuration.

DETAILED DESCRIPTION

Figure 3:
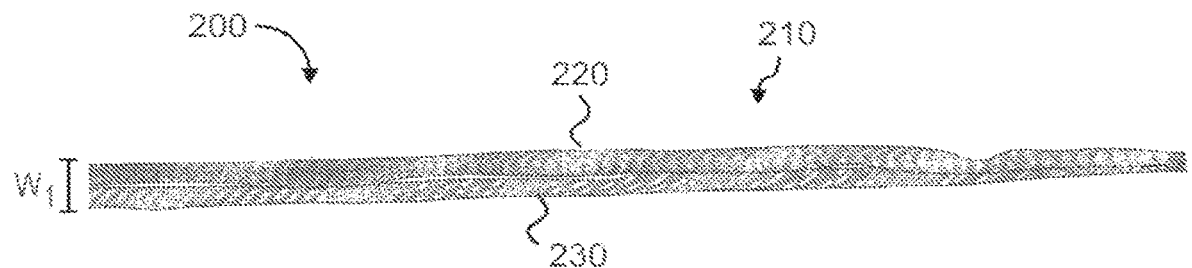
FIG. 3 is a side view of a medical device according to an embodiment in a first configuration.

Medical devices and methods of treatment are described herein to treat patients experiencing a vascular defect, such as an aneurysm, in a circulatory blood vessel and the effects of that defect, including hemorrhagic stroke. For example, the devices and methods described herein can be useful for treating vascular defects present in vasculature that is tortuous, of small-diameter, and/or that is otherwise difficult to access. More specifically, the devices and methods described herein can be useful for treating saccular (also referred to as balloon-type or berry) aneurysms, bifurcation aneurysms, fistulas, and other defects in vasculature, including defects in neurovasculature. The medical devices and methods of treatment described herein can reduce hemorrhagic events while promoting endothelialization of an opening between an aneurysm and a parent blood vessel from which the aneurysm bulge formed (e.g., at a neck of the aneurysm).

Various embodiments of a medical device for occupying all or substantially all of the volume of an aneurysm and/or promoting endothelialization at or proximate to the aneurysm are described herein. In some embodiments, the medical device includes an expandable implant including an electropositive woven or braided material. The filaments or strands forming the braid or weave are configured to encourage recruitment and/or retention of endothelial cells to the device and therefore within the defect. The expandable implant is configured to assume a non-linear predetermined three-dimensional shape within a sac of the aneurysm upon release from a tubular or other delivery constraint (e.g., a catheter or cannula). The electropositive woven or braided material has a particular porosity and includes multiple openings between the filaments or strands when the expandable implant is in the expanded configuration. Such openings are ideal in the blood environment for harboring endothelial cells recruited to the site. The electropositivity of the material encourages endothelialization in the presence of the electronegative charges of the blood and body tissues. Said another way, the electropositivity of the expandable implant in relation to a charge of blood and tissue (which is electronegative in comparison) provides an environment in the defect that promotes endothelialization. Endothelialization within the defect can ultimately result in the defect walling-off from the parent vessel. For example, the growth and development of an endothelial layer over a neck of an aneurysm can wall off the aneurysm from the parent vessel and allow flow dynamics to equilibrate at the defect. As such, the device can be configured to facilitate healing the defect and preventing recanalization because tissue is created from within the body that resists aberrant blood flow and redistributes the flow pressure that may have created the defect. Upon healing with endothelialization, the pressure is evenly distributed along the parent vessel in a manner that precludes recanalization at the defect post-treatment. Furthermore, blood from within the parent vessel no longer has access to the walled off defect once the endothelialization process is complete. Additionally, at least a portion of the expandable implant can be positioned over the neck of the aneurysm once the implant is deployed within the aneurysm such that the portion disrupts the flow of blood from the parent vessel into the aneurysm. As such, the expandable implant provides blood flow disruption in advance of and in addition to growth and development of the endothelial layer over the neck of the aneurysm.

A medical device described herein can include an insertion portion (e.g., a guide wire) and an expandable implant formed with, for example, woven or braided filaments in a mesh-like configuration. The terms mesh and braid can each refer herein to a fabric or material of woven or braided filaments or strands of wire or polymer. The expandable implant of the medical device can be configured to compress or collapse for delivery into a blood vessel. In some embodiments, the medical device can be inserted while in a collapsed or compressed configuration through a delivery device, such as, for example, a microcatheter, cannula, delivery tube or sheath. In some embodiments, the medical device can be deployed without the use of such a delivery device.

The expandable implant of the medical device can have a collapsed or compressed configuration such that the expandable implant has a diameter that can fit within the narrow constraints of the neurovasculature and/or within a lumen of a delivery catheter. The expandable implant of the medical device can be formed with, for example, an arrangement of strands (e.g., a mesh or braid arrangement of strands or filaments) that can compress and expand. Such materials include Nitinol, MP35N, stainless steel, cobalt chromium, titanium, platinum, tantalum, tungsten, or alloys thereof, or polyester, polyethylene (PET), Dacron, PEEK, vectron, and suture materials, and are available from Fort Wayne Metals of Fort Wayne, Ind., California Fine Wire Company of Grover Beach, Calif., other metal manufacturers, Ethicon Inc. of Somerville, N.J., Genzyme of Cambridge, Mass., Poly-Med, Inc. of Anderson, S.C., and/or other medical grade suture and fiber manufacturers. The expandable implant can be compressed over and/or along the insertion portion of the medical device. The insertion portion can be, for example, a wire. In some embodiments, a medical device includes an insertion portion movably disposable within a lumen of a delivery device. A distal portion of the insertion portion can be coupled to the expandable implant. The expandable implant can be moved from a collapsed configuration to an expanded configuration while disposed within, or as it is being inserted into, a defect (e.g., an aneurysm).

In some embodiments, the expandable implant can be formed with filaments of superelastic or shape memory material (such as, e.g., nitinol) and the braid or mesh can be set in a predefined shape prior to attaching the expandable implant to the insertion portion of the medical device. In such an embodiment, when the expandable implant is deployed and expands, it assumes a biased predetermined shape. The predetermined shape can be a generic shape, such as that of a sphere, or can be a custom-made shape based on a shape of a target aneurysm within a patient. Suitable materials are described in more detail herein.

The medical devices described herein can include one or more expandable implants formed with a woven mesh or braid that has variably sized apertures (also referred to herein as "openings" or "pores"). Said another way, the devices are formed with a material that has a particular porosity or pore density. In some embodiments, an expandable implant can have sections of mesh or braid having variation in density of the filaments and may include portions or bands of densely spaced filaments (i.e., lower porosity) spaced by portions or bands that are less dense (i.e., higher porosity). The less dense braid portion can have larger openings in the braid, while the more dense braid portion can have smaller openings in the braid. Material (e.g., bodily tissue such as endothelial cells) can be encouraged to enter and/or attach to interstices of the mesh of the expandable implant. For example, the more dense braid portion can be used to encourage greater endothelial cell attachment and the less dense braid portion can be used to reduce the overall weight and or material to be implanted in the patient. The less dense sections can also direct the final shape of the expandable implant. For example, sections of less dense (more open) mesh or braid can direct the effects of expansion of the implant.

In some embodiments, a medical device can be delivered to a desired treatment site within a vasculature by inserting the medical device through a lumen of a delivery catheter (e.g., a microcatheter). The expandable medical device can be inserted through the delivery catheter in a collapsed or compressed configuration. The expandable implant of the expandable medical device can be moved out through a distal end of the delivery catheter at the treatment site (e.g., into a sac of an aneurysm) and moved to an expanded configuration. In some embodiments, the delivery catheter is used to compress or collapse the expandable implant. For example, the expandable implant can be formed with a biased expanded configuration and when it is placed within a lumen of a catheter it is compressed. When the expandable implant is moved outside of the catheter, it can assume its biased expanded configuration. In the expanded configuration, a first portion of the expandable implant substantially overlaps a second portion of the expandable implant. The first and second portions of the expandable implant can be discrete structures or can be portions of a unitary or monolithically constructed device.

A medical device, such as an expandable implant, described herein can include a first porous member and a second porous member coupled to the first porous member. Each of the first and second porous members includes a first end and a second end. The first and second porous members each have a collapsed configuration for insertion through a blood vessel and an expanded configuration for occupying at least a portion of the volume defined by the sac of an aneurysm. In some embodiments, the first porous member is substantially elongate and has a greater width in its expanded configuration than in its collapsed configuration. The second porous member is substantially elongate and has a greater width in its expanded configuration than in its collapsed configuration. In some embodiments, the width of the first porous member is greater than the width of the second porous member, for example, when each of the first and second porous members are in their expanded configurations.

In some embodiments, the first porous member is configured to occupy a first volume in its collapsed configuration and a second, greater, volume in its expanded configuration. For example, the first porous member can have a substantially spherical, oblong, or other suitable shape in its expanded configuration that occupies a greater volume than the substantially elongate shape of the first porous member in its collapsed configuration. The second porous member can be configured to move or curve into a three dimensional configuration in the expanded configuration such that a first segment of the second porous member overlaps with a second segment of the second porous member. In its expanded configuration, the second porous member can define an interior region configured to receive the first porous member in its expanded configuration. For example, in some embodiments, the second porous member has a substantially spherical shape with an open interior region configured to receive the first porous member.

In some embodiments, a medical device, such as an expandable implant, described herein can include a first porous member and a second porous member. Each of the first and second porous members includes a first end and a second end. The first and second porous members each have a collapsed configuration for insertion through a blood vessel and an expanded configuration for occupying at least a portion of the volume defined by a sac of an aneurysm. The first and second porous members are each substantially elongate in the collapsed configuration. In its expanded configuration, the first porous member has a three-dimensional shape including a first segment configured to overlap with a second segment and defining an interior region. The second porous member is configured to be disposed in the interior region of the first porous member when each of the first and second porous members is in their respective expanded configurations. In some embodiments, the second porous member can be formed integrally or monolithically with the first porous member. In some embodiments, the second porous member can be woven or braided using the same filaments that form the first porous member.

In some embodiments, the expandable implant is in the form of a braided tube that includes fibers of a superelastic shape memory alloy, or polymeric fibers. In some embodiments, the expandable implant can effect a shape deformation inducing a substantially spherical contour. In some embodiments, the expandable implant can effect a shape deformation inducing a helical contour. In some embodiments, the shape deformation can include inducing radial expansion and/or axial shortening.

The medical devices described herein can be used to occupy at least a portion of the volume defined by a sac of an aneurysm and/or to promote endothelialization of the neck of the aneurysm to inhibit or stop blood flow into the aneurysm, which can lead to, for example, hemorrhagic stroke. In some embodiments, wire or polymer filaments can be used to form a woven mesh or braided strands that can be expandable, and have apertures sized to promote endothelial cell attachment at the aneurysm.

It is noted that, as used in this written description and the appended claims, the singular forms "a," "an" and "the" include plural referents unless the context clearly dictates otherwise. Thus, for example, the term "a lumen" is intended to mean a single lumen or a combination of lumens. Furthermore, the words "proximal" and "distal" refer to direction closer to and away from, respectively, an operator (e.g., surgeon, physician, nurse, technician, etc.) who would insert the medical device into the patient, with the tip-end (i.e., distal end) of the device inserted first inside a patient's body. Thus, for example, the end first inserted inside a patient's body would be the distal end of the medical device, while the end outside of or inserted later into a patient's body would be the proximal end of the medical device. Additionally, the terms "first," "second," "third," and so on, used to describe similarly identified elements are for purposes of clarity only, and are not meant to imply a priority or that such numerical identifier must be associated with that particular element in the claims.

FIGS. 1 and 2 are schematic illustrations of a vascular medical device 100 according to an embodiment in a first configuration and a second configuration, respectively. The medical device is configured to promote healing of an aneurysm. More specifically, at least a portion of the medical device is configured to occupy at least a portion of the volume defined by a sac of the aneurysm and, in some embodiments, at least a portion of the medical device is configured to promote endothelial cell attachment over a neck of the aneurysm. Once endothelialization over the aneurysm neck is complete, blood flow into the aneurysm sac from a parent blood vessel (i.e., the vessel on which the aneurysm formed) is prevented.

The medical device 100 can include an insertion portion 102 and an expandable implant 110. The insertion portion 102 is coupled to the expandable implant 110, such as, for example, at a proximal portion 112 of the expandable implant 110. In some embodiments, the insertion portion 102 is removably coupled to the expandable implant 110. In this manner, the insertion portion 102 can be separated from the expandable implant 110 following delivery of the expandable implant to the aneurysm and removed from a patient's vasculature. The insertion portion 102 can be, for example, a guide wire or a distal end portion of a wire. The medical device 100 can be used with a cannula or catheter 104 (shown in dashed lines in FIGS. 1 and 2) to, for example, deliver the expandable implant 110 to the aneurysm.

The expandable implant 110 is configured to be deployed in the aneurysm (e.g., in a sac of an aneurysm). The expandable implant 110 has a first portion 120 and a second portion 130. As shown in FIG. 1, the expandable implant 110 has a first configuration in which the first portion 120 and the second portion 130 are substantially linearly aligned. In its first configuration, the expandable implant 110 is configured for insertion through a blood vessel. The expandable implant 110 is also configured for insertion through a neck of the aneurysm when in its first configuration.

The expandable implant 110 is movable between its first configuration and a second configuration in which the second portion 130 at least partially overlaps the first portion 120, as shown in FIG. 2. For example, the second portion 130 can be configured to bend, curve and/or twist in multiple turns such that multiple segments of the first portion 120 and the second portion 130 are overlapped. Additionally, at least one of the first portion 120 and the second portion 130 can be configured to bend or curve in multiple turns such that the respective first or second portion is overlapped with itself. In some embodiments, the expandable implant 110 can be understood to have multiple first portions and multiple second portions. In other words, the expandable implant can continually overlap itself in its deployed configuration to occupy all or substantially all of the volume of the aneurysm.

In its second configuration, the expandable implant 110 is configured to occupy at least a portion of the volume defined by the sac of the aneurysm. In some embodiments, when the expandable implant 110 is in its second configuration, at least a portion of the expandable implant is configured to be positioned over the neck of the aneurysm. For example, the portion of the expandable implant 110 at which the second portion 130 overlaps the first portion 120 can be configured to be positioned over the neck of the aneurysm. As such, the portion of the expandable implant 110 disposed over the aneurysm neck has an increased density (e.g., a dual density compared to the first portion 120 or the second portion 130 individually), which helps to limit or prevent blood flow from entering the sac of the aneurysm. The portion of the expandable implant 110 positioned over the aneurysm neck can be a scaffold for endothelial cell attachment at the aneurysm neck. For example, the portion of the expandable implant 110 positionable over the aneurysm neck can be porous, such as by including a porous mesh, as described in more detail herein. In some embodiments, the first portion 120 and the second portion 130 of the expandable implant 110 are biased to the second configuration.

As noted above, in some embodiments, at least a portion of the expandable implant 110 is porous. For example, in some embodiments, at least a portion of the expandable implant 110 can include and/or be constructed of a mesh (e.g., woven, braided, or laser-cut) material such that a wall or layer of the expandable implant 110 defines multiple openings or interstices 118. More specifically, in some embodiments, at least one of or both the first portion 120 and the second portion 130 of the expandable implant 110 can include the porous mesh. The porous mesh can have a first porosity when the expandable implant 110 is in its first configuration and a second porosity when the expandable implant is in its second configuration. More specifically, in some embodiments, the porous mesh can have a greater porosity when the expandable implant 110 is in its second configuration than when the expandable implant is in its first configuration. The porosity of the porous mesh can be increased, for example, because one or more individual pores or openings are larger when in the second configuration than in the first configuration. For example, the porous mesh can be expanded in the second configuration, thereby increasing the space between filaments of the mesh (and thus the size of one or more openings of the mesh). In other words, an overall volume of pore openings can be increased. In another example, the porosity of the porous mesh can be increased because one or more openings that were closed off when the expandable implant 110 was collapsed into its first configuration are reopened when the expandable implant is moved to its second configuration. In other words, a number of open pores can be increased.

In some embodiments, the first portion 120 and the second portion 130 can have one of the same or different porosities. For example, the first portion 120 can have a porosity greater than a porosity of the second portion 130. in another example, the second portion 130 can have a porosity greater than the porosity of the first portion 120. In still another example, the first and second portions 120, 130 can have substantially equivalent porosities in the expanded configuration.

In some embodiments, at least one of the first portion 120 and the second portion 130 includes one, two, three, or more layers. For example, in some embodiments, the first portion 120 of the expandable implant 110 includes a first layer (not shown in FIG. 1 or 2) of porous mesh and a second layer (not shown in FIG. 1 or 2) of porous mesh. The first layer and the second layer can have the same or different porosities. In some embodiments, the first layer is offset from the second layer. As such, the porosity of the first portion is determined by the porosities of the first and second layers and the manner in which the first layer is offset from the second layer.

In some embodiments, at least a portion of the expandable implant 110, such as at least one of the first portion 120 or the second portion 130 can include a shape-memory material, such as, for example, nitinol, and can be preformed to assume a desired shape. Thus, in such an embodiment, the portion of the expandable implant 110 (e.g., the first portion 120 and/or the second portion 130) can be biased into an expanded second configuration and moved to a collapsed first configuration by restraining or compressing the portion of the expandable implant.

In some embodiments, at least a portion of the expandable implant 110, such as at least one of the first portion 120 or the second portion 130 can include an electropositive material, described in more detail below.

The expandable implant 110 when in the expanded configuration can have a variety of different shapes, sizes and configurations. For example, in some embodiments, when in the expanded configuration the expandable implant 110 can be substantially spherical. In some embodiments, the expandable implant 110 can be substantially helical. In some embodiments, the expandable implant 110 can be substantially circular, disc-shaped, or ring-shaped. In some embodiments, the expandable implant 110 can be a custom-made shape based on a shape of a target aneurysm within a patient: for example, a shape modeled after the shape of the target aneurysm as detected by an imaging device. For example, an image of the aneurysm shape can be acquired using an angiogram, and the expandable implant 110 can be modeled after the shape of the aneurysm shown in the angiogram. In some embodiments, the expandable implant 110 can include multiple portions having varying outer perimeters or outer diameters. For example, in some embodiments, when in the expanded configuration the expandable implant 110 can include a first portion having a first outer perimeter, a second portion having a second outer perimeter and a third portion having a third outer perimeter. In such an embodiment, the second outer perimeter can be smaller than each of the first outer perimeter and the third outer perimeter.

In one example use of the medical device 100, a catheter 104 can be inserted into a blood vessel and directed to a desired treatment site near a vascular defect, such as the aneurysm. The expandable implant 110 is inserted into an elongate lumen of the catheter 104 for delivery to the treatment site. A distal portion of the catheter 104 is positioned adjacent the aneurysm within the blood vessel. The expandable implant 110 is moved from a first position inside the catheter to a second position outside the catheter. When the expandable implant 110 is in its first position, each of the first portion 120 and the second portion 130 are in a first configuration. For example, in the first configuration, each of the first and second portions 120, 130 can be compressed or collapsed within the lumen of the catheter 104 and are substantially linear in configuration.

The expandable implant 110 can be oriented with respect to an opening in the vessel wall in fluid communication with the aneurysm such that the expandable implant can enter a sac of the aneurysm when the expandable implant 110 is moved to its second position. The expandable implant 110 can be moved from its first position to its second position with the assistance of the insertion portion 102 such that the expandable implant 110 is directed into and positioned within a sac of the aneurysm. When the expandable implant 110 is in its second position, the first and second portions each have a second configuration. For example, in the second configuration, each of the first and second portions 120, 130 can be expanded into a three-dimensional shape. The three-dimensional shape of the first portion 120 in the second configuration can be similar to or different from the three-dimensional shape of the second portion 130. In the second configuration, the first portion 120 of the expandable implant 110 substantially overlaps the second portion 130. In some embodiments, the second portion 130 is disposed in an interior region defined by the first portion when each of the first portion and the second portion are in their respective second configurations.

The first and second portions 120, 130 can be moved to their respective second configurations concurrently or sequentially. For example, in some embodiments, the second portion 130 is moved to its second configuration before the first portion 120 is moved to its second configuration. The expandable implant 110 can assume a biased expandable configuration such that the walls of the expandable implant 110 contact at least a portion of the wall of the aneurysm and/or such that a portion of the expandable implant is disposed over the neck of the aneurysm. The presence of the expandable implant 110 over the neck of the aneurysm can substantially reduce and/or prevent further blood flow from the parent vessel into the aneurysm sac because the expandable implant can act as a physical flow disruptor for blood flowing from the parent vessel and as a scaffold for endothelial cell attachment at the aneurysm neck to promote endothelialization of the neck/vessel wall. The insertion portion 102 can then be disconnected from a proximal end of the expandable implant 110 and removed through the catheter 104.

FIGS. 3, 4, 5A, 5B and 5C illustrate a medical device according to an embodiment. The medical device 200 can include all or some of the same features and functions as described above for medical device 100. The medical device 200 includes an insertion portion 202 and an expandable implant 210. The expandable implant 210 is removably coupled at its proximal end to a distal end of the insertion portion 202.

Figure 4:
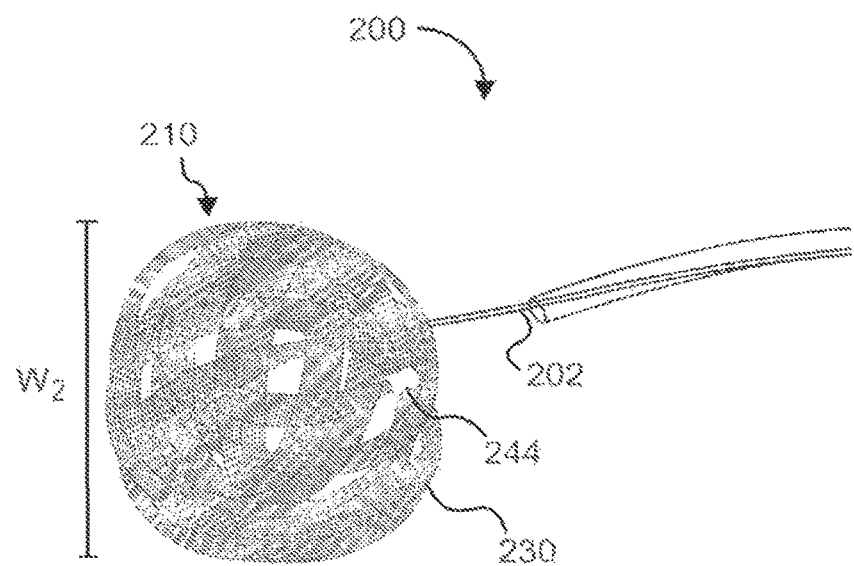
FIG. 4 is a side view of a medical device according to an embodiment in a second configuration.
Figure 5A:
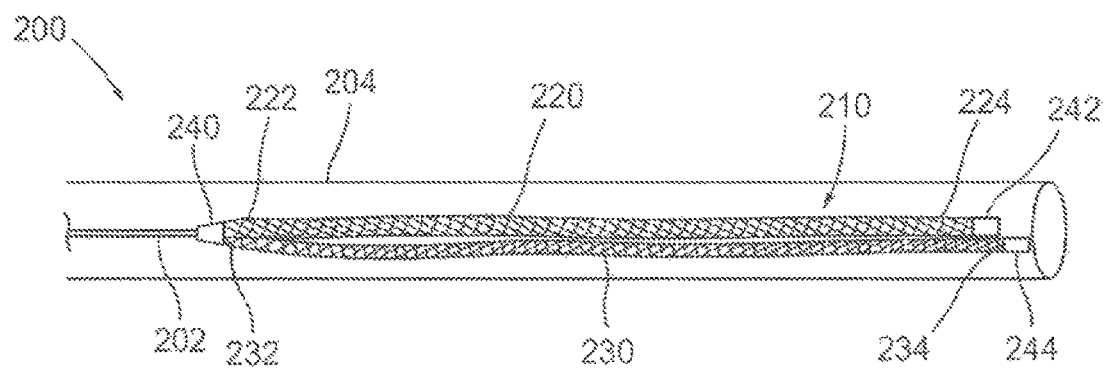
FIG. 5A is a view of the medical device of FIG. 3 in a first configuration during insertion into an aneurysm.
Figure 5B:
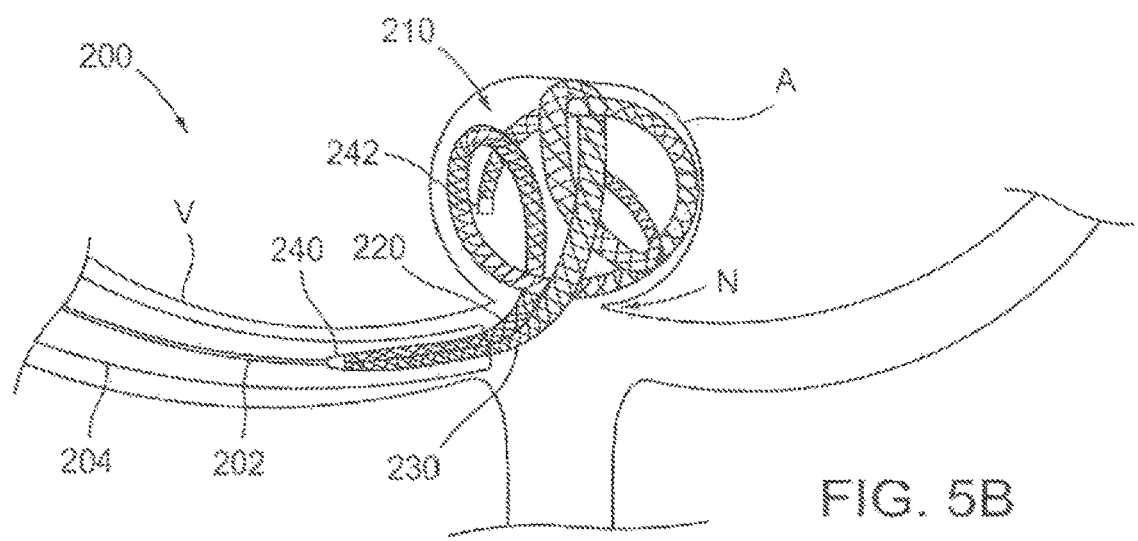
FIG. 5B is a view of the medical device of FIG. 3 in a second configuration during insertion into an aneurysm.

The expandable implant 210 includes a first portion 220 and a second portion 230. As shown in FIGS. 3 and 5A, the expandable implant 210 has a first, or collapsed, configuration in which the first and second portions 220, 230 are substantially linearly aligned. In this manner, the expandable implant 210 can be disposed within a lumen of a catheter 204 for delivery through a blood vessel V to a treatment site, such as to an aneurysm A. In its first configuration, the expandable implant 210 has a first width $W_1$, as shown in FIG. 2. As shown in FIGS. 4 and 5B-5C, the expandable implant 210 is moveable to a second, or expanded or deployed, configuration. The insertion portion 202 is configured to move the expandable implant 210 from the first configuration to the second configuration. The insertion portion 202 can be disconnected from the expandable implant 210 when the expandable implant 210 is in its second configuration.

In its second configuration, the expandable implant 210 is configured to occupy at least a portion of the volume defined by a sac of the aneurysm A. As such, the expandable implant 210 has a second width W2 in the second, expanded, configuration greater than its first width $W_1$. For example, the expandable implant 210 can be substantially narrow and elongate in its first configuration and can assume a three-dimensional shape in its second configuration. In the embodiments illustrated in FIGS. 3-5C, the expandable implant 210 has a substantially spherical shape in its second configuration. The expandable implant 210 can be compliant such that its three-dimensional shape can accommodate any irregularities in the shape of the aneurysm. In the second configuration, the second portion 230 of the expandable implant 210 at least partially overlaps the first portion 220. At least a portion of the expandable implant 210 is configured to be positioned over a neck N of the aneurysm A when the expandable implant is in its second configuration within the sac of aneurysm A. The expandable implant 210 is configured to facilitate endothelial cell attachment at the neck N of the aneurysm A, as described in more detail herein.

In the embodiment illustrated in FIG. 3, the first portion (or member) 220 is a first ribbon-like strand and the second portion (or member) 230 is a second ribbon-like strand discrete from the first portion. In other embodiments, an expandable implant can include a first portion and a second portion from a single ribbon-like strand (e.g., integrally or monolithically constructed), instead of discrete portions. A first end 222 of the first portion 220 is coupled to a first end 232 of the second portion 230. Any suitable mechanism for coupling the first end 222 of the first portion 220 to the first end 232 of the second portion 230 can be used, such as an adhesive, a mechanical coupler, a weld, or the like, or any combination of the foregoing. For example, the first ends 222, 232 can be coupled by a band 240. The band 240 can also be configured to help couple the insertion portion 202 to the expandable implant 210. The band 240 can be or can include, for example, a radiopaque marker.

A second end 224 of the first portion 220 and a second end 234 of the second portion 230 each have a radiopaque marker 242, 244, respectively, coupled thereto. The radiopaque markers 242, 244 are configured to facilitate imaging of the expandable implant 210 during delivery to the treatment site and/or subsequent to implantation. The markers 242, 244 are configured to be wholly disposed within the sac of the aneurysm A when the expandable implant 210 is in its second configuration. As such, the markers 242, 244 will not puncture the wall of the aneurysm A or the vessel V, and the markers 242, 244 will not interfere with endothelial cell attachment at the aneurysm neck. This is also beneficial because if the markers 242, 244 were positioned at or proximate to the neck of the aneurysm, blood from a parent blood vessel could have a tendency to clot around the marker.

When the expandable member 210 is moved between its first configuration and its second configuration, at least one of the first portion 220 and the second portion 230 is also moveable between a first configuration and a second configuration. The first portion or member 220 has a first, collapsed, configuration in which the first portion 220 is substantially elongate and has a first width. The first portion 220 has a second, expanded, configuration, in which the first portion 220 has a second width greater than the first width. For example, the first portion 220 can be moveable from a substantially linear, elongate collapsed configuration to a multi-dimensional (e.g., three-dimensional) shape in the expanded or deployed configuration. As shown in FIGS. 4 and 5C, the first portion 220 can have a three-dimensional shape in the expanded configuration that lends an overall spherical shape to the expandable implant 210. The first portion 220 can be biased to its second, expanded, configuration.

The first portion or member 220 is porous and, for example, can include or be constructed of a porous mesh. The porous mesh can be formed using filaments that are woven or braided together in a manner that openings or interstices are present between portions of the filaments at least when the expandable implant 210 is in its second configuration. For example, the porous mesh can include a plurality of braided wires. Suitable mesh material is described in more detail herein. The porous mesh can have a first porosity when the first portion 220 is in the first configuration and a second porosity when the first portion 220 is in the second configuration. For example, when the first portion 220 is moved from its first, collapsed, configuration to its second, expanded, configuration, the mesh can be expanded such that the size of the openings of the mesh is increased, thus increasing the porosity of the mesh. The porous mesh is configured to act as a scaffold that promotes clot formation and endothelium cell attachment when the mesh is disposed within the aneurysm A. Specifically, endothelial cells will migrate to the openings of the mesh.

The first portion 220 of the expandable implant 210 includes a first layer of porous mesh and a second layer of porous mesh. In this manner, the density of the first portion 220 is greater than the density of either the first or second layers individually. Such a dual-density structure can help to limit or prevent blood flow into the aneurysm A, for example when the first and second layers of the first portion 220 are disposed over the neck N of the aneurysm A. The first layer of porous mesh and the second layer of porous mesh can have the same porosities, or different porosities. The first layer of porous mesh can be offset from the second layer of porous mesh. In this manner, the overall porosity of the first portion 220 is greater than the porosity of either the first or second layers individually. The first and second layers of porous mesh can be coupled together in any suitable manner. For example, the first portion 220 can be formed using an elongate tubular mesh having an elongate lumen therethrough. In such an embodiment, the elongate mesh can be flattened from a tubular structure to a ribbon-like structure such that a first side, or layer, of the mesh is disposed on or proximate to a second side, or layer, of the mesh, thus forming a dual density, or dual-layered, mesh structure.

The second portion, or member, 230 of the expandable implant 210 can be configured the same as or similar to, and can be used in the same or similar manner, as the first portion 220. When the expandable member 210 is moved between its first configuration and its second configuration, the second portion 230 is also moveable between a first, collapsed, configuration in which the second portion is substantially elongate and has a third width, and a second, expanded, configuration, in which the second member has a fourth width greater than the third width. For example, the second portion 230 can be moveable from a substantially linear, elongate collapsed configuration to a multi-dimensional (e.g., three-dimensional) shape in the expanded configuration. As shown in FIGS. 4 and 5C, the second portion 230 can have a three-dimensional shape in the expanded configuration that lends an overall spherical shape to the expandable implant 210. The second portion 230 can be biased to its second, expanded, configuration.

The second portion 230 is porous and can include or be constructed of a porous mesh. The porous mesh can be configured the same as or similar to, and can be used in the same or similar manner, as the porous mesh described above with respect to the first portion 220 of the expandable implant 210. For example, the porous mesh can include a weave or braid of filaments that is porous at least when the expandable implant 210 is in its second configuration. Additionally, the porous mesh of the second portion 230 can have a first porosity when the second portion 230 is in the first configuration and a second porosity when the second portion 230 is in the second configuration. In some embodiments, the second portion 230 of the expandable implant 210 includes a first layer of porous mesh and a second layer of porous mesh, which can be of the same or different porosities. In this manner, the total density of the second portion 230 is greater than the density of either the first or second layers individually. The first layer of porous mesh can be offset from the second layer of porous mesh such that the overall porosity of the second portion 230 is greater than the porosity of either the first or second layers individually. Similarly as described above with respect to the first portion 220, the first and second layers of porous mesh of the second portion 230 can be formed from a monolithically constructed elongate tubular mesh that is flattened into a ribbon-like structure.

The first portion 220 and the second portion 230 of the expandable implant 210 can be the same or different sizes. For example, as shown in FIG. 5A, the first portion 220 can have a length in its first, collapsed, configuration, that is less than a length of the second portion 230 in its first, collapsed, configuration. In this manner, the markers 242, 244 will be sequentially introduced through the neck N of the aneurysm A, which permits the expandable implant 210 to be introduced through a narrower neck N. In another example, the first portion 220 and the second portion 230 can have the same or different widths. In some embodiments, for example, the first width of the first portion 220 in its first configuration is wider than the third width of the second portion 230 in its first configuration. The second width of the first portion 220 in its second configuration can also be wider than the fourth width of the second portion 230 in its second configuration. In another example, the fourth, expanded, width of the second portion 230 can be greater than the second, expanded, width of the first portion 220. In some embodiments, the porous mesh of the first portion 220 can have a multi-dimensional shape with a first width when the expandable implant 210 is in its second configuration, and the porous mesh of the second portion 230 can have a multi-dimensional shape with a second width less than the first width when the expandable implant is in its second configuration.

In some embodiments, for example, the first portion 220 (or the porous mesh of the first portion) can have a width of about 8 mm when the expandable implant is expanded in its second configuration, and the second portion 230 (or the porous mesh of the second portion) can have a width of about 9.5 mm when the expandable implant is expanded in its second configuration. As such, in an embodiment in which the first portion 220 has a smaller overall size in the expanded configuration than the second portion 230, the first portion 220 can be configured to be disposed within an open interior region formed by the second portion 230 in its second configuration.

In some embodiments, a variation of medical device 200 is contemplated. For example, in such an embodiment, the first portion of the expandable implant can include a first tubular mesh that defines a lumen therethrough, and the second portion of the expandable implant can include a second tubular mesh disposed within the lumen of the first tubular mesh. The first and second tubular mesh structures can be formed into a substantially ribbon-like strand. As such, the expandable implant has a four-layer density. The expandable implant can include additional ribbon-like strands in addition to the strand formed by the first and second portions. For example, the expandable implant can include one, two, three, four, five, six, seven, eight, or nine strands, with each of the strands having a desired number of layers (e.g., two, four, or more layers). As such, an expandable implant can be formed that has a desired amount of density. As noted above, a highly dense structure helps to prevent blood flow from the parent blood vessel into the aneurysm. Each layer or portion of the expandable implant can have the same or different density as the other layers or portions. Furthermore, each layer or portion of the expandable implant can have the same or different porosity as the other layers or portions.

Figure 6:
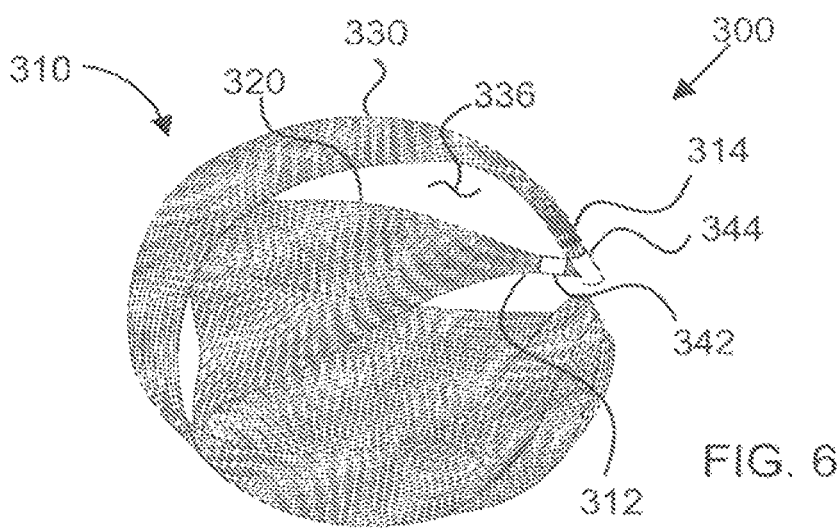
FIG. 6 is a view of a portion of a medical device in an expanded configuration, according to an embodiment.

FIG. 6 illustrates a portion of another embodiment of a medical device. The medical device 300 can include the same or similar features and functions as described above for previous embodiments. For example, the medical device 300 includes an expandable implant 310 and an insertion portion or member (not shown in FIG. 6). The expandable implant 310 is shown in an expanded configuration and can be moved between a compressed or collapsed configuration in which the expandable implant is substantially elongate and the expanded configuration in the same or similar manner as described above for expandable implant 210. In the expanded configuration, a first portion 320 of the expandable implant 310 is overlapped by a second portion 330 of the expandable implant. Additionally, at least a portion of the first portion 320 is disposed within an open interior region 336 defined by the second portion 330 when the expandable implant 310 is in its expanded configuration.

The expandable implant 310 includes a ribbon-like strand of porous mesh. At least a portion of the porous mesh is configured to be positioned over a neck of an aneurysm when the expandable implant 310 is in the expanded configuration. The porous mesh is configured to bend, curve, and/or twist at multiple turns into a substantially spherical shape when the expandable implant 310 is in the expanded configuration. The porous mesh can be a ribbon-like structure that is wider than the porous mesh of expandable implant 210. In this manner, the porous mesh of expandable implant 310 can be a shorter length than that of expandable implant 210 and still provide a similar amount of coverage within the aneurysm (and over the neck of the aneurysm) as expandable implant 210. The porous mesh can include one, two, or more layers depending on the desired density and porosity of the expandable implant 310. In some embodiments, a first radiopaque marker 342 is coupled to a first end 312 of the expandable implant 310 and a second radiopaque marker 344 is coupled to a second end 314 of the expandable implant. The expandable implant 310 is configured to be wholly disposed within the aneurysm such that the radiopaque markers 342, 344 are wholly disposed within the aneurysm sac and the porous mesh is disposed over the neck of the aneurysm. In some embodiments, the radiopaque markers are configured to be positioned at a side of the aneurysm (i.e., disposed away from the neck of the aneurysm).

Figure 7:
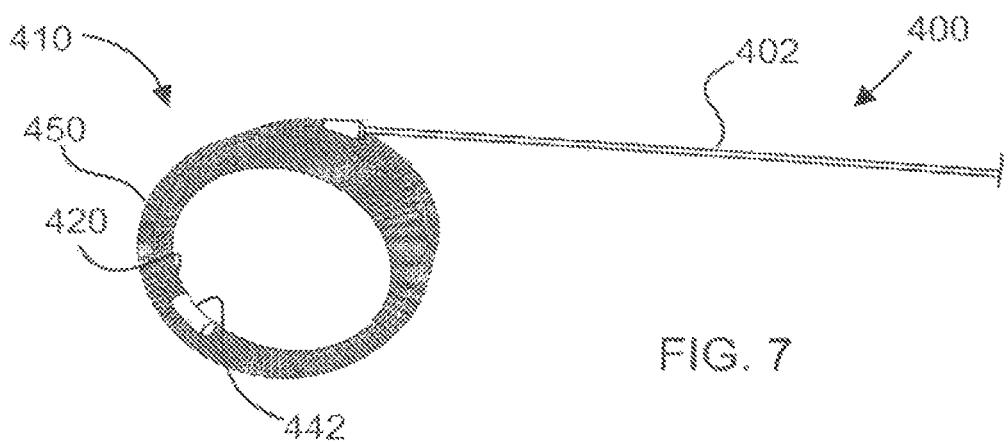
FIGS. 7-13 are views of a medical device in an expanded configuration, according to embodiments.

FIG. 7 illustrates another embodiment of a medical device. The medical device 400 can include the same or similar features and functions as described above for previous embodiments. For example, the medical device 400 includes an expandable implant 410 and an insertion portion or member 402. The expandable implant 410 is sized to occupy the sac of an aneurysm, and the insertion member 402 is configured to facilitate delivery of the expandable implant into the sac of the aneurysm. The expandable implant 410 is shown in an expanded configuration and can be moved between a compressed or collapsed configuration and the expanded configuration in the same or similar manner as described above for previous embodiments.

The expandable implant 410 includes at least one ribbon-like strand of porous mesh configured to be expanded within the aneurysm as a 360 degree spiral or ring-shaped structure. In the expanded configuration, a first portion 420 of the expandable implant 410 is overlapped by a second portion (not shown in FIG. 7) of the expandable implant, which is overlapped by a third portion 450 of the expandable implant. In this manner, at least a portion of the expandable implant 410 includes two, three, four, or more layers of implant material (e.g., porous mesh, as described above in previous embodiments), which can be positioned over the neck of the aneurysm from within the aneurysm to function as a dense flow disruptor. In some embodiments, a radiopaque marker 442 is coupled to the expandable implant 410.

Figure 8:
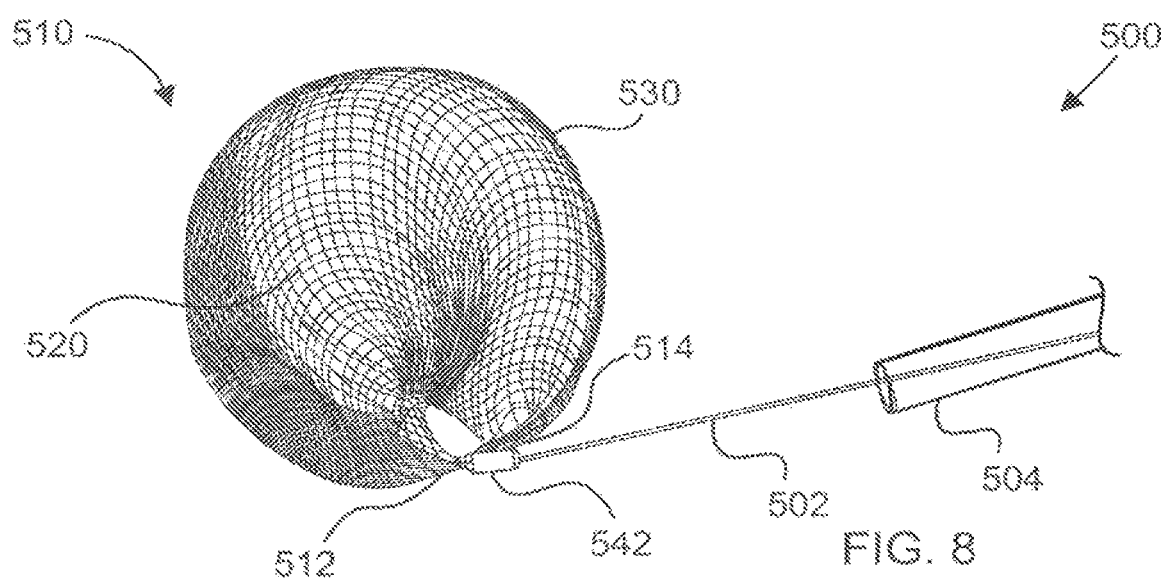

FIG. 8 illustrates another embodiment of a medical device. The medical device 500 can include the same or similar features and functions as described above for medical device 400. For example, the medical device 500 includes an expandable implant 510 and an insertion portion or member 502. The medical device 500 can be delivered to an aneurysm or other vascular defect using a microcatheter 504. The expandable implant 510 is sized to occupy at least a portion of the volume defined by the sac of the aneurysm, and the insertion member 502 is configured to facilitate delivery of the expandable implant into the sac of the aneurysm. The expandable implant 510 is shown in an expanded configuration and can be moved between a compressed or collapsed configuration and the expanded configuration in the same or similar manner as described above for previous embodiments.

The expandable implant 510 includes a porous mesh configured to be expanded within the aneurysm as a substantially circular or disc-shaped structure, as shown in FIG. 8. In the expanded configuration, a first end portion 512 of the expandable implant 510 is engaged with and/or overlapped with a second end portion 514 of the expandable implant. The expandable implant 510 includes a first portion 520 having a first density of porous mesh and a second portion 530 having a second, higher, density of porous mesh. More specifically, a weave or braid of the porous mesh has a higher density in the second portion 530 than in the first portion 520 of the expandable implant. The expandable implant 510 is configured to be disposed within the aneurysm (or other vascular defect) such that at least a portion of the second portion 530 is disposed over the neck of the aneurysm, because the higher density promotes endothelial cell attachment to the expandable implant. The expandable implant 510 includes at least one radiopaque marker 542, which can be disposed on one of the first end portion 512 (as shown in FIG. 8) and/or the second end portion 514. When the expandable implant 510 is disposed within the aneurysm in its expanded configuration such that the higher density second portion 530 is disposed over the neck of the aneurysm, the at least one radiopaque marker 542 is disposed within the sac of the aneurysm away from the neck of the aneurysm.

Figure 9:
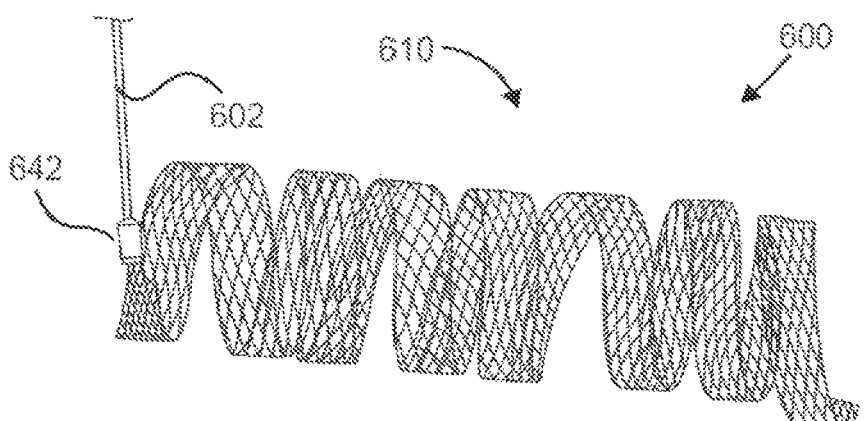

FIG. 9 illustrates another embodiment of a medical device. The medical device 600 can include the same or similar features and functions as described above for previous embodiments. For example, the medical device 600 includes an expandable implant 610 and an insertion portion or member 602. The expandable implant 610 is sized to occupy at least a portion of a volume defined by the sac of the aneurysm, and the insertion member 602 is configured to facilitate delivery of the expandable implant into the sac of the aneurysm. The expandable implant 610 is shown in an expanded configuration and can be moved between a compressed or collapsed configuration and the expanded configuration in the same or similar manner as described above for previous embodiments.

The expandable implant 610 includes a ribbon-like strand of porous mesh having at least two layers of mesh. The expandable implant 610 is configured to be expanded within the aneurysm as a substantially helical or coil shaped structure, as shown in FIG. 9. The expandable implant 610 can be disposed within the aneurysm (or other vascular defect) such that at least a portion of the implant is disposed over the neck of the aneurysm to facilitate endothelial cell attachment at the neck. The expandable implant 610 includes at least one radiopaque marker 642, which can be disposed on an end of the expandable implant 610, as shown in FIG. 9. The insertion member 602 can be removably coupled to the expandable implant at the radiopaque marker.

Figure 10:
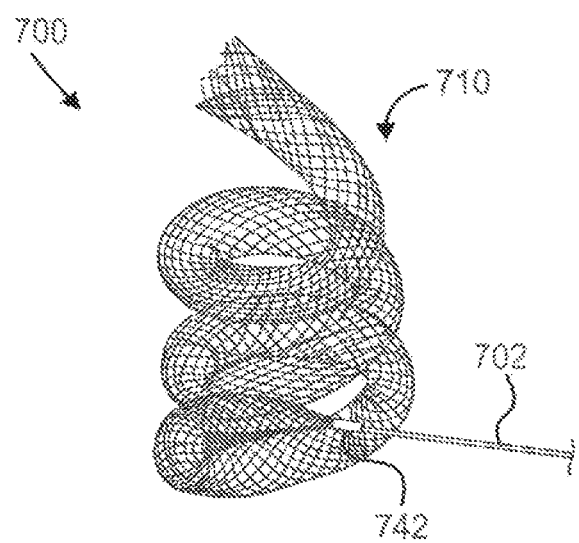

FIG. 10 illustrates another embodiment of a medical device. A medical device 700 includes all the same or similar features and functions as described above for medical device 600. For example, the medical device 700 includes an expandable implant 710, an insertion portion or member 702, and a radiopaque marker 742 coupled to an end of the expandable implant. The expandable implant 710 includes a porous mesh formed of a tubular or rounded braid structure. The rounded braid structure can lend more softness to the expandable implant 710 than, for example, the flattened ribbon-like structure previously described.

Figure 11:
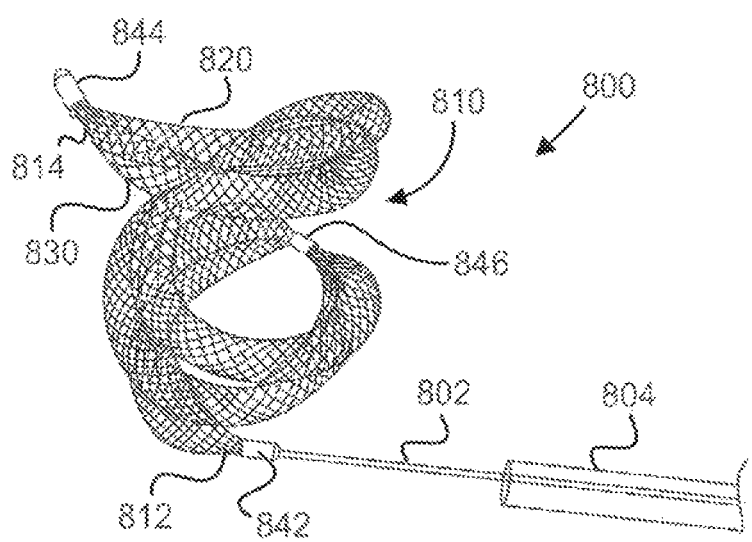

FIG. 11 illustrates another embodiment of a medical device. The medical device 800 can include the same or similar features and functions as described above for previous embodiments. For example, the medical device 800 includes an expandable implant 810 and an insertion portion or member 802. The medical device 800 can be delivered to an aneurysm or other vascular defect using a microcatheter 804. The expandable implant 810 is sized to occupy at least a portion of the volume of the sac of the aneurysm, and the insertion member 802 is configured to facilitate delivery of the expandable implant from the microcatheter 804 into the sac of the aneurysm. The expandable implant 810 is shown in an expanded configuration and can be moved between a compressed or collapsed configuration and the expanded configuration in the same or similar manner as described above for previous embodiments.

The expandable implant 810 includes a first member 820 and a second member 830. The first and second members 820, 830 are coupled at a first end 812 of the expandable implant 810 and a second end 814 of the expandable implant. The first and second members 820, 830 are also coupled together at at least one middle portion of the expandable implant 810 between the first end 812 and the second end 814. The first and second members 820, 830 can be coupled, for example, using radiopaque markers 842, 844, 846. Each site of coupling is configured to be a folding point of the expandable implant 810 when the expandable implant is delivered into the aneurysm and is expanded within the aneurysm to comply with the shape of the aneurysm. As such, the expandable implant 810 can be more densely packed into the aneurysm, for example, as compared to an implant that cannot bend or fold in response to the shape of the aneurysm. At least one of the first member 820 and the second member 830 of the expandable implant 810 includes a porous mesh formed of a tubular or rounded braid structure.

Figure 12:
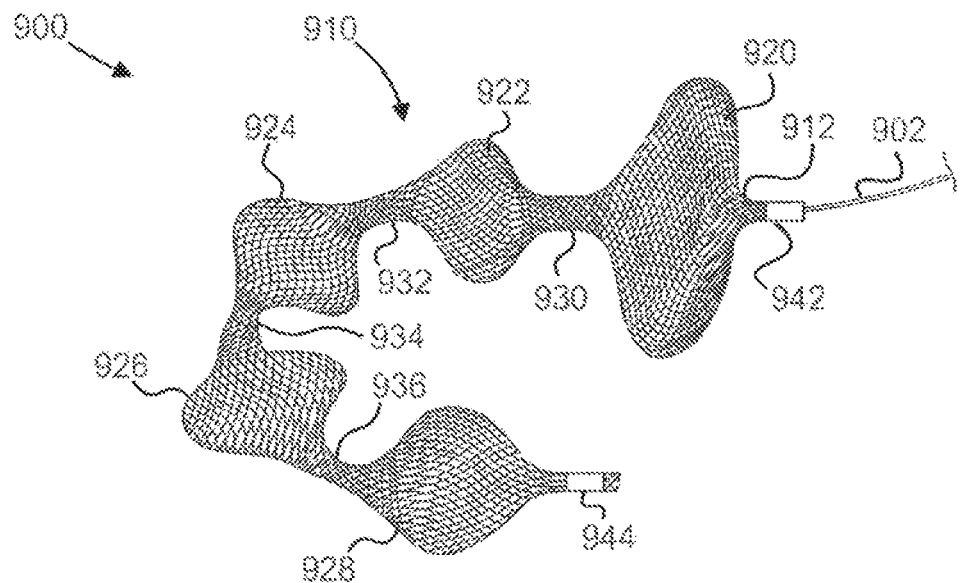

FIG. 12 illustrates another embodiment of a medical device. The medical device 900 can include the same or similar features and functions as described above for previous embodiments. For example, the medical device 900 includes an expandable implant 910 and an insertion portion or member 902. The expandable implant 910 is sized to occupy the sac of the aneurysm, and the insertion member 902 is configured to facilitate delivery of the expandable implant from a microcatheter (not shown in FIG. 12) into the sac of the aneurysm. The expandable implant 910 is shown in an expanded configuration and can be moved between a compressed or collapsed configuration and the expanded configuration in the same or similar manner as described above for previous embodiments.

The expandable implant 910 includes a series of expandable portions 920, 922, 924, 926, 928 separated by a series of constricted portions 930, 932, 934, 936. The expandable portions 920, 922, 924, 926, 928 can be configured to expand to any suitable multi-dimensional shape, including, for example, that resembling a sphere, a disc, a parabola, or the like. Additionally, each expandable portion 920, 922, 924, 926, 928 can have an expanded shape distinct from an expanded shape of another expandable portion.

When the expandable implant 910 is in its expanded configuration, as shown in FIG. 12, the expandable portions 920, 922, 924, 926, 928 are more porous and less dense then the constricted portions 930, 932, 934, 936. The density and/or porosity of each expandable portion 920, 922, 924, 926, 928 can be varied from the other expandable portions 920, 922, 924, 926, 928, and the density and/or porosity of each expandable portion 920, 922, 924, 926, 928 can be varied along a length and/or width of the respective expandable portion. For example, a first expandable portion 920 can be more dense and/or less porous proximate to a first constriction portion 930 and less dense and/or more porous at a middle, wider portion of the first expandable portion 920. Additionally, the expandable portions 920, 922, 924, 926, 928 are each configured to have a width greater than when the expandable implant 910 is in its collapsed configuration, and the constricted portions 930, 932, 934, 936 are each configured to have a width narrower than a width of the expandable portions 920, 922, 924, 926, 928. As such, the expandable implant 910 is configured to bend, curve, and/or fold at the constricted portions 930, 932, 934, 936 to help comply with the shape of the aneurysm.

When the expandable implant 910 is in its expanded configuration, the first expandable portion 920 is configured to have a width greater than the width of the other expandable portions 922, 924, 926, 928. The first expandable portion 920 can be, as illustrated in FIG. 12, the most proximal of the expandable portions 920, 922, 924, 926, 928. The first expandable portion 920 is configured to be positioned over a neck of the aneurysm when the expandable implant 910 is disposed within the aneurysm in its expanded configuration. In this manner, the first expandable portion 920 is configured to act as a flow disruptor at the neck of the aneurysm to help limit the flow of blood into the aneurysm from the parent blood vessel. The remaining, more distal, expandable portions 922, 924, 926, 928 are configured to be packed into the aneurysm to embolize the aneurysm.

The expandable implant 910 includes a first radiopaque marker 942 coupled to a first end 912 of the implant and a second radiopaque marker 944 coupled to a second end 914 of the implant. The radiopaque markers 942, 944 are configured to be wholly disposed within the sac of the aneurysm when the expandable implant 910 is disposed in the aneurysm in its expanded configuration.

Figure 13:
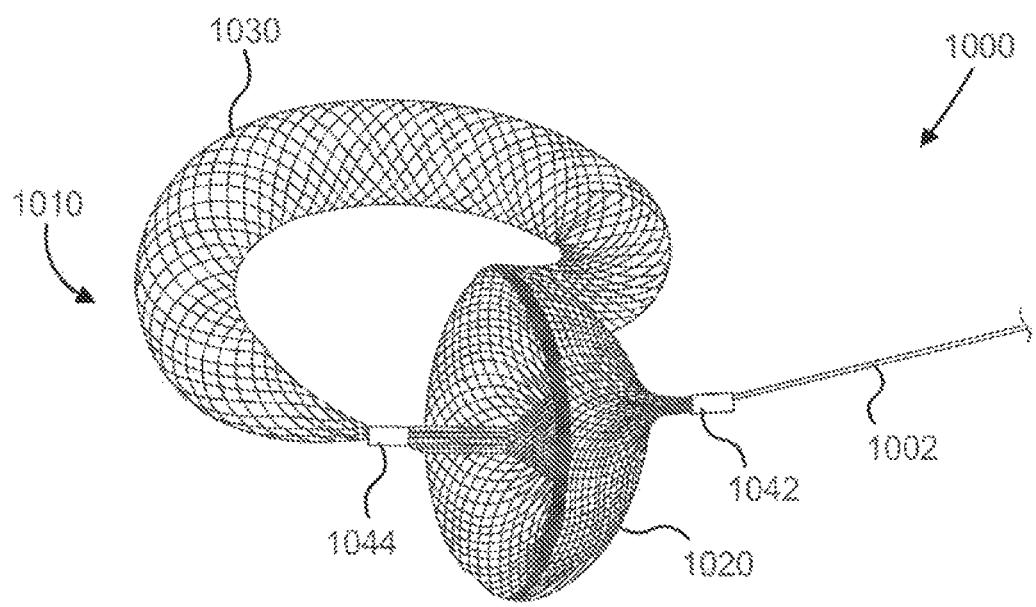

FIG. 13 illustrates another embodiment of a medical device. The medical device 1000 can include the same or similar features and functions as described above for previous embodiments. For example, the medical device 1000 includes an expandable implant 1010 and an insertion portion or member 1002. The expandable implant 1010 is sized to occupy the sac of the aneurysm, and the insertion member 1002 is configured to facilitate delivery of the expandable implant into the sac of the aneurysm. The expandable implant 1010 is shown in an expanded configuration and can be moved between a compressed or collapsed configuration and the expanded configuration in the same or similar manner as described above for previous embodiments.

The expandable implant 1010 includes a first porous member 1020 and a second porous member 1030. The first porous member 1020 includes a porous mesh configured to have a multi-dimensional shape when the expandable implant 1010 is in its expanded configuration. As such, the first porous member 1020 has a second width in the expanded configuration that is greater than a first width of the first porous member in the collapsed configuration. The first porous member 1020 can be configured to expand to any suitable multi-dimensional shape, including, for example, that resembling a parabola, as shown in FIG. 13, a sphere, a disc, or the like. The first porous member 1020 is configured to be positioned over a neck of the aneurysm when the expandable member 1010 is disposed within the sac of the aneurysm to disrupt and/or stop the flow of blood into the aneurysm from the parent blood vessel. Additionally, the porous mesh of the first porous member 1020 is configured to promote endothelial cell attachment at the neck of the aneurysm, which can help to heal over the neck of the aneurysm.

The second porous member 1030 includes a porous mesh configured to have a multi-dimensional shape when the expandable implant 1010 is in its expanded configuration. As such, the second porous member 1030 has a fourth width in the expanded configuration greater than a third width of the second porous member in the collapsed configuration. The second porous member 1030 can be configured to expand to any suitable multi-dimensional shape, including, for example, that resembling a tube, as shown in FIG. 13, a sphere, a disc, a parabola, or the like. In the embodiment illustrated in FIG. 13, the second width of the first porous member 1020 is greater than the fourth width of the second porous member 1030. The second porous member 1030 is configured to be disposed within the sac of the aneurysm such that the first porous member 1020 is disposed between the second porous member 1030 and the neck of the aneurysm. The second porous member 1030 is configured to be packed into the aneurysm to embolize the aneurysm.

A radiopaque marker 1044 is disposed between the first porous member 1020 and the second porous member 1030, and can be used to couple the first and second porous members. The expandable implant 1010 is configured to bend, curve, and/or fold at the radiopaque marker 1044, which can help the expandable implant 1010 comply with the shape of the sac of the aneurysm. Another radiopaque marker 1042 can be disposed on a proximate end of the expandable implant 1010, and can be used to couple the insertion portion 1002 to the expandable implant. The radiopaque markers 1042, 1044 are configured to be wholly disposed within the sac of the aneurysm when the expandable implant 1010 is disposed in the aneurysm in its expanded configuration.

Figure 14:
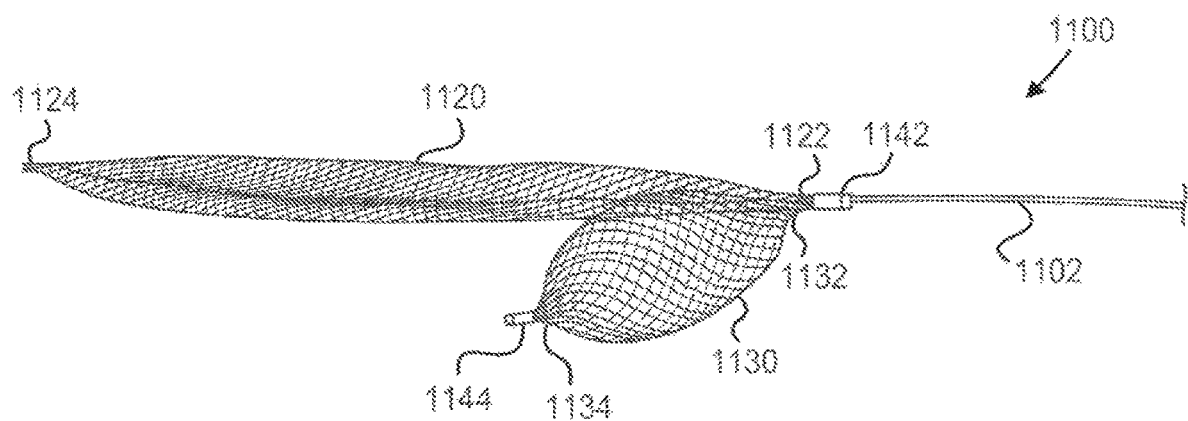
FIG. 14 is a view of a medical device in a partially collapsed configuration, according to an embodiment.
Figure 15:
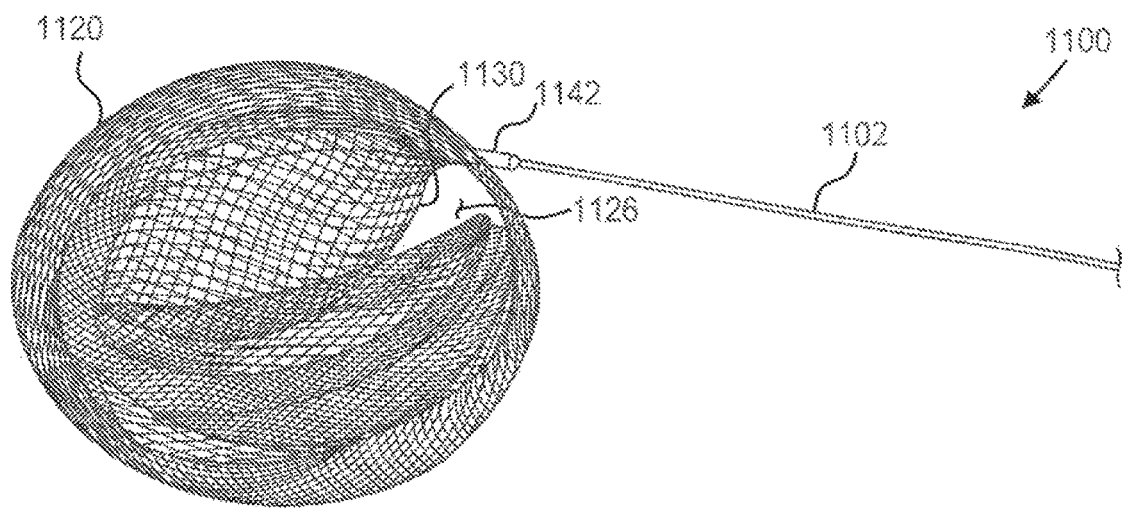
FIG. 15 is a view of the medical device of FIG. 14 in an expanded configuration, according to an embodiment.

FIGS. 14-15 illustrate another embodiment of a medical device. The medical device 1100 can include the same or similar features and functions as described above for previous embodiments. For example, the medical device 1100 includes a first porous member 1120, a second porous member 1130, and an insertion portion or member 1102 removably couplable to the first and second porous members 1120, 1130.

The first porous member 1120 has a first end 1122 and a second end 1124. As shown in FIG. 14, the first porous member 1120 has a collapsed configuration for insertion through a blood vessel. In its collapsed configuration, the first porous member 1120 is substantially elongate with a first length. As shown in FIG. 15, the first porous member 1120 has an expanded configuration for occupying a sac of an aneurysm. When the first porous member 1120 is in its expanded configuration, it has a three-dimensional shape and defines an open interior region 1126. The first porous member 1120 can have any suitable three-dimensional shape. For example, the first porous member 1120 can be configured to curve into a substantially spherical shape, as shown in FIG. 15. Additionally, in its expanded configuration, the first porous member 1120 includes a first segment configured to overlap with a second segment, which can be similar in many respects as described above with respect to expandable implants 210 and 310, for example. For example, the first porous member 1120 can include a mesh having a first segment configured to overlap with a second segment of the porous mesh to form a higher density portion of the first porous member 1120.

The second porous member 1130 has a first end 1132 and a second end 1134. The second porous member 1130 has a collapsed, first, configuration (not shown in FIG. 14 or 15) for insertion through a blood vessel. In its collapsed configuration, the second porous member 1130 is substantially elongate with a second length less than the first length of the first porous member, and is configured to occupy a first volume. As shown in FIGS. 14 and 15, the second porous member 1130 has an expanded, second, configuration for occupying at least a portion of the volume of the sac of the aneurysm. When the second porous member 1130 is in its expanded configuration, it has a three-dimensional shape and is configured to occupy a second volume greater than the first volume. The second porous member 1130 can have any suitable three-dimensional shape. For example, the second porous member 1130 can be configured to expand into a substantially ball (e.g., spherical, round, oblong, or the like) shape, as shown in FIGS. 14 and 15. In the expanded configuration, the second porous member 1130 can have a porosity the same as, or different than, a porosity of the first porous member 1120. The second porous member 1130 is configured to be disposed in the interior region 1126 of the first porous member 1120 when each of the first porous member and the second porous member are in the deployed or expanded configurations.

In the embodiment illustrated in FIGS. 14 and 15, the second porous member 1130 is coupled to the first porous member 1120. Specifically, the first end 1122 of the first porous member 1120 is coupled to the first end 1132 of the second porous member 1130. At least one of the first porous member 1120 and the second porous member 1130 includes a radiopaque marker. As shown in FIG. 14, a first radiopaque marker 1142 can be disposed on the first ends 1122, 1132 of the first and second porous members 1120, 1130 to couple the first and second porous members together. A second radiopaque marker 1144 can be disposed on the second end 1134 of the second porous member 1130. When the first and second porous members 1120, 1130 are in their respective expanded configurations, the second radiopaque marker 1144 is disposed within the interior region defined by the first porous member 1120.

In use, the first and second porous members 1120, 1130, and the first and second radiopaque markers 1142, 1194, are wholly disposed within the aneurysm. The second porous member 1130 can be inserted into the aneurysm first and assume its expanded configuration therein. The first porous member 1120 can then be inserted into the aneurysm such that the first porous member curves, coils, or otherwise wraps around the second porous member 1130 as the first porous member moves to its expanded configuration. The first porous member 1120 is configured to be disposed within the aneurysm such that a portion of the first porous member is disposed over the neck of the aneurysm. For example, the higher density portion of the first porous member 1120 at which the first segment overlaps the second segment can be positioned over the neck of the aneurysm to promote endothelial cell attachment at the aneurysm neck. The second porous member 1130 can help to embolize the aneurysm by providing additional porous mesh within the sac of the aneurysm for cell attachment and/or clot formation. As such, the second porous member occupies a portion of the volume of the sac of the aneurysm such that blood flow through the aneurysm is further inhibited.

Although the medical device 1100 includes discrete first and second porous members 1120, 1130, respectively, in other embodiments, the first and second porous members can be differently constructed. For example, referring to FIG. 16, an embodiment of a medical device 1200 is illustrated. The medical device 1200 can include the same or similar features and functions as described above for medical device 1100, or other previous embodiments. For example, the medical device 1200 includes a first porous member 1220, a second porous member 1230, and an insertion portion or member (not shown in FIG. 16) removably couplable to the first and second porous members. Each of the first porous member 1220 and the second porous member 1230 can be similar in form and function as the first porous member 1120 and the second porous member 1130, respectively, described above.

Figure 16:
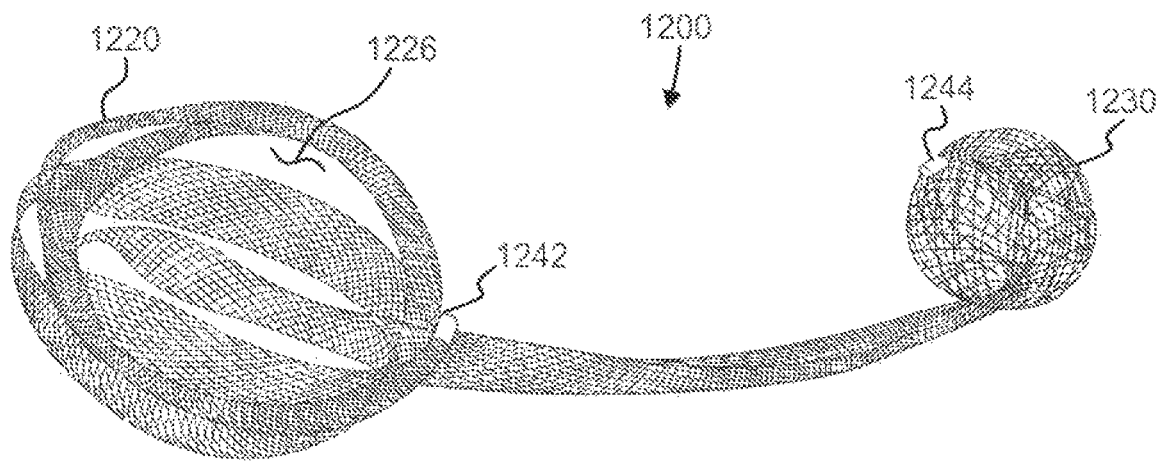
FIG. 16 is a view of a portion of a medical device in an expanded configuration according to an embodiment, with a first portion spaced apart from a second portion.

In the embodiment illustrated in FIG. 16, however, the second porous member 1230 is monolithically constructed with the first porous member 1220. It should be noted that in FIG. 16, the first and second porous members 1220, 1230, are shown in an expanded configuration but the second porous member 1230 is shown spaced apart from the first porous member 1220 for illustration purposes only. In use, in their respective deployed or expanded configurations, the second porous member 1230 is disposed within an interior region 1226 defined by the first porous member 1220 in a similar manner as that illustrated in FIG. 15 with respect to medical device 1100. Additionally, the medical device 1200 includes two radiopaque markers 1242, 1244. A first radiopaque marker 1242 is disposed at an end of a porous mesh of the first porous member 1220, and the second radiopaque marker 1244 is disposed at an opposing end of porous mesh of the second porous member 1230.

Figure 17A:
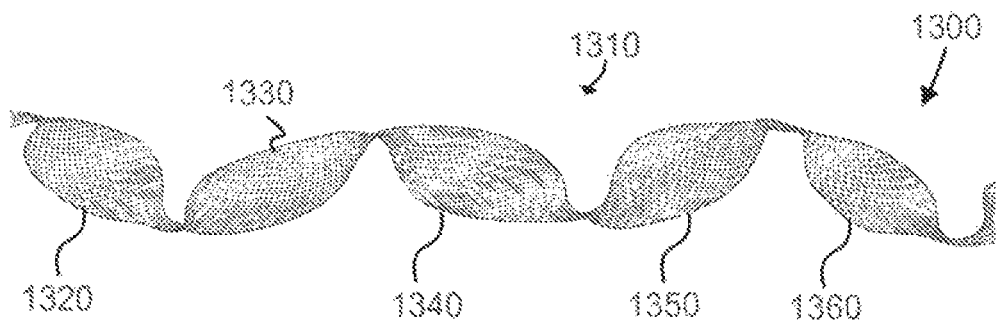
FIG. 17A is a view of a portion of a medical device in a collapsed configuration according to an embodiment.
Figure 17B:
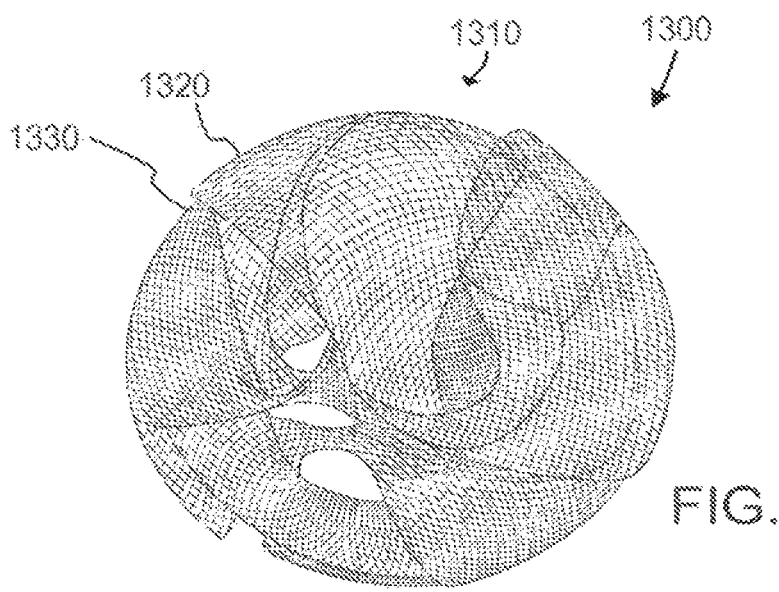
FIG. 17B is a view of a portion of a medical device in an expanded configuration according to an embodiment.

In some embodiments, a medical device includes an expandable implant that has a substantially continuous outer surface when in an expanded configuration. Referring to FIGS. 17A and 17B, a portion of a medical device 1300 according to an embodiment is illustrated in a collapsed configuration and an expanded configuration, respectively. The medical device 1300 can include the same or similar features and functions as described herein for other embodiments. For example, the medical device 1300 can include an expandable implant 1310 configured to move from the collapsed configuration (e.g., for delivery through a blood vessel) to the expanded configuration (e.g., for deployment within an aneurysm). The expandable implant 1310 includes at least a first portion 1320 and a second portion 1330, and can include additional portions 1340, 1350, 1360. When the expandable implant 1310 is in its expanded configuration, the expandable implant 1310 has a three-dimensional shape (e.g., a substantially spherical shape) with a substantially continuous outer surface such that edges of at least two of the portions 1320, 1330, 1340, 1350, 1360 overlap. For example, edges of the first portion 1320 and the second portion 1330 can overlap, as shown in FIG. 17B. In other words, the expandable implant 1310 moves into the expanded configuration such that few or no openings or spaces remain between edges of the portions 1320, 1330, 1340, 1350, 1360 of the expandable implant 1310.

Figure 18:
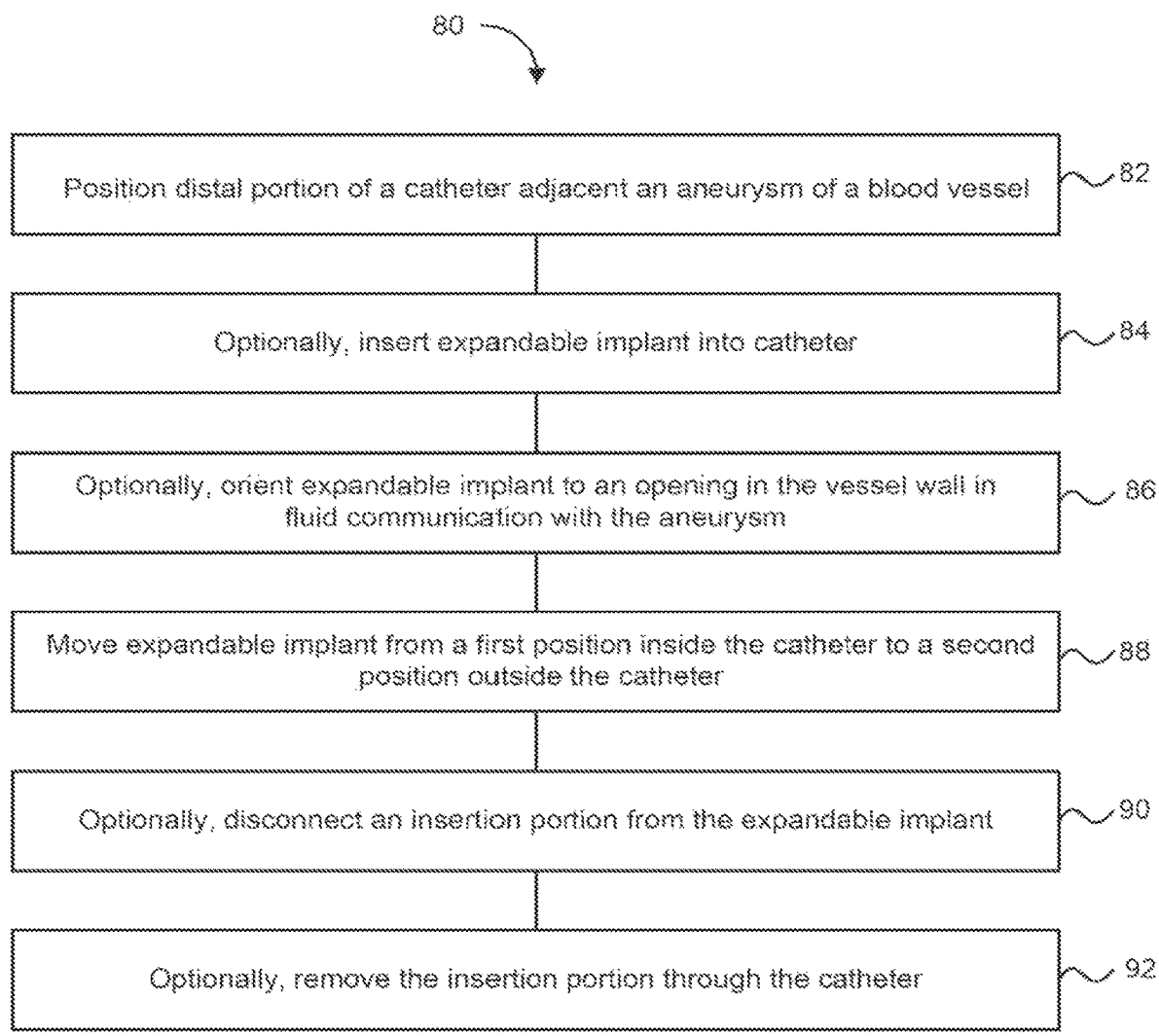
FIG. 18 is a flowchart of a method according to an embodiment.

FIG. 18 is a flowchart illustrating a method 80 of using a medical device to disrupt blood flow into an aneurysm and to promote healing of the aneurysm, as described herein, according to an embodiment. The method 80 includes at 82, positioning a catheter adjacent to an aneurysm of a blood vessel. For example, a distal portion of the catheter can be positioned adjacent an opening from the blood vessel into the aneurysm. The catheter defines an elongate lumen, which can be configured to receive at least a portion of the medical device for delivery to the aneurysm.

At 84, optionally, an expandable implant of the medical device is inserted into the catheter. The expandable implant includes a first portion and a second portion, each of which has a first (e.g., insertion or collapsed) configuration and a second (e.g., deployed or expanded) configuration. In the second configuration, the first portion substantially overlaps the second portion. Each of the first portion and the second portion also include a porous mesh. The porous mesh has a first porosity when in the first configuration and a second porosity when in the second configuration. The second porosity can be, for example, greater than the first porosity. The expandable implant can be biased in its second configuration before being inserted into the catheter. The expandable implant is in its first configuration when the expandable implant is disposed in the lumen of the catheter. The expandable implant can be inserted into the catheter after the catheter is positioned within the blood vessel, before the catheter is introduced into the blood vessel, or any time therebetween.

At 86, the expandable implant is optionally oriented to the opening in the vessel wall in fluid communication with the aneurysm. In this manner, the expandable implant is oriented to enter a sac of the aneurysm when the expandable implant is moved out of the catheter, as described in more detail herein.

At 88, the expandable implant is moved from a first position inside the catheter to a second position outside the catheter. For example, the expandable implant can be moved from a first position inside the lumen of the catheter to a second position in at least one of the blood vessel or the aneurysm outside of the catheter. As noted above, the expandable implant is in its first configuration when in its first position inside the catheter. The expandable implant is moved to its second configuration when in its second position outside of the constraint of the catheter. The second portion of the expandable implant can be moved to its second configuration before the first portion is moved to its second configuration. In their respective second configurations, the second portion can be disposed in an interior region defined by the first portion. For example, the second portion can be moved to its second configuration in which it has a multi-dimensional expanded shape, and then the first portion can be moved to its second configuration in which it curves into a multi-dimensional expanded shape around the second portion.

The medical device can include an insertion portion configured to move the expandable implant from its first position to its second position. The insertion portion can be, for example, a wire coupled to one of the first portion or the second portion of the expandable implant. At 90, the insertion portion is optionally disconnected from the expandable implant. For example, the insertion portion can be disconnected from a proximal end of the expandable implant, such as after the expandable implant has been inserted into the aneurysm. At 92, the insertion portion is optionally removed from the blood vessel through the catheter.

After the expandable implant is disposed within the aneurysm, or other target vascular defect, the portion of a patient's body including the aneurysm can be imaged (e.g., using X-ray or other suitable imaging techniques) to determine whether the expandable implant is properly positioned within the aneurysm. For example, the expandable implant can include one or more radiopaque markers that are visible using X-ray. In another example, the patient can be injected intravenously with a radiopaque dye at a desired time following implantation of the expandable implant to determine the success of endothelial cell attachment and/or healing over of the neck of the aneurysm following the procedure. If radiopaque dye is visible within the parent blood vessel adjacent the aneurysm, but not within the aneurysm itself, the expandable implant has operated to successfully prevent further blood flow into the aneurysm. If radiopaque dye is visible within the aneurysm, blood flow from the parent blood vessel has not been completely prevented and additional treatment options may be considered by the health care practitioner.

Figure 19B:
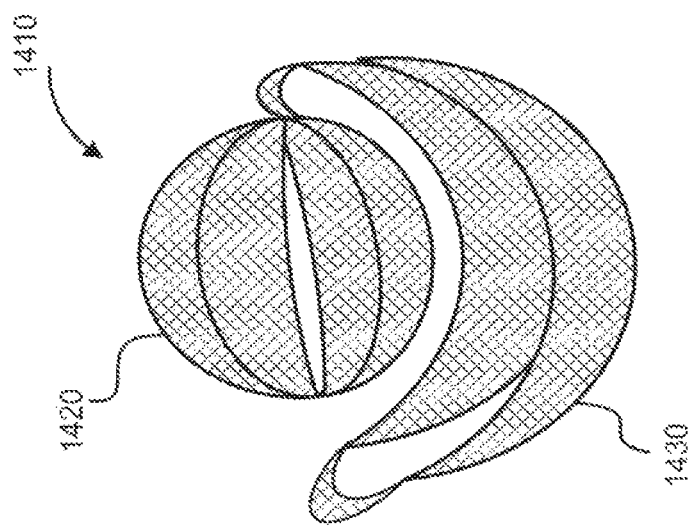
FIG. 19B is a schematic illustration of the medical device of FIG. 19A.
Figure 19A:
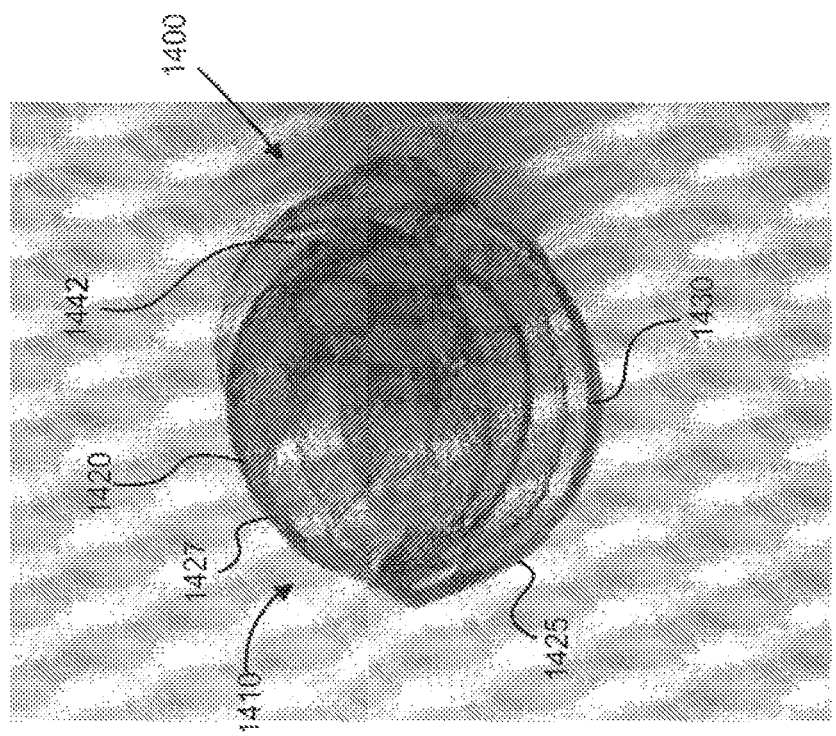
FIG. 19A is a view of a portion of a medical device in an expanded configuration, according to an embodiment.

FIG. 19A illustrates a portion of another embodiment of a medical device. The medical device 1400 can include the same or similar features and functions as described above for previous embodiments. For example, the medical device 1400 includes an expandable implant 1410 and an insertion portion or member (not shown in FIG. 19A). The expandable implant 1410 is shown in an expanded configuration and can be moved between a compressed or collapsed configuration in which the expandable implant 1410 is substantially elongate and the expanded configuration in the same or similar manner as described above for previous embodiments.

The expandable implant 1410 includes a ribbon-like strand of porous mesh and includes petal-like portions or sections 1425 and 1427 along its length. At least a portion of the porous mesh is configured to be positioned over a neck of an aneurysm when the expandable implant 1410 is in the expanded configuration. The expandable implant 1410 includes a first portion 1420 that includes the petal-like portions 1427 and a second portion 1430 that includes the petal-like portions 1427. The petal-like portions 1425 of the second portion 1430 are larger than the petal-like portions 1427 of the first portion 1420 such that when the expandable implant 1410 is moved to its expanded configuration, the petal-like portions 1425 of the second portion at least partially overlap the petal-like portions 1427 of the first portion 1420. During deployment of the expandable implant 1410 (e.g., when moved from its collapsed configuration to its expanded configuration) the petal-like portions 1425 of the second portion 1430 will deploy first, and then the petal-like portions 1427 of the first portion 1420 will deploy at least partially within an interior region defined by the second portion 1430. The petal-like portions 1425 of the second portion 1430 can be sized and configured to be disposed at a neck of an aneurysm when the expandable implant 1410 is in the expanded configuration. The petal-like portions 1427 of the first portion 1420 can be formed in a smaller diameter fixture than the petal-like portions 1425, and can be sized and configured to substantially fill the aneurysm and to hold the second portion 1430 in place at the neck of the aneurysm when the expandable implant 1410 is in the expanded configuration. For example, the petal-like portions 1427 of the first portion 1420 can have a diameter of about 2 mm-12 mm, and the petal-like portions 1425 of the second portion 1430 can have a corresponding diameter of about 1 mm larger than the petal-like portions 1427 of the first portion 1420. For example, the petal-like portions 1425 of the second portion 1430 can be about 3 mm-13 mm. FIG. 19B is a schematic illustration of the expandable implant 1410 in its expanded configuration showing the positional relationship of the first portion 1420 to the second portion 1430.

As described for previous embodiments, a first radiopaque marker 1442 is coupled to a first end of the expandable implant 1410 and a second radiopaque marker (not shown) is coupled to a second end of the expandable implant 1410. The expandable implant 1410 is configured to be wholly disposed within the aneurysm such that the radiopaque markers are wholly disposed within the aneurysm sac and the porous mesh is disposed over the neck of the aneurysm. In some embodiments, the radiopaque markers are configured to be positioned at a side of the aneurysm (i.e., disposed away from the neck of the aneurysm).

Figure 20:
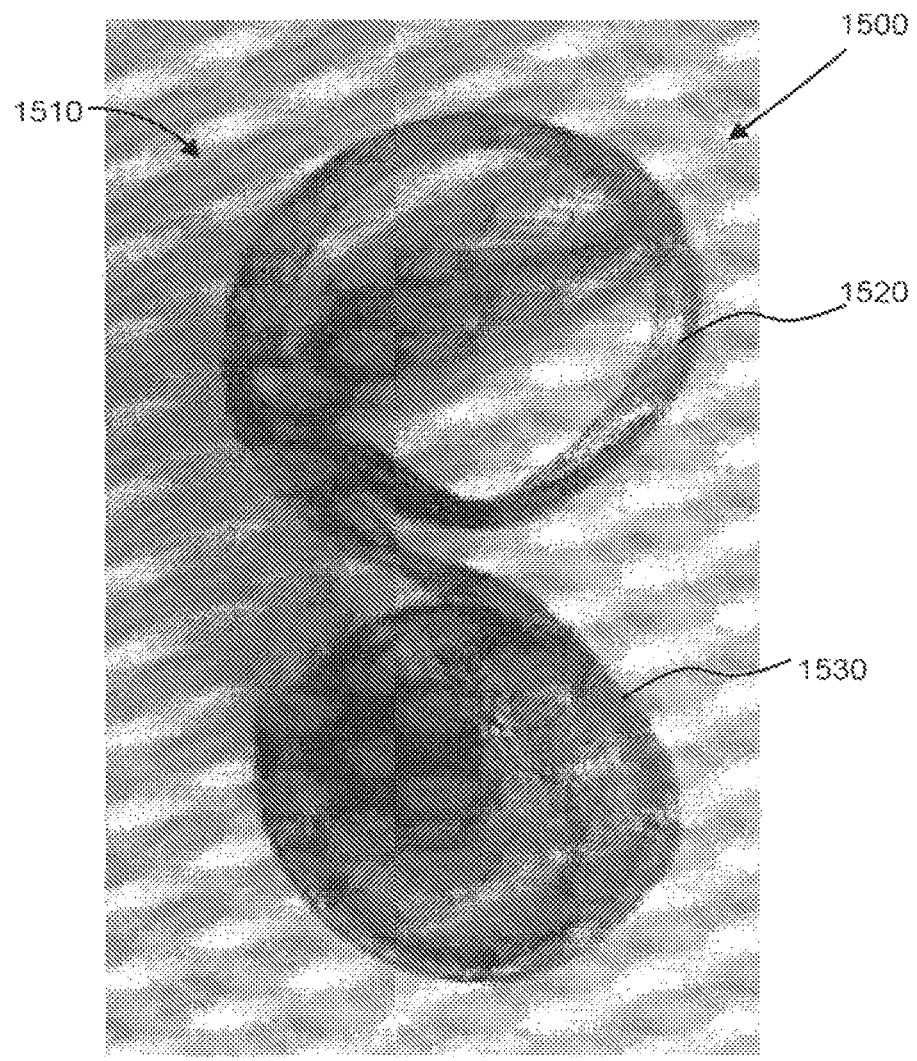
FIG. 20 is a view of a portion of a medical device in an expanded configuration, according to an embodiment.

FIG. 20 illustrates a portion of another embodiment of a medical device. The medical device 1500 can include the same or similar features and functions as described above for previous embodiments. For example, the medical device 1500 includes an expandable implant 1510 and an insertion portion or member (not shown in FIG. 20). The expandable implant 1510 is shown in an expanded configuration and can be moved between a compressed or collapsed configuration in which the expandable implant 1510 is substantially elongate and the expanded configuration in the same or similar manner as described above for previous embodiments.

As with the previous embodiment, the expandable implant 1510 includes a ribbon-like strand of porous mesh. At least a portion of the porous mesh is configured to be positioned over a neck of an aneurysm and at least another portion of the porous mesh substantially fills the volume of the aneurysm when the expandable implant 1510 is in the expanded configuration. The expandable implant 1510 includes a first portion 1520 and a second portion 1530. In this embodiment, each of the first portion 1520 and the second portion 1530 form a sphere when the expandable implant 1510 is in its expanded configuration. One of the first portion 1520 or the second portion 1530 can be configured to be disposed at a neck of the aneurysm and the other of the first portion 1520 or the second portion 1530 can substantially fill the volume of the aneurysm. For example, in this embodiment, the first portion 1520 can be configured to be deployed at the dome of an aneurysm and serve as an anchor for the second portion 1530 and the second portion 1530 can be disposed across the neck of the aneurysm when the expandable implant 1510 is in the expanded configuration. The expandable implant 1510 can also include radiopaque markers (not shown) as described above for previous embodiments.

Figure 21:
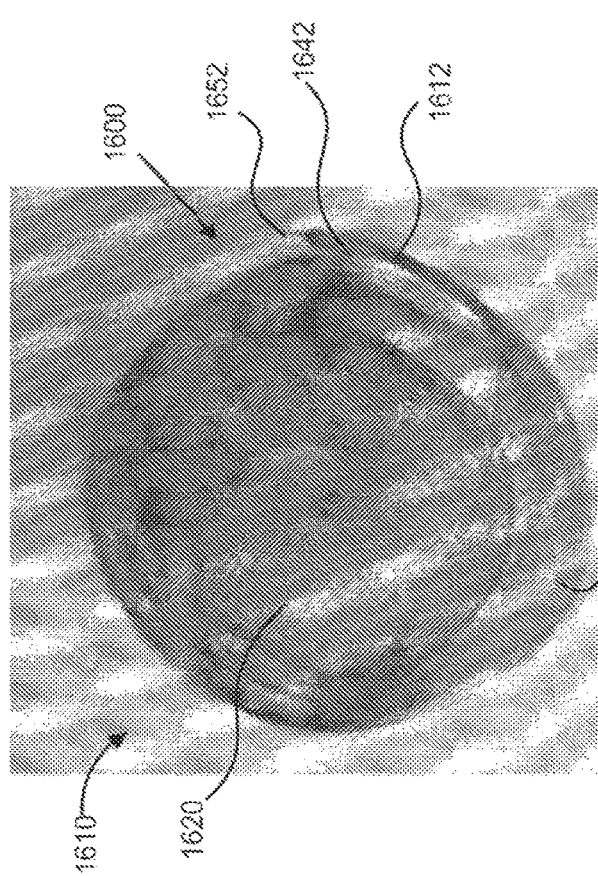
FIG. 21 is a view of a portion of a medical device in an expanded configuration, according to an embodiment.
Figure 22:
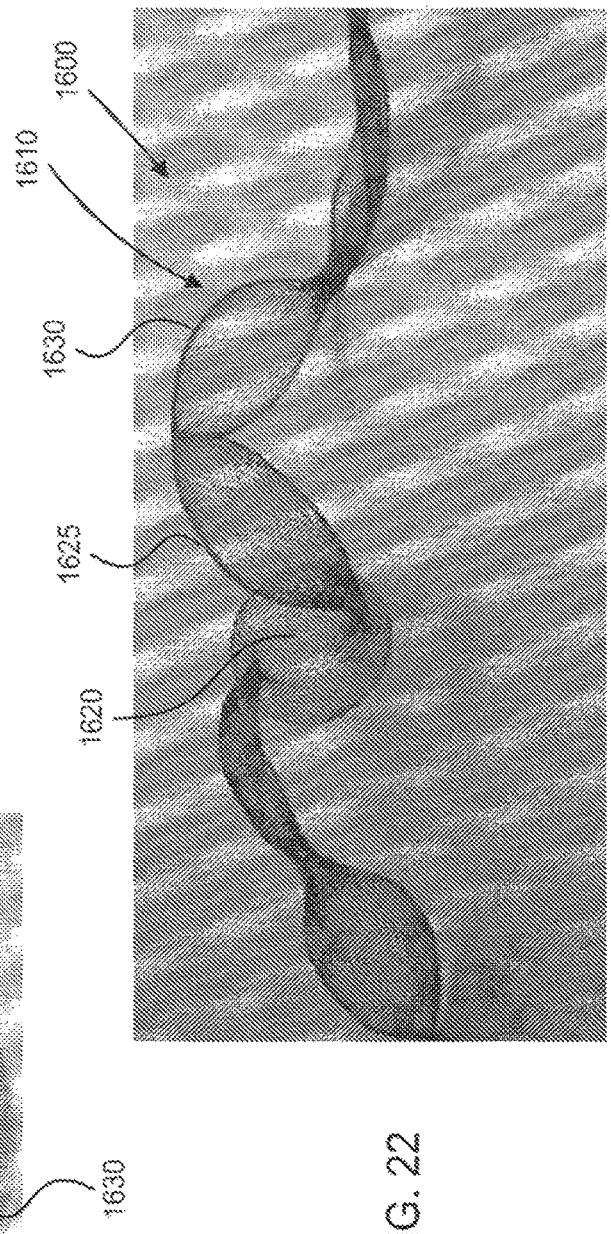
FIG. 22 is a view of a portion of the medical device of FIG. 21 in a collapsed configuration.

FIGS. 21 and 22 illustrate another embodiment of a medical device. The medical device 1600 can include the same or similar features and functions as described above for previous embodiments. For example, the medical device 1600 includes an expandable implant 1610 and an insertion portion or member (not shown). The expandable implant 1610 is shown in an expanded configuration and can be moved between a compressed or collapsed configuration as shown in FIG. 22 and the expanded configuration as shown in FIG. 21 in the same or similar manner as described above for previous embodiments.

As with the previous embodiment, the expandable implant 1610 includes a ribbon-like strand of porous mesh that includes a first portion 1620 in the form of a disc-shaped structure and a second portion 1630 that includes petal-like portions or sections along its length (similar to the embodiment of FIG. 19A). The disc or spherical shaped structure of the first portion 1620 can be disposed at various locations along the length (e.g., middle, end, etc.) of the expandable implant 1610. At least a portion of the porous mesh is configured to be positioned over a neck of an aneurysm when the expandable implant 1610 is in the expanded configuration. In this embodiment, when the expandable implant 1610 is in the expanded configuration, the petal-like portions of the second portion 1630 at least partially overlap the disc-shaped structure of the first portion 1620. For example, when the expandable implant 1610 is in its expanded configuration, the petal-like portions of the second portion 1630 can define a diameter greater than a diameter defined by the disc or spherical shaped structure of the first portion 1620. The expandable implant 1610 can also include a first radiopaque marker 1642 coupled to a first end 1612 of the expandable implant 1610 and a second radiopaque marker (not shown) coupled to a second end (not shown) of the expandable implant 1610. The expandable implant 1610 can also include a connector 1652 coupled to a first end 1612 of the expandable implant 1610.

When the expandable implant 1610 is in its expanded configuration, the expandable implant 1610 has a three-dimensional shape (e.g., a substantially spherical shape) with a substantially continuous outer surface such that edges of at least two of the petal-like portions 1625 overlap each other (in a similar manner as the embodiment of FIGS. 17A and 17B), and at least partially overlap the disc-shaped portion 1620. The expandable implant 1610 can move into the expanded configuration such that few or no openings or spaces remain between petal-like portions 1625 of the expandable implant 1610.

Figure 23:
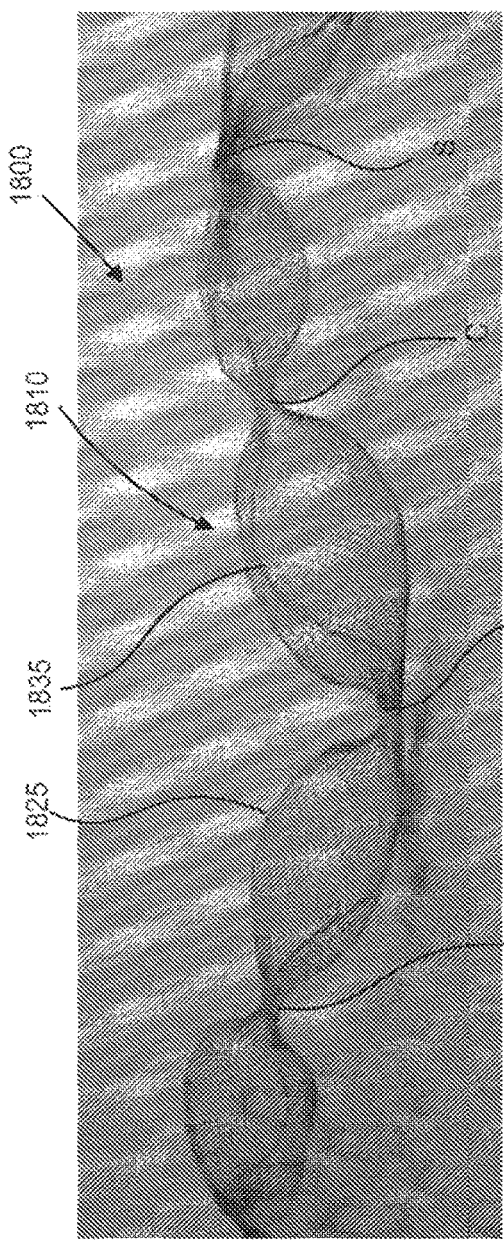
FIG. 23 is a view of a portion of a medical device in a collapsed configuration, according to another embodiment.
Figure 24:
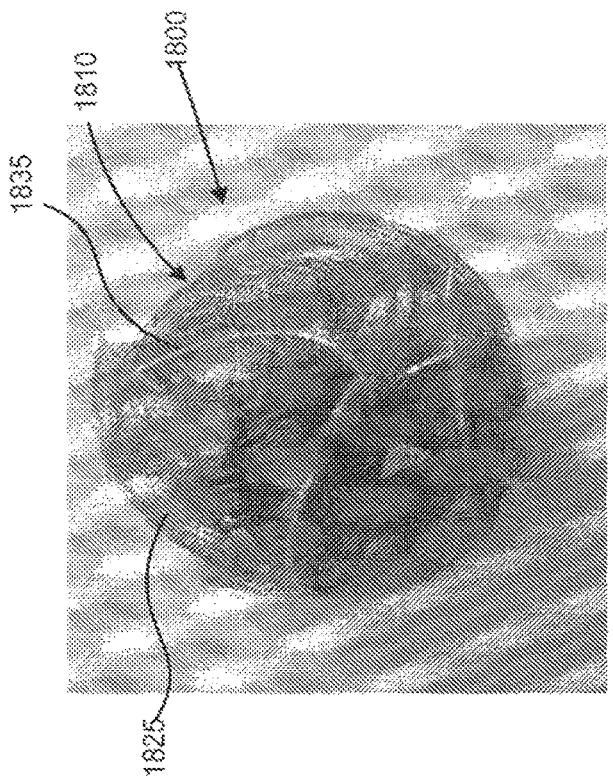
FIG. 24 is a view of the portion of the medical device. of FIG. 23 in an expanded configuration.

FIGS. 23 and 24 illustrate a portion of another embodiment of a medical device. The medical device 1800 can include the same or similar features and functions as described above for previous embodiments. For example, the medical device 1800 includes an expandable implant 1810 and an insertion portion or member (not shown in FIGS. 23 and 24). The expandable implant 1810 can be moved between a collapsed configuration as shown in FIG. 23 and an expanded configuration as shown in FIG. 24.

Similar to the embodiment of FIG. 19A, the expandable implant 1810 includes a ribbon-like strand of porous mesh that includes petal-like portions or sections 1825 along its length. At least a portion of the porous mesh is configured to be positioned over a neck of an aneurysm when the expandable implant 1810 is in the expanded configuration. When the expandable implant 1810 is in its expanded configuration, the expandable implant 1810 has a three-dimensional shape (e.g., a substantially spherical shape) with a substantially continuous outer surface such that edges of at least two of the petal-like portions 1825 overlap each other as shown in FIG. 24.

In this embodiment, when the implantable implant 1810 is formed, the ribbon-like strand of porous mesh is wrapped around the forming fixture in a multi-directional fashion. For example, a portion of the mesh can be wrapped in a continuous manner around the fixture as indicated at C in FIG. 23, and a portion of the mesh can be wrapped in an s-shape manner as indicated at S in FIG. 23. With such forming, when the expandable implant 1810 is moved to its expanded configuration, the petal-like portions 1825 that have been formed by wrapping in a continuous manner will follow each other (each petal-like portion 1825 will cause the adjacent petal-like portion 1825 to collapse), and the petal-like portions 1825 that have been formed in a s-shape manner will individually self-deploy or collapse. The multi-directional heat forming of the expandable implant 1810 can allow the expandable implant 1810 to deploy fragmented within an aneurysm.

In this embodiment, the medical device 1800 also includes a PT coil or PT strand 1835 disposed along the length of the expandable implant 1810 to provide for a portion of the expandable implant 1810 to be radiopaque. As shown in FIG. 23, the PT strand 1835 is disposed along a length of the expandable implant 1810 and across or within the petal-like portions 1825. The PT strand 1835 can be coupled to, for example, marker bands (not shown) disposed on a proximal end and a distal end of the expandable implant 1810. In some embodiments, a PT strand 1835 can be braided within the mesh of the expandable implant 1810.

In some embodiments, the PT strand 1835 can also be used to prevent over-stretching of the expandable implant 1810 when being delivered to a treatment site. For example, as described above, the PT strand 1835 can be coupled to the proximal end and the distal end of the expandable implant 1810. Thus, the PT strand 1835 can define a maximum length in which the expandable implant 1810 can be stretched or extended lengthwise during insertion and prevent overstretching. In alternative embodiments, a separate component can be used to limit the length of the expandable implant 1810. For example, in some embodiments, a separate wire member in addition to a PT strand can be used. In some embodiments, an expandable implant may not include a PT strand, such as PT strand 1835. In such embodiments, a separate wire member can be coupled to the proximal end and distal end of the expandable member and used to limit the length or amount of stretch of the expandable implant in a similar manner.

In some embodiments, a medical device can include a strand formed with, for example, a suture that extends along or within the medical device. The suture strand can reinforce the medical device along its length. In some embodiments, a radiopaque coil can be placed over the suture strand to enhance visibility of the medical device under fluoroscopy.

Figure 25:
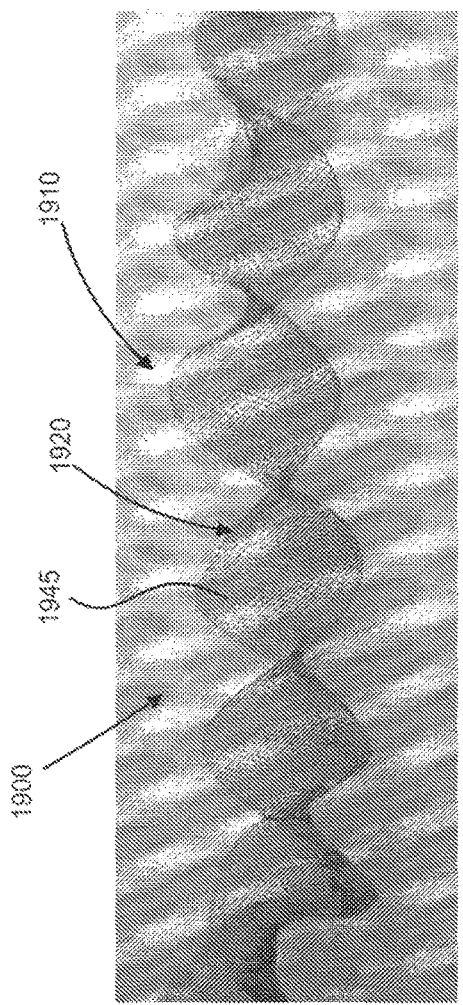
FIG. 25 is a view of a portion of a medical device in a collapsed configuration, according to an embodiment.
Figure 26:
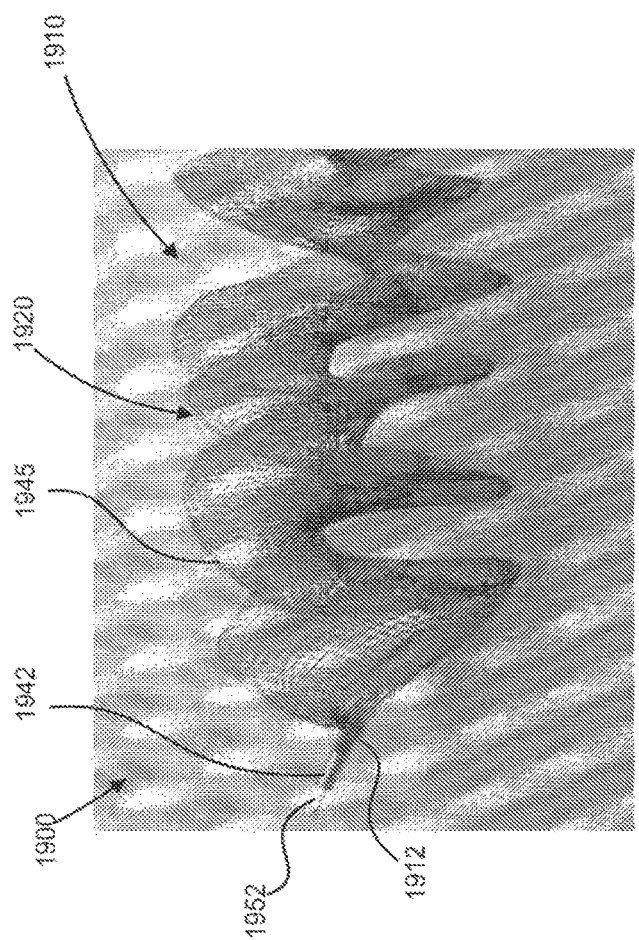
FIG. 26 is a view of the portion of the medical device of FIG. 25 in a partially expanded configuration.
Figure 27:
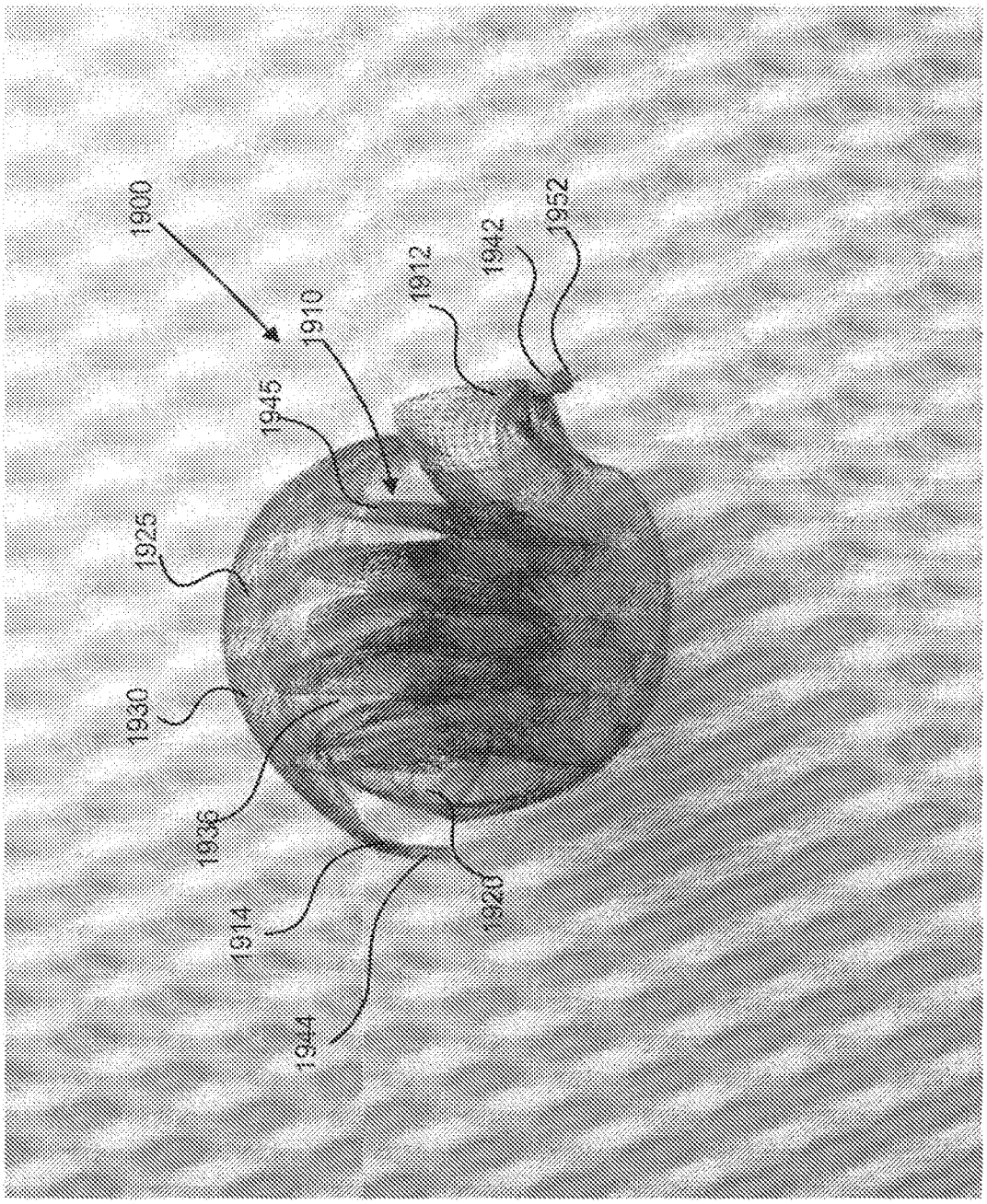
FIG. 27 is a view of a portion of the medical device of FIG. 25 in an expanded configuration.

FIGS. 25-27 illustrate a portion of another embodiment of a medical device. The medical device 1900 can include the same or similar features and functions as described above for previous embodiments. For example, the medical device 1900 includes an expandable implant 1910 and an insertion portion or member (not shown in FIGS. 25-27). The expandable implant 1910 can be moved between a collapsed configuration (as shown in FIG. 25, a partially expanded configuration as shown in FIG. 26, and an expanded configuration as shown in FIG. 27.

The expandable implant 1910 includes a ribbon-like strand of porous mesh that includes a first portion 1920 (see FIGS. 25-27) and a second portion 1930 (shown only in FIG. 27). In this embodiment, the first portion 1920 and the second portion 1930 are separate components that can be deployed together. The first portion 1920 includes disc-shaped portions 1945 along its length, and the second portion 1930 includes petal-like portions 1925, as described above for previous embodiments. When the expandable implant 1910 is in its expanded configuration, the expandable implant 1910 has a three-dimensional shape (e.g., a substantially spherical shape) as shown in FIG. 27.

During deployment of the medical device 1900, the second portion 1930 can be deployed first such that the petal-like portions 1925 are moved to an expanded configuration and define an interior region 1936. The first portion 1920 can then be deployed such that the disc-shape portions 1945 will collapse upon each other (as shown in FIGS. 26 and 27) within the interior region 1936 of the second portion 1930, as shown in FIG. 27. In other words, when the expandable implant 1910 is in the expanded configuration, the second portion 1930 at least partially overlaps the first portion 1920, as shown in FIG. 27. At least a portion of the porous mesh is configured to be positioned over a neck of an aneurysm when the expandable implant 1910 is in the expanded configuration. For example, when the expandable implant 1910 is in its expanded configuration, the second portion 1930 can be disposed at the neck of the aneurysm to disrupt blood flow, and the first portion 1920 can help occlude the aneurysm at a relatively fast rate. Although this embodiment illustrates the first portion 1920 and the second portion 1930 as separate components, in an alternative embodiment, the first portion 1920 and the second portion 1930 can be formed with a single mesh component.

In this embodiment, the medical device 1900 can also include a PT coil or PT strand (not shown) disposed along the length of first portion 1920 and/or the second portion 1930 of the expandable implant 1910 in a similar manner as described above for medical device 1800. The PT strand can be coupled to a first marker band 1942 disposed at a first end 1912 of the expandable implant 1910 and a second marker band 1944 disposed on a second end of the expandable implant 1910 as shown in FIG. 27. As described above, the PT strand can be braided within the mesh of the expandable implant 1910. As shown in FIGS. 26 and 27, the expandable member 1910 also includes a connector member 1952 that can be used to couple the expandable member 1910 to a detachment device as described in more detail below (see e.g., discussion of FIG. 40).

Figure 28:
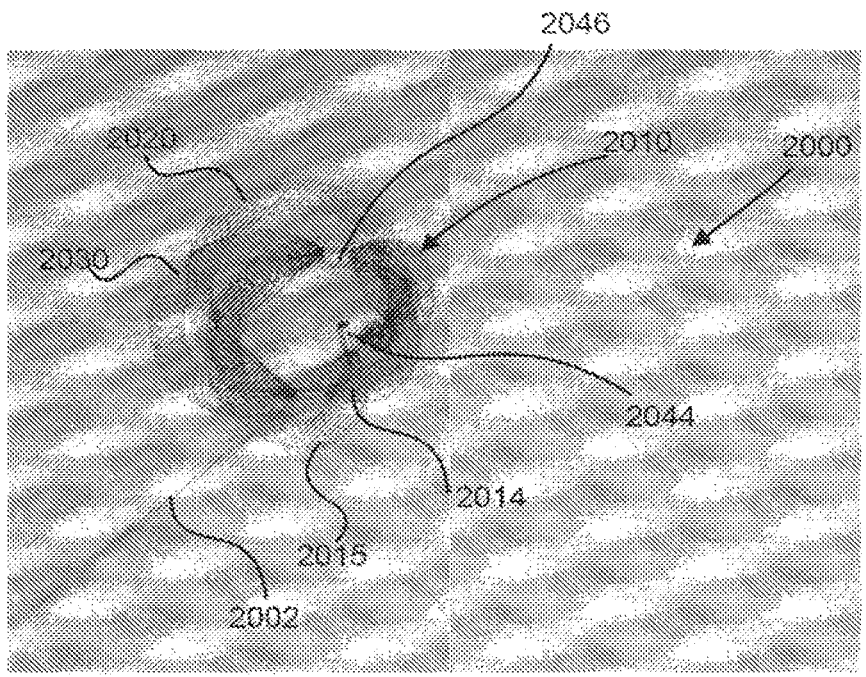
FIGS. 28 and 29 are each a different view of a portion of a medical device in an expanded configuration, according to an embodiment.
Figure 29:
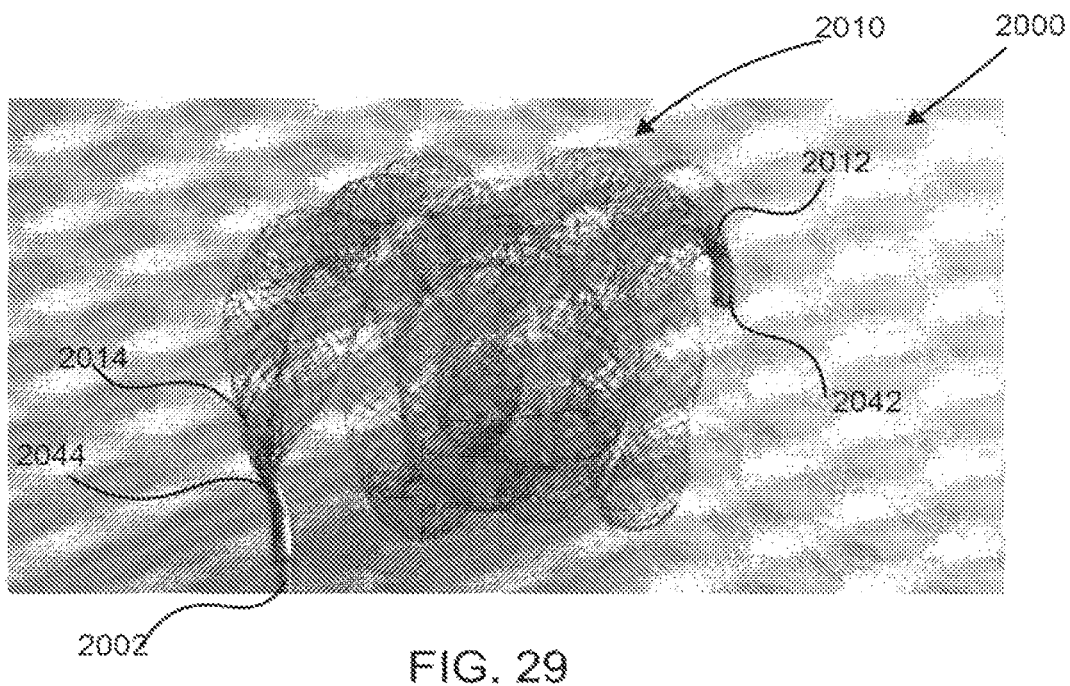

FIGS. 28 and 29 illustrate another embodiment of a medical device. A medical device 2000 can include all the same or similar features and functions as described above for previous embodiments. For example, the medical device 2000 includes an expandable implant 2010, an insertion portion or member 2002, a first radiopaque marker 2042 coupled to a first end 2012 of the expandable implant 2010 and a second radiopaque marker 2044 coupled to a second end 2014 of the expandable implant 2010. The expandable implant 2010 can be moved between a collapsed configuration (not shown) and an expanded configuration as shown in FIGS. 28 and 29.

In this embodiment, the expandable implant 2010 includes three tubular or rounded strands 2020, 2030 and 2015 formed of a porous mesh similar to the tubular structures described above, for example, with respect to FIGS. 10 and 11. In some embodiments, the strands 2020, 2030 and 2015 can be braided. In alternative embodiments, the strands 2020, 2030 and 2015 can be formed with ribbon-like strands of porous mesh rather than tubular strands. When the expandable implant 2010 is in its expanded configuration, at least a portion of the tubular strands 2020, 2030 and 2015 can overlap each other as shown in FIG. 29. The expandable implant 2010 can be used to fill a volume of an aneurysm and can be used alone or in conjunction with another expandable implant to fill the volume of an aneurysm.

The tubular mesh can be, for example, 1 mm tubular mesh. In this embodiment, the tubular strands 2020, 2030, 2015 can be heat-shaped such that the expandable implant 2010 has a 2D configuration when the expandable implant 2010 is in its expanded configuration. In this embodiment, three tubular strands are included, but in alternative embodiments a different number of tubular strands can be included. For example, an expandable implant can be formed with 1-10 tubular strands. The tubular strands 2020, 2030 and 2015 can be coupled together at various locations along their lengths with marker bands, such as marker band 2046 shown in FIG. 29. In alternative embodiments, the tubular strands can be twisted together, or braided together rather than using marker bands. In some embodiments, the strands are not coupled together.

Figure 30:
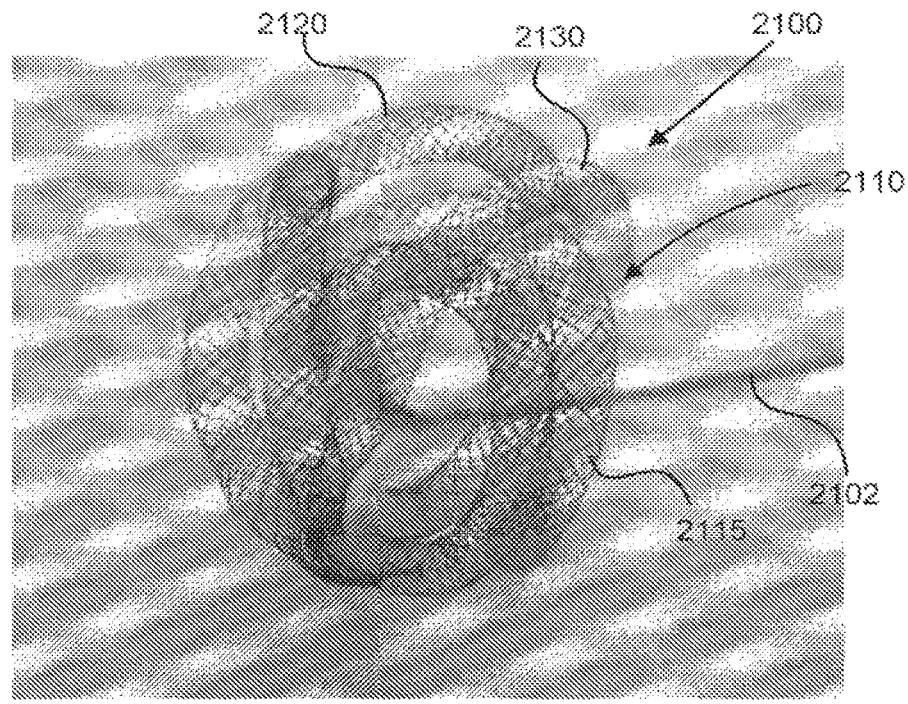
FIGS. 30 and 31 are each a view of a portion of a medical device in an expanded configuration, according to different embodiments.

FIG. 30 illustrates another embodiment of a medical device including tubular structures. A medical device 2100 can include all the same or similar features and functions as described above for previous embodiments. For example, the medical device 2100 includes an expandable implant 2110 and an insertion portion or member 2102. Although not shown in FIG. 30, the medical device 2100 can also include radiopaque markers coupled to end portions to the expandable implant 2110. The expandable implant 2110 can be moved between a collapsed configuration (not shown) and an expanded configuration as shown in FIG. 30.

The expandable implant 2110 includes three tubular or rounded strands 2120, 2130 and 2115 formed of a porous mesh similar to the tubular strands described above for medical device 2000. When the expandable implant 2110 is in its expanded configuration, at least a portion of the tubular strands 2120, 2130 and 2115 can overlap each other as shown in FIG. 30. In this embodiment, the tubular strands 2120, 2130, 2115 can be heat-shaped to have a 3D configuration when the expandable implant 2110 is in the expanded configuration. In this embodiment, three tubular strands are included, but in alternative embodiments a different number of tubular strands can be included. For example, an expandable implant can be formed with 1-10 tubular strands. The tubular strands 2120, 2130 and 2115 can be coupled together at various locations along their lengths with marker bands (not shown) as described above for medical device 2000, or can be coupled using other coupling methods, such as being twisted together, or braided together. In some embodiments, the tubular strands are not coupled together.

Figure 31:
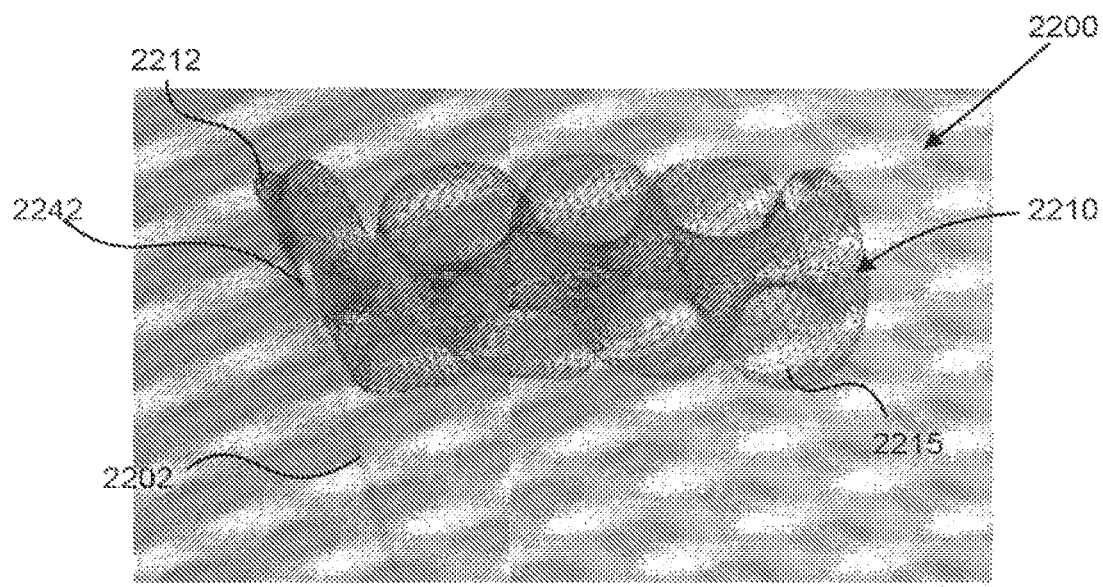

FIG. 31 illustrates another embodiment of a medical device including tubular structures. A medical device 2200 can include all the same or similar features and functions as described above for previous embodiments. For example, the medical device 2200 includes an expandable implant 2210 and an insertion portion or member 2202. Although not shown in FIG. 31, the medical device 2200 can also include radiopaque markers coupled to end portions to the expandable implant 2210, such as radiopaque marker 2242 coupled to an end 2212 shown in FIG. 31. The expandable implant 2210 can be moved between a collapsed configuration (not shown) and an expanded configuration as shown in FIG. 31.

In this embodiment, the expandable implant 2210 includes a single tubular or rounded braid structure 2215 formed of a porous mesh similar to the tubular structures described above for medical devices 2000 and 2100. When the expandable implant 2210 is in its expanded configuration, at least a first portion of the tubular structure 2215 can overlap a second portion of the tubular structure 2215, as shown in FIG. 31. In this embodiment, the tubular structure 2215 is formed in a 2D shape configuration and the tubular structure is formed with a larger porosity mesh than medical devices 2000 and 2100. For example, the tubular structure 2215 can be formed with a 3 mm mesh.

Figure 32:
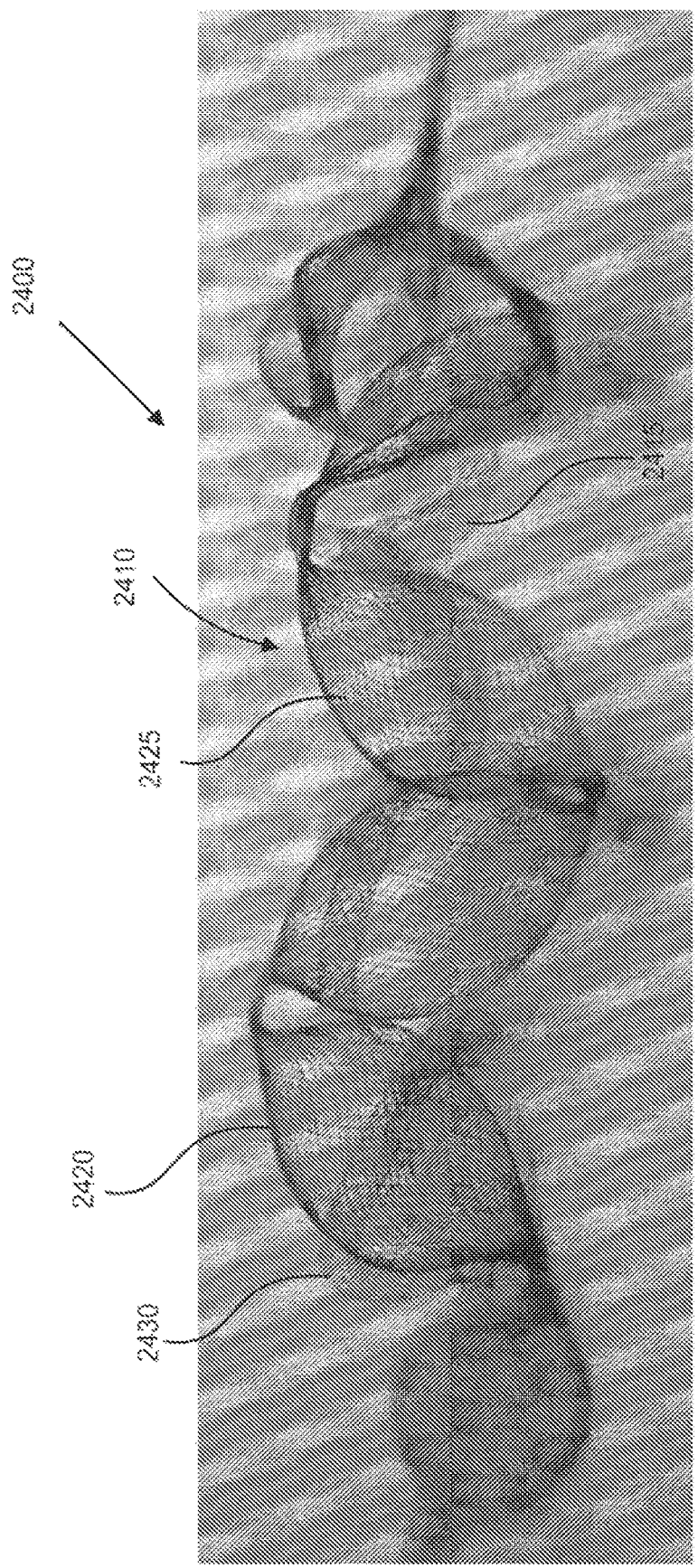
FIG. 32 is a view of a portion of a medical device in a collapsed configuration, according to an embodiment.
Figure 33:
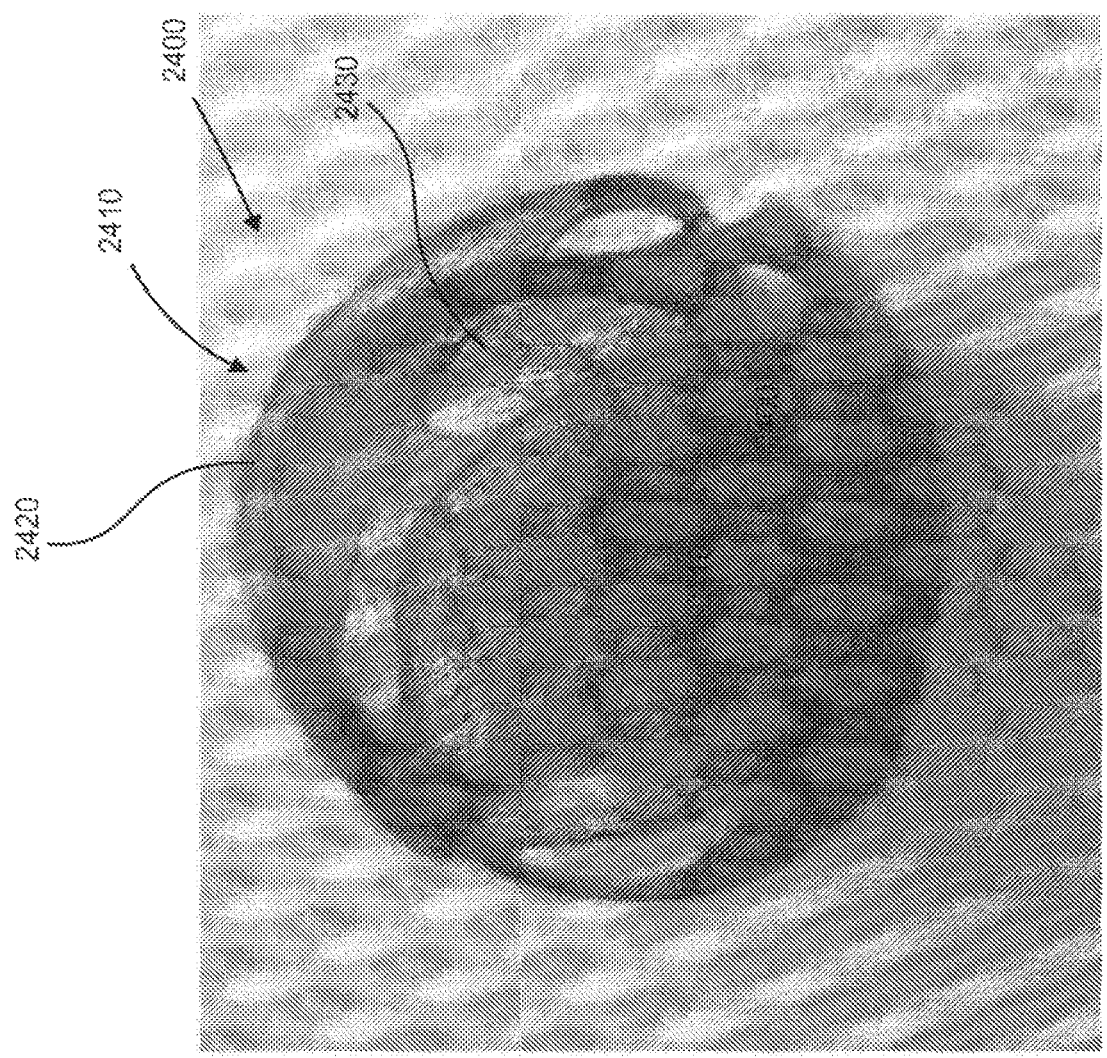
FIG. 33 is a view of the portion of the medical device of FIG. 32, shown in an expanded configuration.

FIGS. 32-33 illustrate a portion of another embodiment of a medical device. The medical device 2400 can include the same or similar features and functions as described above for previous embodiments. The medical device 2400 includes an expandable implant 2410 and can include an insertion portion or member (not shown in FIGS. 32-33). The expandable implant 2410 can be moved between a collapsed configuration as shown in FIG. 32 and an expanded configuration as shown in FIG. 33.

In this embodiment, the expandable implant 2410 includes a first portion 2420 formed with a ribbon-like strand of porous mesh and includes petal-like portions 2425, and a second portion 2430 in the form of a tubular or rounded strand 2415 formed of a porous mesh similar to the tubular strands described above, for example, with respect to FIGS. 28-30. The tubular strand 2415 can be heat formed as either a 2D or 3D configuration. In some embodiments, the tubular strand 2415 can be braided.

When the expandable implant 2410 is in its expanded configuration, at least a portion of the first portion 2420 (e.g., petal-like portions 2425) can overlap the tubular strand 2415 of the second portion 2430. At least a portion of the expandable implant 2410 is configured to be positioned over a neck of an aneurysm when the expandable implant 2410 is in the expanded configuration. The petal-like portions 2425 and the tubular strand 2415 can each be a variety of different sizes (e.g., diameters), such that when the expandable implant 2410 is moved to its expanded configuration, the petal-like portions 2425 of the second portion 2410 define an interior region and the tubular strand 2415 of the first portion 2420 substantially fills the interior region of the second portion 2430. Thus, the tubular strand 2415 can be used as a filler to substantially fill a volume of an aneurysm as described above for expandable implants 2010 and 2110.

The first portion 2420 and the second portion 2430 can be coupled together, for example, with marker bands at end portions of the first portion 2420 and the second portion 2430 and/or at other locations along a length of each of the first portion 2420 and the second portion 2430. The first portion 2420 and the second portion 2430 can have the same or substantially the same length or can have different lengths. For example, in some embodiments, the second portion 2430 can be longer than the first portion and vice versa.

Figure 34:
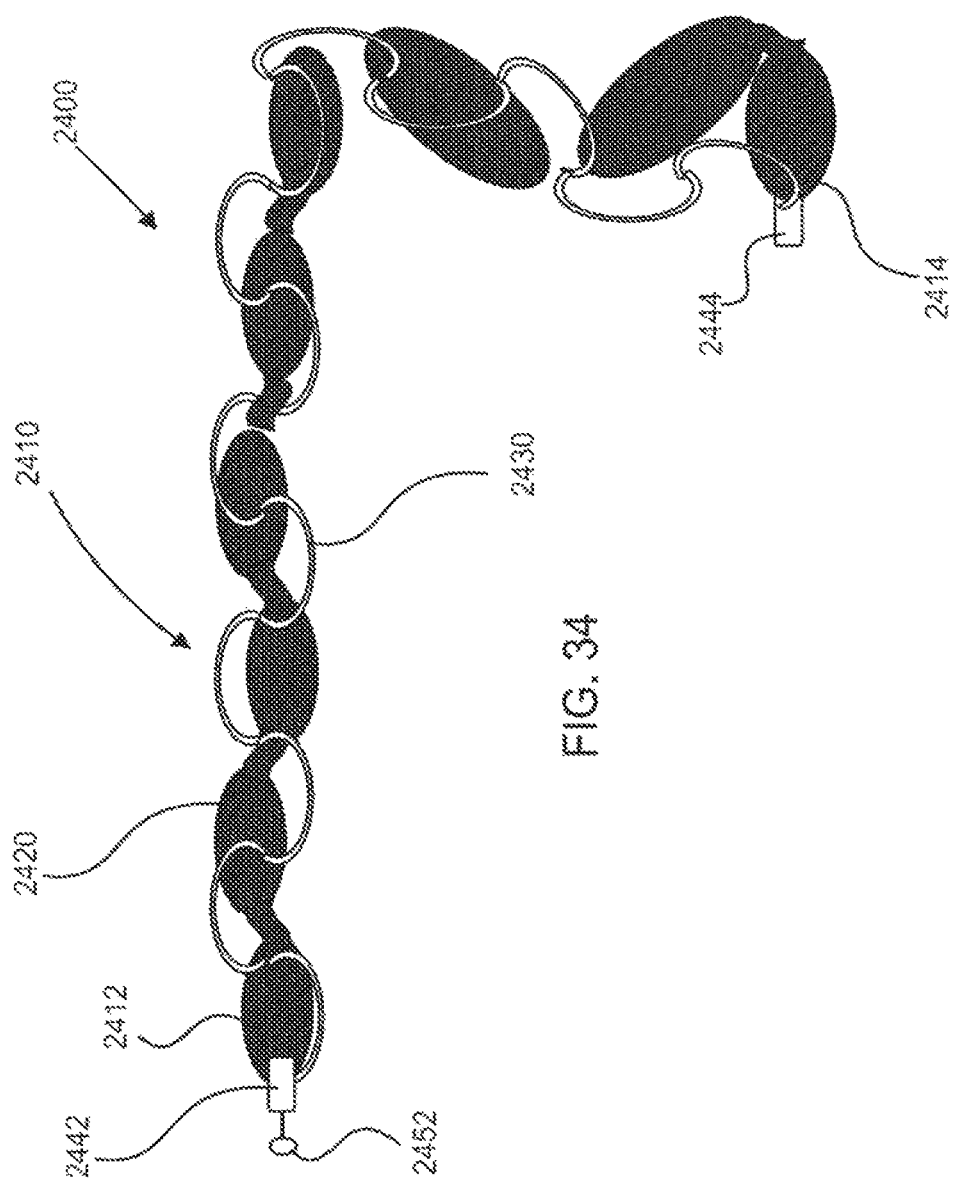
FIG. 34 is a schematic illustration of the portion of the medical device of FIG. 33.

The expandable implant 2410 also includes a first radiopaque marker band 2442 disposed at a first end 2412 of the expandable member and a second radiopaque marker band 2444 disposed at a second end 2414 of the expandable implant 2410 as shown in FIG. 35, which is a schematic illustration of the expandable implant 2410. As shown in FIG. 34, which is a schematic illustration of the expandable implant 2410, the expandable member 2410 also includes a connector member 2452 that can be used to couple the expandable member to a detachment device as described in more detail below.

Figure 37:
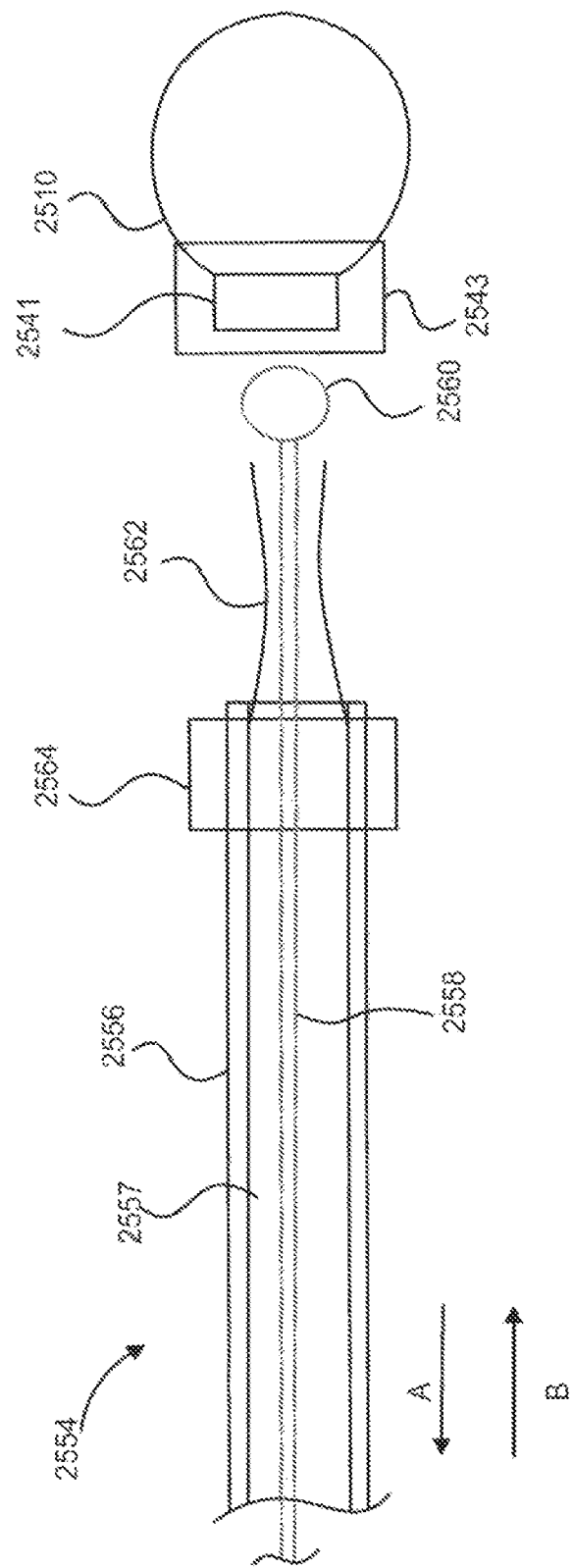
FIG. 37 is a schematic illustration of the portion of the insertion device of FIG. 35 shown removed from the expandable implant.

FIGS. 35-37 are each a schematic illustration of an insertion device that can be used to insert and deploy an implant, such as an expandable implant as described herein, at a desired location within a patient's body (e.g., within an aneurysm). An insertion device 2554 can be used in conjunction with a cannula, such as, for example, the cannula 104 described herein. For example, the insertion device 2254 can be used instead of the insertion portion 102 described herein and can be releasably or removably coupled to an implant as described in more detail below.

The insertion device 2554 includes a first elongate member 2556 defining a lumen 2557 through which a second elongate member 2558 can be movably disposed. A marker band 2564 is coupled to a distal end portion of the first elongate member 2556. An expandable coupling member 2562 is also coupled to the distal end portion of the first elongate member 2556, for example, by adhesively coupling a portion of the expandable coupling member 2562 between the marker band 2564 and an outer wall of the first elongate member 2556. The expandable coupling member 2562 can be various lengths and can in some embodiments have a length, for example, of about 1-2 mm. The expandable coupling member 2562 can be formed, for example, with a mesh material and/or a braided material.

The second elongate member 2558 can be, for example, a core wire and includes a ball member 2560 (also referred to as a "coupling member") disposed at a distal end of the second elongate member 2558. The second elongate member 2558 can be moved between a first position in which the ball member 2560 is disposed outside of the expandable coupling member 2562 as shown in FIGS. 35 and 37, and a second position in which the ball member 2560 is disposed within an interior region defined by the expandable coupling member 2562 as shown in FIG. 36. Although the ball member 2560 is shown circular shaped, in alternative embodiments, the ball member 2560 can be other shapes, such as, for example, oval, elliptical, square, rectangular, triangular or other desired shapes (as shown in a side view).

To insert and deploy an expandable implant (e.g., an expandable implant as described herein) within a patient's body, a proximal end portion of the expandable implant can be coupled to a distal end portion of the insertion device 2554. Specifically, as shown in FIG. 35, an expandable implant 2510 (also referred to as "implant") can include an outer marker band 2543 and an inner marker band 2541 each coupled to a proximal end portion 2512 of the implant 2510. The outer marker band 2543 can be used to hold the implant 2510, and the inner marker band 2541 can be disposed within the outer marker band 2543. The inner marker band 2541 can provide a channel through which a distal end portion of the insertion device 2554, including the expandable coupling member 2562 and the ball member 2560, can be inserted. The second elongate member 2558 is then pulled proximally (in a direction of arrow A in FIG. 36) causing the ball member 2560 to become wedged within the expandable coupling member 2562 as shown in FIG. 36. For example, the expandable coupling member 2562 can be moved between collapsed or relaxed configuration as shown in FIG. 35 to an expanded configuration as shown in FIG. 36 in which the expandable coupling member 2562 flexes outward or expands as the ball member 2560 is moved proximally within the expandable coupling member 2562. A locking mechanism (not shown) can be used to lock the second elongate member 2558 in position relative to the first elongate member 2556. For example, a handle (not shown) can be coupled to the second elongate member 2558 and can include a locking mechanism that can lock the second elongate member 2558 in the position shown in FIG. 36. With the expandable coupling member 2562 expanded as shown in FIG. 36, the implant 2510 is maintained coupled to the insertion device 2554.

With the insertion device 2554 coupled to the implant 2510, a distal end portion of the implant 2510 can be inserted into, for example, an insertion cannula or catheter (not shown) (e.g., cannula 102 described above), and the insertion cannula can be used to insert the implant 2510 into a blood vessel in a similar manner as described above with respect to FIGS. 1 and 2. For example, the implant 2510 with the insertion device 2554 coupled thereto can be inserted into the insertion cannula such that the implant 2510 is moved into a collapsed configuration. The insertion cannula can then be inserted into a blood vessel of the patient to deliver the implant 2510 to a desired location (e.g., an aneurysm) within the patient. At the desired location, the implant 2510 can be moved out of a distal end of the cannula and moved to its expanded configuration as described above. After the implant 2510 has been deployed, the implant 2510 can be detached from the insertion device 2554. Specifically, to detach the insertion device 2554 from the implant 2510, the second elongate member 2558 is unlocked and moved distally (in a direction of arrow B shown in FIG. 37) such that the ball member 2560 is moved distally outside the expandable coupling member 2562 allowing the expandable coupling member 2562 to move back to its collapsed or relaxed configuration as shown in FIG. 37. The insertion device 2554 can then be removed by pulling the insertion device 2554 proximally (in a direction of arrow A in FIG. 37).

Figure 38:
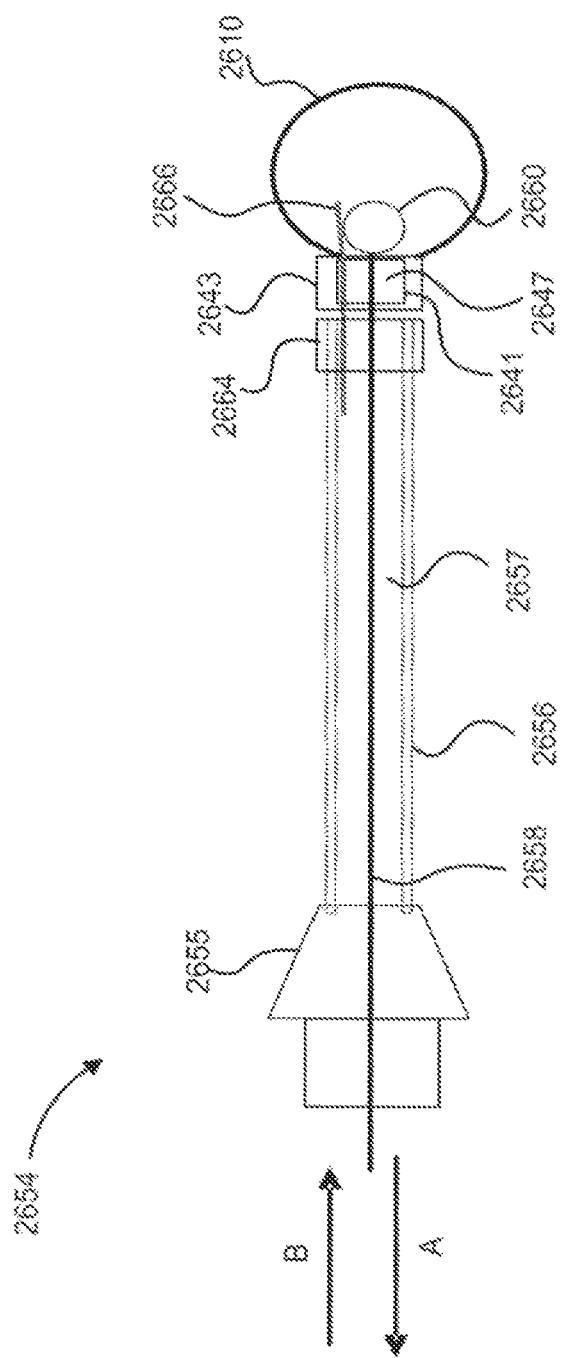
FIG. 38 is a schematic illustration of a portion of an insertion device, according to another embodiment.

FIG. 38 is a schematic illustration of another embodiment of an insertion device that can be used to insert and deploy an implant, such as an expandable implant 2610 as described herein. An insertion device 2654 can be used in conjunction with a cannula and can be releasably or removably coupled to an implant, as described above for insertion device 2554.

The insertion device 2654 includes a first elongate member 2656 defining a lumen 2657 through which a second elongate member 2658 can be movably disposed. A coupling element 2666 is coupled to a distal end portion of the first elongate member 2656, for example, by gluing a portion of the coupling element 2666 to an interior wall of the first elongate member 2656. The coupling element 2666 can include, for example, a length of suture material, and can be various lengths. For example, the coupling element 2666 can in some embodiments have a length of about 1-2 mm. The first elongate member 2656 can also include a marker band 2664 similar to the marker band 2564 that can be coupled to a distal end portion of the first elongate member 2656.

The second elongate member 2658 includes a ball member 2660 disposed at a distal end of the second elongate member 2658 and can be moved between a first position in which the ball member 2660 is disposed at a distance from the coupling element 2666 (e.g., at a position distal of the coupling element 2666), and a second position in which the ball member 2660 is disposed in contact with the coupling element 2666. For example, when the second elongate member 2658 is in its second position, the ball member 2660 is disposed at a location along a length of the coupling element 2666 and contacting the coupling element 2666 such that an interference fit is created between the ball member 2660 and the coupling element 2666 as shown in FIG. 38.

To insert and deploy an expandable implant, such as the expandable implants 2610 described herein, within a patient's body, a proximal end portion of the expandable implant 2610 (also referred to as "implant") can be coupled to a distal end portion of the insertion device 2654 Specifically, the implant 2610 can include an outer marker band 2643 and an inner marker band 2641 each coupled to a proximal end portion of the implant 2610. As with the previous embodiment, the outer marker band 2643 can be used to hold the implant 2610 and the inner marker band 2641 can be disposed within the outer marker band 2643 and provide a channel 2647 through which the distal end portion of the insertion device 2654 can be inserted.

With the second elongate member 2658 in its first position (i.e., with the ball member 2660 disposed at a distance from the coupling element 2666) and the coupling element 2666 in its first configuration, the ball member 2660 and the coupling element 2666 are inserted through the inner marker band 2641 and disposed within the implant 2610. The second elongate member 2658 is then pulled proximally (in the direction of arrow A in FIG. 38) such that the second elongate member 2658 is moved to its second position (with the ball member 2660 contacting the coupling element 2666) and the coupling element 2666 is moved to a second configuration as shown in FIG. 38. When the second elongate member 2658 is in its second position and the coupling element 2666 is in its second configuration an interference fit is created between the ball member 2660 and the coupling element 2666. This interference fit holds the implant 2610 to the insertion device 2654. As described above for the previous embodiment, a locking mechanism (not shown) can be used to lock the second elongate member 2658 in position relative to the first elongate member 2656. For example, a handle 2655 is coupled to the second elongate member 2658 and can include a locking mechanism (not shown) that can lock the second elongate member 2658 in its second position, as shown in FIG. 38.

With the insertion device 2654 coupled to the implant 2610, a distal end portion (not shown) of the implant 2610 can be inserted into, for example, an insertion cannula (not shown) (e.g., cannula 102 described above), and the insertion cannula can be used to insert the implant 2610 into a blood vessel in a similar manner as described above with respect to FIGS. 1 and 2 and FIGS. 35-37. For example, the implant 2610 with the insertion device 2654 coupled thereto can be pushed distally within the cannula to move the implant 2610 to a collapsed configuration. The cannula can then be inserted into a blood vessel of the patient to deliver the implant 2610 to a desired location within the patient, such as, for example, within an aneurysm, as described above. After the implant 2610 has been deployed (e.g., moved out of a distal end of the cannula), the insertion device 2654 can be detached from the implant 2610 in a similar manner as described above for the previous embodiment. Specifically, to detach the insertion device 2654 from the implant 2610, the second elongate member 2658 is unlocked and moved distally (in the direction of arrow B in FIG. 38) such that the ball member 2660 is moved away (e.g., distally) from the coupling element 2666, eliminating the interference fit between the ball member 2660 and the coupling element 2666. The insertion device 2654 can then be removed by pulling the insertion device 2654 proximally (in a direction of arrow A in FIG. 38).

Figure 39:
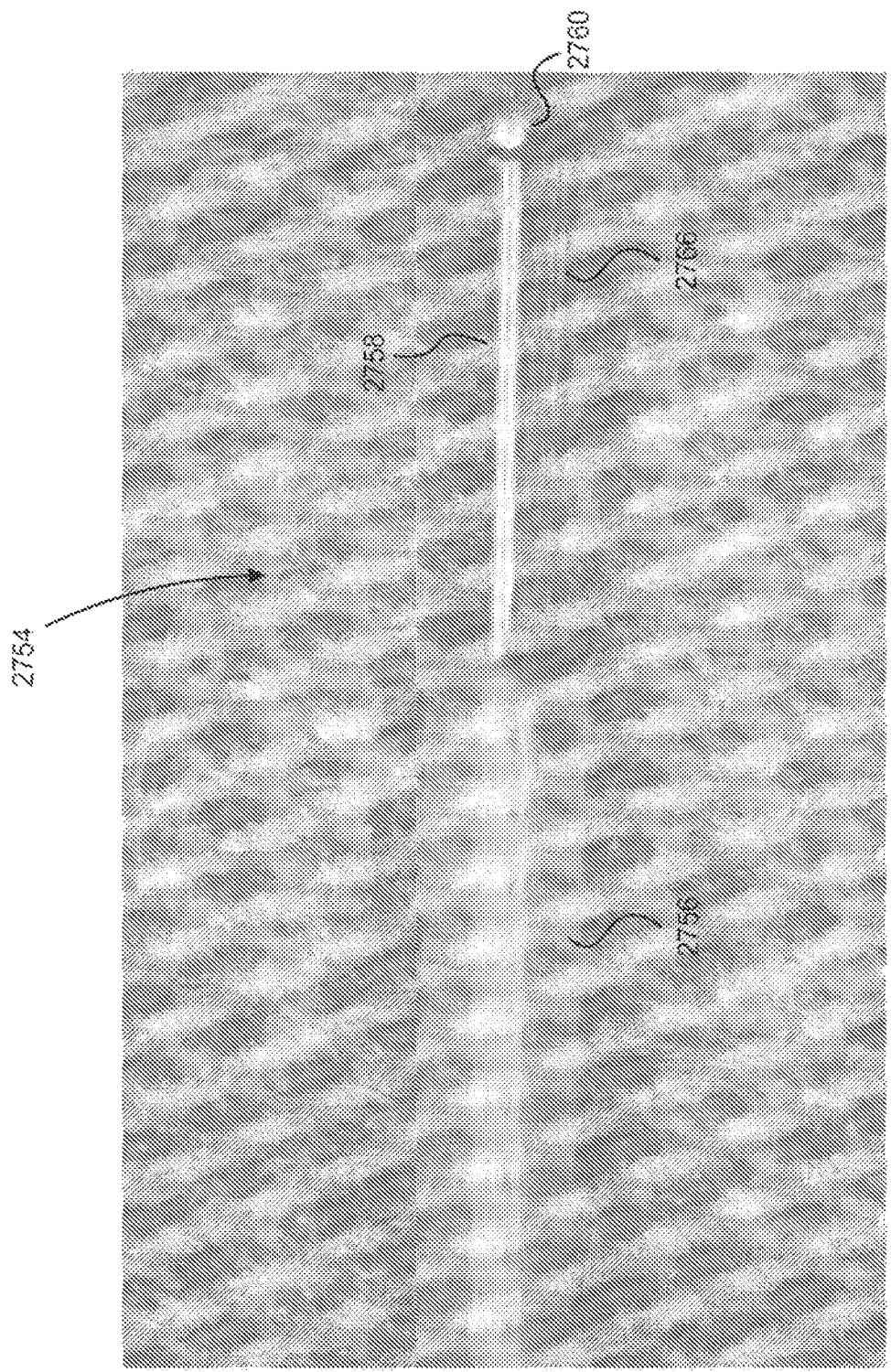
FIG. 39 is a view of a portion of an insertion device, according to another embodiment.

FIG. 39 illustrates an embodiment of an insertion device 2754 that is similar to the insertion device 2654. The insertion device 2754 can include the same as or similar features and function the same as or similar to the insertion device 2654. For example the insertion device 2754 can be used in the deployment of an implant as described above. The insertion device 2754 includes a first elongate member 2756 defining a lumen (not shown) through which a second elongate member 2758 (e.g., a core wire) can be movably disposed. A coupling element 2766 is coupled to a distal end portion of the first elongate member 2756, for example, by gluing a portion of the coupling element 2766 to an interior wall of the first elongate member 2756. The coupling element 2766 can be various lengths and can in some embodiments have a length, for example, of about 1-2 mm. The first elongate member 2756 can also include a marker band (not shown) coupled to a distal end portion of the first elongate member 2756.

Figure 40:
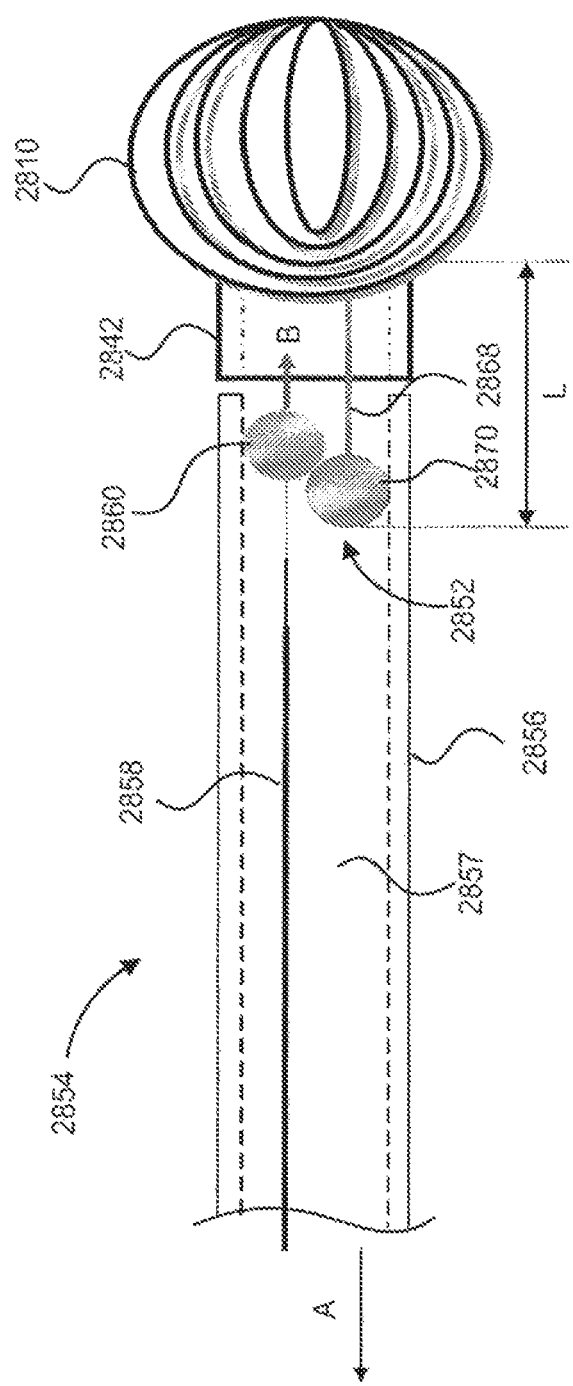
FIG. 40 is a schematic illustration of a portion of an insertion device coupled to an expandable implant, according to another embodiment.

A ball member 2760 is disposed at a distal end of the second elongate member 2758 and the second elongate member 2758 can be moved between a first position in which the ball member 2760 is disposed at a distance from the coupling element 2766 (e.g., distal of the coupling element 2766) as shown in FIG. 40 and a second position in which the ball member 2760 is disposed in contact with the coupling element 2766 at a location along a length of the coupling element 2762 such that an interference fit is created between the ball member 2760 and the coupling element 2766. The insertion device 2754 can be used to insert and deploy an implant and be detached from the implant in the same or similar manner as described above for insertion device 2654.

FIG. 40 is a schematic illustration of another embodiment of an insertion device that can be used to insert and deploy an implant, such as an expandable implant as described herein. An insertion device 2854 can be used in conjunction with a cannula and can be releasably or removably coupled to an implant, as described above for example, for insertion device 2554.

The insertion device 2854 includes a first elongate member 2856 defining a lumen 2857 through which a second elongate member 2858 can be movably disposed. The first elongate member 2856 can also include a marker band (not shown) coupled to a distal end portion of the first elongate member 2756. An insertion ball member 2860 is disposed at a distal end of the second elongate member 2858. The insertion device 2854 can be coupled to an expandable implant 2810 similar to or the same as the expandable implants described herein. The expandable implant 2810 includes a marker band 2842 and a connector member 2852 coupled to the marker band 2842. The connector member 2852 includes a wire 2868 coupled to the marker band 2842 and/or the implant 2810 and an implant ball member 2870 coupled to (or formed integrally or monolithically with) the wire 2868. The wire 2868 and implant ball member 2870 collectively can have a length L that in some embodiments can be, for example, 1.5 mm. Although not discussed in detail above, the connector members 1652, 1952, 2352, and 2452 described above for previous embodiments of an expandable implant can include the same or similar features and functions as the connector 2852.

To insert and deploy the expandable implant 2810 within a patient's body, the expandable implant 2810 is first coupled to the insertion device 2854. Specifically, the second elongate member 2858 is moved distally (in a direction of arrow B in FIG. 40) such that the insertion ball member 2860 is disposed outside a distal end of the first elongate member 2856. The implant ball member 2870 is then inserted into the distal end of the first elongate member 2856 as shown in FIG. 40. The second elongate member 2858 is then moved proximally (in the direction of arrow A in FIG. 40) such that the insertion ball member 2860 locks or traps the implant ball member 2870 within the lumen 2857 of the first elongate member 2856 as shown in FIG. 40. For example, each of the insertion ball member 2860 and the implant ball member 2870 can have a diameter greater than half the diameter of the lumen 2857 of the first elongate member 2856 such that when the implant ball member 2870 is disposed within the lumen 2857 and the insertion ball member 2860 is moved proximally into the lumen 2857, the implant ball member 2860 cannot be pulled back out of the lumen 2857.

With the implant ball member 2870 trapped within the lumen 2857 of the first elongate member 2856, the expandable implant 2810 will be held to the insertion device 2854. As described above for the previous embodiment, a locking mechanism (not shown) can be used to lock the second elongate member 2658 in this position relative to the first elongate member 2856. With the insertion device 2854 coupled to the expandable implant 2810, a distal end portion of the expandable implant 2810 can be inserted into, for example, an insertion cannula (not shown) (e.g., cannula 102 described above), and the insertion cannula can be used to insert the implant 2810 into a blood vessel in a similar manner as described above with respect to previous embodiments. After the expandable implant 2810 has been deployed, the insertion device 2854 can be detached from the expandable implant 2810 in a similar manner as described above for the previous embodiment. Specifically, to detach the insertion device 2854 from the expandable implant 2810, the second elongate member 2858 is unlocked and moved distally (in the direction of arrow B) such that the insertion ball member 2860 is moved distally outside of the first elongate member 2856, un-trapping the implant ball member 2870. The insertion device 2854 can then be removed by pulling the first elongate member 2856 and the second elongate member 2858 proximally.

Figure 41:
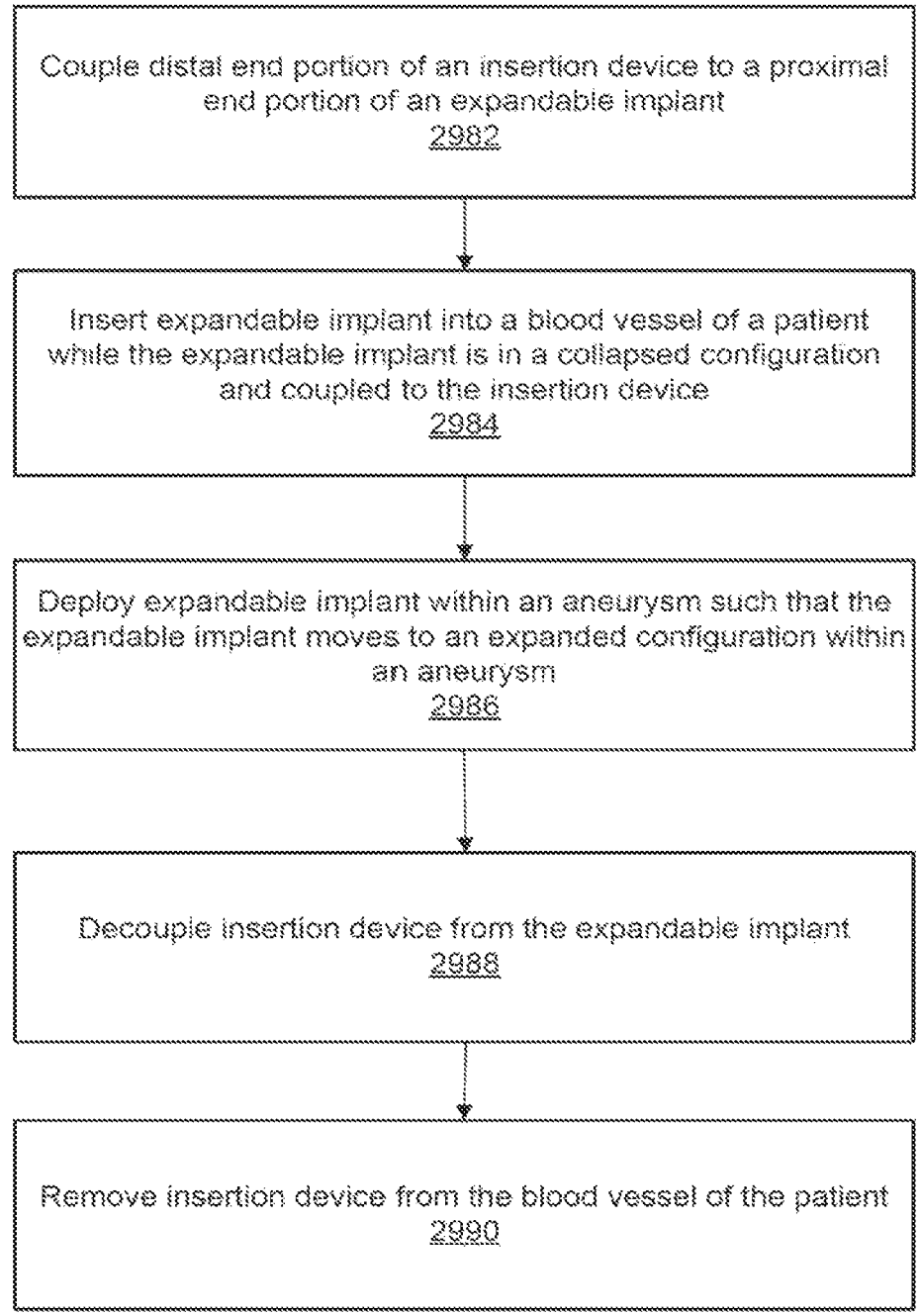
FIG. 41 is a flowchart illustrating a method of deploying an expandable implant, according to an embodiment.

FIG. 41 is a flowchart illustrating a method of deploying an expandable implant within an aneurysm using an insertion device as described herein. The method includes, at 2982, coupling a distal end portion of an insertion device to a proximal end portion of an expandable implant. For example, the insertion device can be an insertion device as described herein and the expandable implant can be an expandable implant as described herein. The insertion device can include a first elongate member that defines a lumen and a second elongate member movably disposed at least partially within the lumen of the first elongate member. The coupling can include moving the second elongate member proximally relative to the first elongate member such that a first coupling member on a distal end of the second elongate member engages a second coupling member on at least one of the first elongate member or the expandable implant and secures a portion of the expandable implant to the insertion device. In some embodiments, the second coupling member can be disposed on the first elongate member, and the moving the second elongate member proximally relative to the first elongate member causes the second coupling member to be moved from a collapsed configuration to an expanded configuration. In some embodiments, the second coupling member is disposed on the expandable implant, and prior to moving the second elongate member proximally, the second coupling member is inserted through a distal end of the first elongate member such that the second coupling member is disposed within the lumen of the first elongate member.

At 2984, the expandable implant can be inserted within a blood vessel of a patient while the expandable implant is in a collapsed configuration and coupled to the insertion device. For example, the expandable implant can be moved to a collapsed configuration using a cannula as described herein. At 2986, the expandable implant can be deployed within an aneurysm such that the expandable implant moves to an expanded configuration within the aneurysm. For example, the expandable implant can be moved outside the cannula such that it can move to its expanded configuration.

At 2988, the insertion device can be decoupled from the expandable implant, and at 2990, the insertion device can be removed from the blood vessel of the patient.

Figure 42:
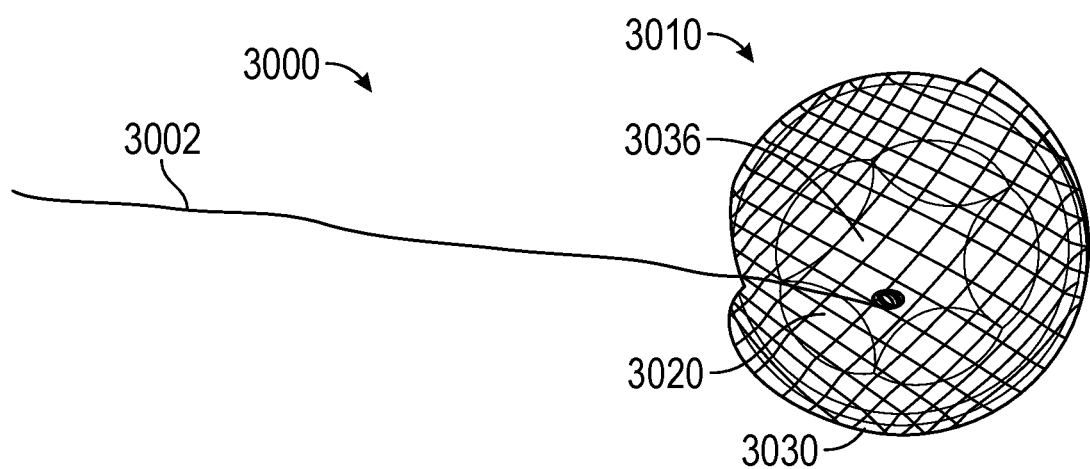
FIG. 42 is a view of a portion of a medical device in an expanded configuration, according to an embodiment.
Figure 43:
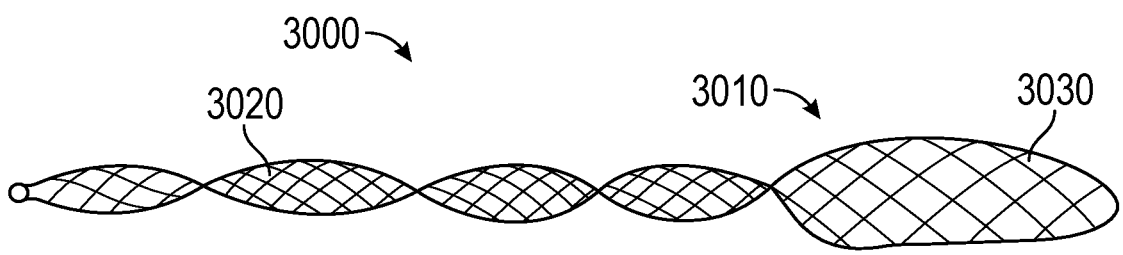
FIG. 43 is a view of a portion of the medical device of FIG. 42 in a collapsed configuration.

FIGS. 42 and 43 illustrate a portion of another embodiment of a medical device. The medical device 3000 can include the same or similar features and functions as described above for previous embodiments. For example, the medical device 3000 includes an expandable implant 3010 and an insertion portion or member 3002. The expandable implant 3010 can be moved between a collapsed configuration, as shown in FIG. 43 and an expanded configuration, as shown in FIG. 42.

The expandable implant 3010 includes a ribbon-like strand of porous mesh that includes a first portion 3020 and a second portion 3030 formed as a single component. In this embodiment, when the expandable implant 3010 is in the expanded configuration, the second portion 3030 forms a ball-like structure that defines an interior region 3036 and the first portion 3020 can be deployed within the interior region 3036. Specifically, during deployment of the medical device 3000, the second portion 3030 can be deployed first such that it can be expanded to the ball-shaped structure within an aneurysm, and then the first portion 3020 can be deployed within the interior region 3036 to substantially fill the second portion 3030 as shown in FIG. 42.

Figure 44:
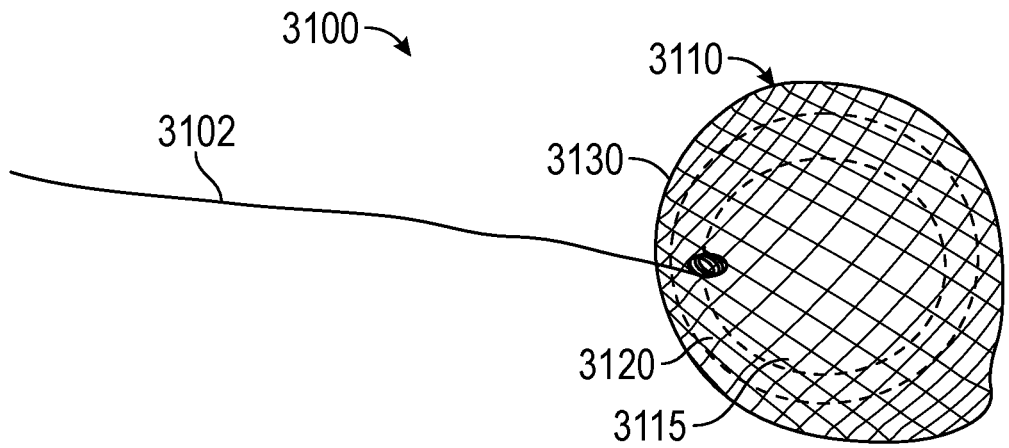
FIG. 44 is a view of a portion of a medical device in an expanded configuration, according to an embodiment.
Figure 45:
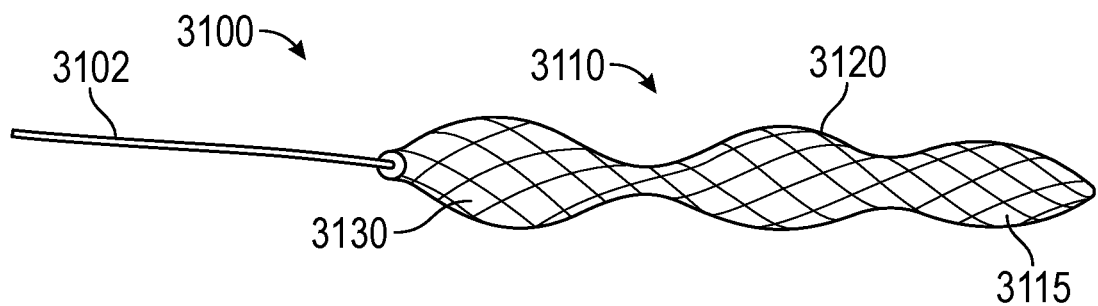
FIG. 45 is a view of a portion of the medical device of FIG. 44 in a collapsed configuration.
Figure 46:
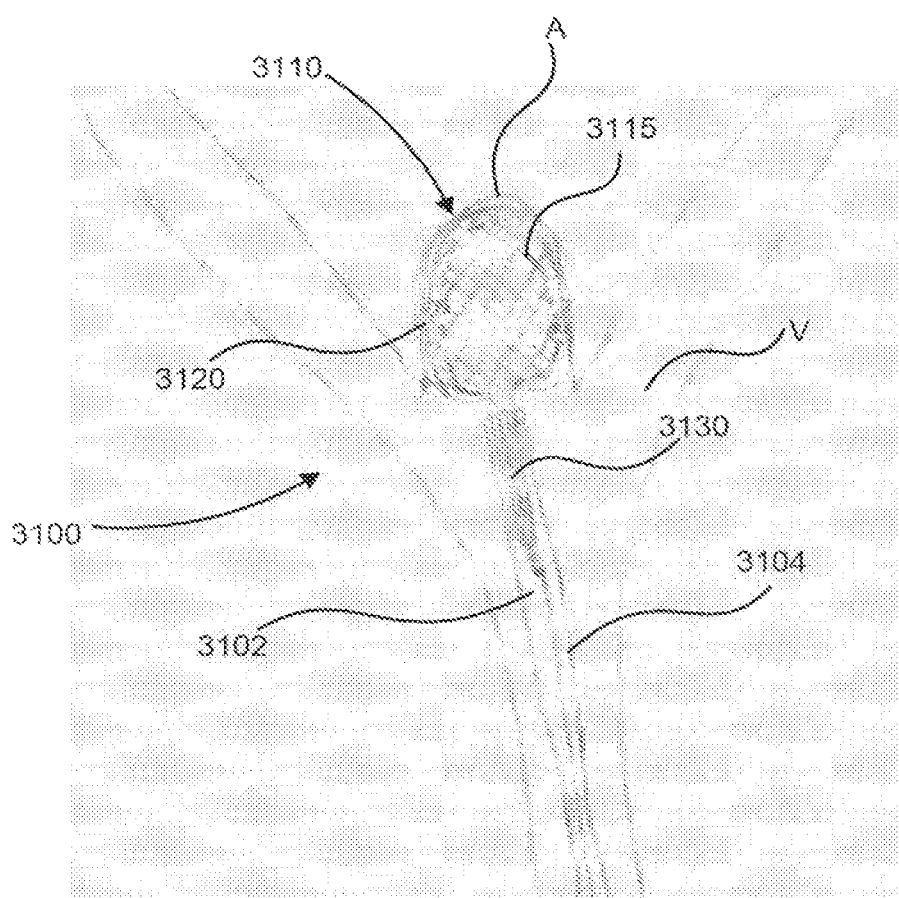
FIG. 46 is a view of a portion of the medical device of FIG. 44 shown partially deployed within an aneurysm.

FIGS. 44-46 illustrate a portion of another embodiment of a medical device. The medical device 3100 can include the same or similar features and functions as described above for previous embodiments. For example, the medical device 3100 includes an expandable implant 3110 and an insertion portion or member 3102. The expandable implant 3110 can be moved between a collapsed configuration, as shown in FIG. 45 and an expanded configuration, as shown in FIG. 44.

The expandable implant 3110 is an example of a multi-layer implant that includes a ribbon-like strand of porous mesh that includes a first portion 3130, a second portion 3120 and a third portion 3115 formed with a single mesh component. Such an embodiment may be desirable in that the implant can fit in a small delivery catheter, but can have high flow disruption by having more than two layers of material, and forming the layers in-vivo. For example, in this embodiment, when the expandable implant 3110 is in the expanded configuration, the second portion 3120 can be expanded within the third portion 3115 and the first portion 3130 can be expanded within the second portion 3120. Specifically, during deployment within an aneurysm A, as shown in FIG. 46, the medical device 3100 can first be inserted into a delivery catheter 3104 such that the expandable implant 3110 is moved to its collapsed configuration. At the deployment site, the expandable implant 3110 can be moved outside the delivery catheter 3104 and deployed within an aneurysm. During deployment, the third portion 3115 can be deployed first, then the second portion 3120 can be deployed within an interior region defined by the third portion 3115, and then the first portion 3130 can be deployed within an interior region defined by the second portion 3120. FIG. 46 illustrates the expandable implant 3110 with the third portion 3115 and the second portion 3120 deployed and the first portion 3130 still within the catheter 3104. In some embodiments, the insertion portion 3102 can be coupled to the second portion 3120, such that during detachment of the insertion portion 3102 (e.g., after the expandable implant 3110 has been deployed within an aneurysm), the detachment can occur inside the second portion to avoid any part of the implant from extending or hanging within the blood vessel V.

Figure 47:
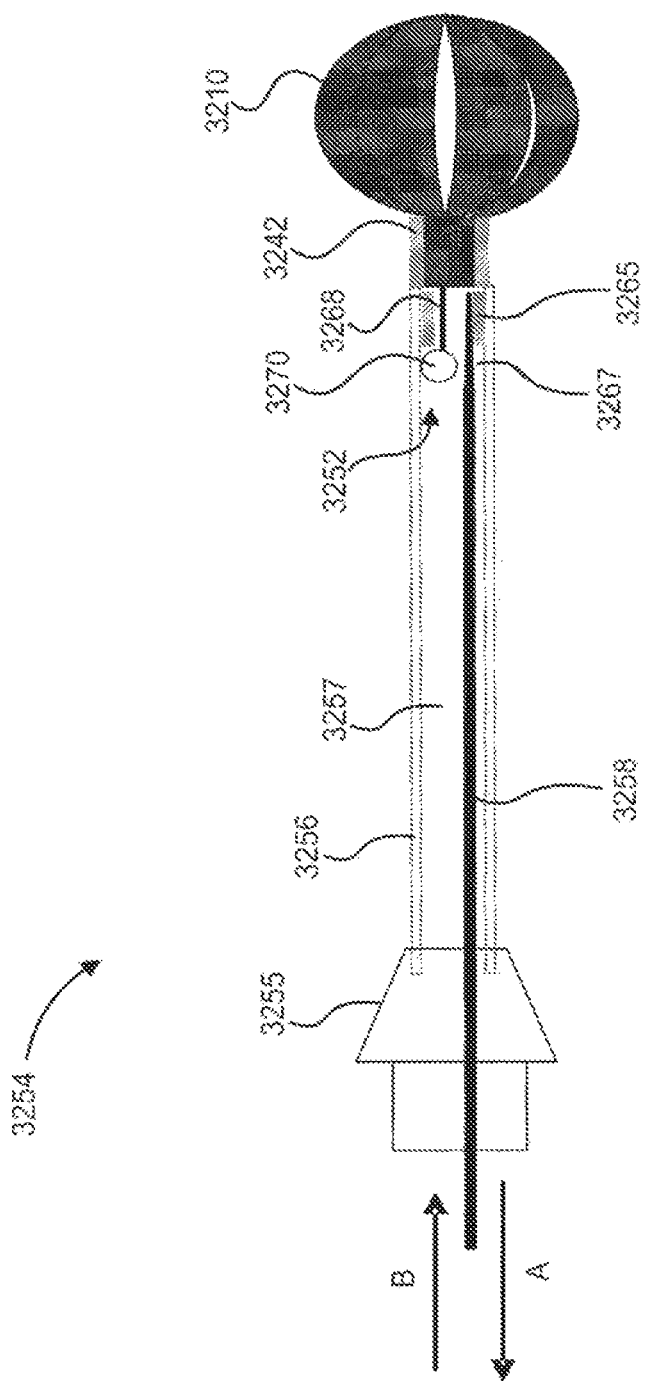
FIGS. 47-54 are each a schematic illustration of a portion of an insertion device, according to a different embodiment.

FIG. 47 is a schematic illustration of another embodiment of an insertion device that can be used to insert and deploy an implant, such as an expandable implant as described herein. An insertion device 3254 can be used in conjunction with a cannula or catheter, and can be releasably or removably coupled to an implant, as described for previous embodiments.

The insertion device 3254 includes a first elongate member 3256 defining a lumen 3257 through which a second elongate member 3258 can be movably disposed. The first elongate member 3256 includes an inner marker band 3265 coupled to a distal end portion of the first elongate member 3256. In this embodiment, a distal end portion 3267 of the second elongate member 3258 is tapered as shown in FIG. 47. The insertion device 3254 also includes a handle 3255 disposed at a proximal end portion of the insertion device 3254.

The insertion device 3254 can be coupled to an expandable implant 3210 similar to, or the same as, the expandable implants described herein. The expandable implant 3210 includes a marker band 3242 and a connector member 3252 coupled to the marker band 3242. The connector member 3252 can be similar to or the same as, for example, the connector member 2852 described above. For example, the connector member 3252 includes a wire 3268 coupled to the marker band 3242 and an implant ball member 3270 coupled to (or formed monolithically or integrally with) the wire 3268.

To insert and deploy the expandable implant 3210 within a patient's body, the expandable implant 3210 is first coupled to the insertion device 3254. Specifically, in this embodiment, the second elongate member 3258 is moved proximally (in a direction of arrow A in FIG. 47) such that the tapered distal end portion 3267 is moved proximally within the lumen 3257. This allows the implant ball member 3270 to be inserted into the lumen 3257 of the first elongate member 3256. The second elongate member 3258 is then moved distally (in the direction of arrow B in FIG. 47) such that the tapered distal end portion 3267 of the second elongate member 3256 engages the implant ball member 3270 and traps or wedges the implant ball member 3270 within the lumen 3257 of the first elongate member 3256 between the tapered distal end portion 3267 and the inner marker band 3265.

With the implant ball member 3270 locked or wedged within the lumen 3257 of the first elongate member 3256, the expandable implant 3210 will be held to the insertion device 3254. As described above for previous embodiments, a locking mechanism (not shown) coupled to the handle 3255 can be used to lock the second elongate member 3258 in this position relative to the first elongate member 3256. With the insertion device 3254 coupled to the expandable implant 3210, the expandable implant 3210 can be inserted into, for example, an insertion cannula (not shown) (e.g., cannula 102 described above) to move the expandable implant 3210 to a collapsed configuration, and the insertion cannula can be used to insert the implant into a blood vessel in a similar manner as described above with respect to previous embodiments.

After the expandable implant 3210 has been deployed within, for example, an aneurysm, the insertion device 3254 can be detached from the expandable implant 3210 and removed from the patient's body. Specifically, to detach the insertion device 3254 from the expandable implant 3210, in this embodiment, the second elongate member 3258 is unlocked from the handle 3255 and moved proximally (in the direction of arrow A) such that the tapered distal end portion 3267 is moved proximally and disengages the implant ball member 3270. With the tapered distal end portion 3267 moved proximally, the implant ball member 3260 will be free to move outside of the lumen 3257 of the first elongate member 3256. The insertion device 3254 can then be removed by pulling the insertion device 3254 proximally.

Figure 48:
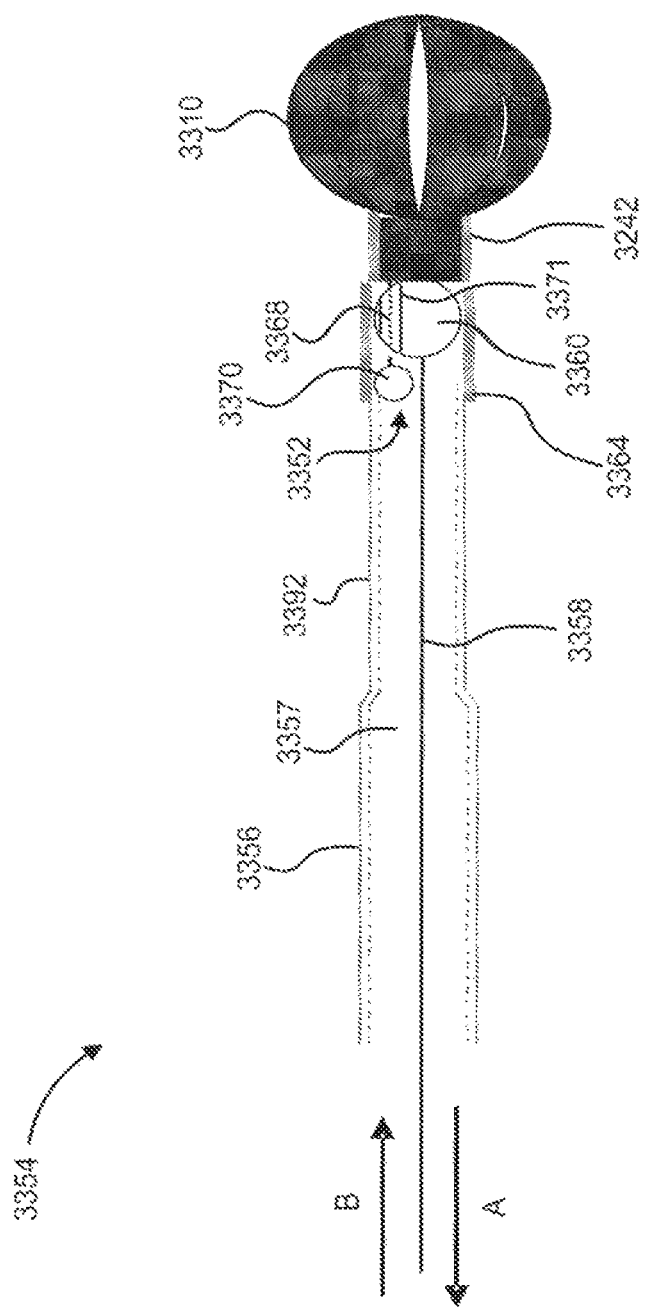

FIG. 48 is a schematic illustration of another embodiment of an insertion device that can be used to insert and deploy an implant, such as an expandable implant as described herein. An insertion device 3354 can be used in conjunction with a cannula or catheter, and can be releasably or removably coupled to an implant, as described for previous embodiments.

The insertion device 3354 includes a first elongate member 3356 defining a lumen 3357 through which a second elongate member 3358 can be movably disposed. The first elongate member 3356 includes a tapered distal end portion 3392 as shown in FIG. 48. In alternative embodiments, the first elongate member 3356 can have a constant diameter as with previous embodiments. The first elongate member 3356 also includes an outer marker band 3364 coupled to the tapered distal end portion 3392. An insertion ball member 3360 is disposed at a distal end of the second elongate member 3358 as shown in FIG. 48. The insertion device 3354 can also include a handle (not shown) disposed at a proximal end portion of the insertion device 3354 as described above for previous embodiments.

The insertion device 3354 can be coupled to an expandable implant 3310 similar to, or the same as, the expandable implants described herein. The expandable implant 3310 includes a marker band 3342 at a proximal end portion of the expandable implant 3310, and a connector member 3352 coupled to the marker band 3342. The connector member 3352 can be similar to, or the same as, for example, the connector member 2852 described above. For example, the connector member 3352 includes a wire 3368 coupled to the marker band 3342 and an implant ball member 3370 coupled to (or formed monolithically or integrally with) the wire 3368. In this embodiment, as shown in FIG. 48, the insertion ball member 3360 is larger than the implant ball member 3370 and defines a slot 3371 on a side portion thereof through which the wire 3368 of the connector member 3352 can be disposed when the implant 3310 is coupled to the insertion device 3354.

To insert and deploy the expandable implant 3310 within a patient's body, the expandable implant 3310 is first coupled to the insertion device 3354. Specifically, in this embodiment, the second elongate member 3358 is moved distally (in a direction of arrow B in FIG. 48) such that insertion ball member 3360 is moved distally outside of the lumen 3357 of the first elongate member 3356. The implant ball member 3370 can be inserted into the lumen 3357 of the first elongate member 3356 and the wire 3368 can be placed or disposed within the slot 3371 of the insertion ball member 3360. The second elongate member 3358 is then moved proximally (in the direction of arrow A in FIG. 48) such that the insertion ball member 3360 and the implant ball member 3370 are moved into the lumen 3357 of the first elongate member 3356 and the insertion ball member 3360 locks or traps the implant ball member 3370 within the lumen 3357 of the first elongate member 3356 as shown in FIG. 48.

With the implant ball member 3370 trapped within the lumen 3357 of the first elongate member 3356, the expandable implant 3310 will be coupled to the insertion device 3354. As described above for previous embodiments, a locking mechanism (not shown) coupled to the handle (not shown) can be used to lock the second elongate member 3358 in this position relative to the first elongate member 3356. With the insertion device 3354 coupled to the expandable implant 3310, the expandable implant 3310 can be inserted into, for example, an insertion cannula (not shown) to move the expandable implant 3310 to a collapsed configuration. The insertion cannula can be used to insert the implant 3310 into a blood vessel in a similar manner as described above with respect to previous embodiments.

After the expandable implant 3310 has been deployed within, for example, an aneurysm, the insertion device 3354 can be detached from the expandable implant 3310 and removed from the patient's body. Specifically, to detach the insertion device 3354 from the expandable implant 3310, in this embodiment, the second elongate member 3358 is unlocked from the handle 3355 and moved distally (in the direction of arrow B in FIG. 48) such that the insertion ball member 3360 is moved distally allowing the implant ball member 3370 to be free to be moved outside of the lumen 3357 of the first elongate member 3356. The insertion device 3354 can then be removed by pulling the insertion device 3354 proximally.

Figure 49:
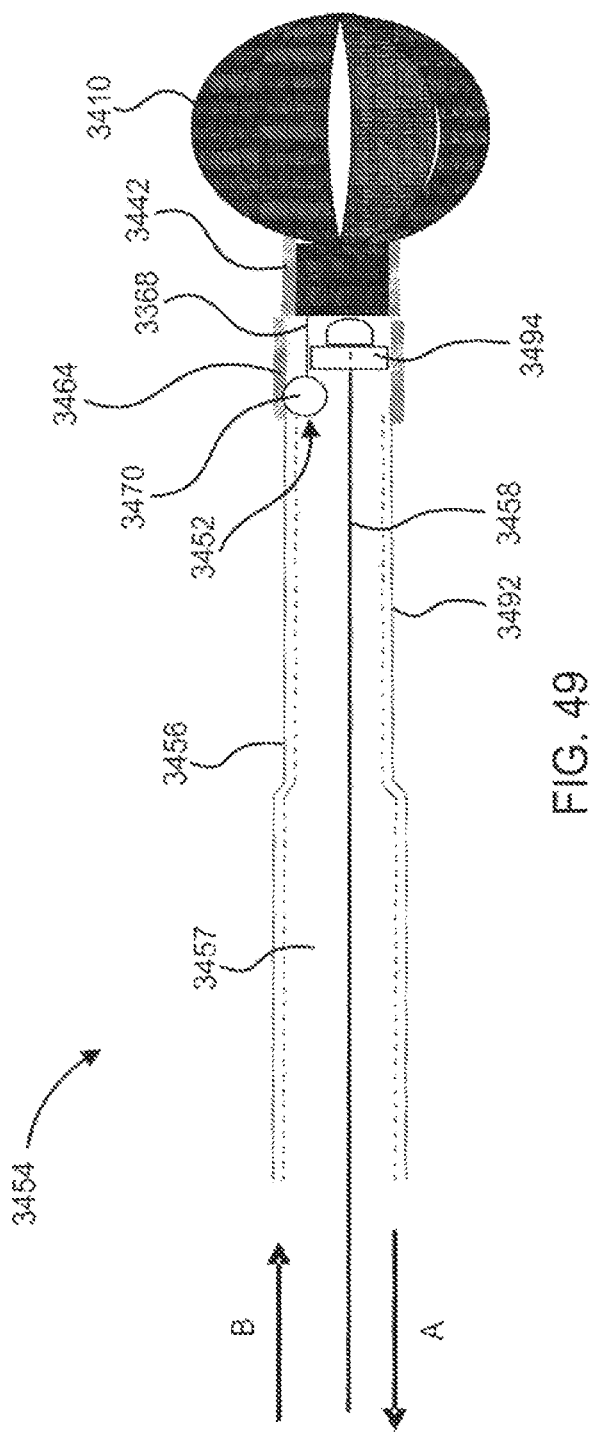

FIG. 49 is a schematic illustration of another embodiment of an insertion device that can be used to insert and deploy an implant, such as an expandable implant as described herein. An insertion device 3454 can be used in conjunction with a cannula or catheter, and can be releasably or removably coupled to an implant, as described for previous embodiments.

The insertion device 3454 includes a first elongate member 3456 defining a lumen 3457 through which a second elongate member 3458 can be movably disposed. The first elongate member 3458 includes a tapered distal end portion 3492 as shown in FIG. 49, but can in alternative embodiments have a constant diameter. The first elongate member 3456 also includes an outer marker band 3464 coupled to the tapered distal end portion 3492. A plunger or bumper member 3494 is disposed at a distal end of the second elongate member 3458, as shown in FIG. 49. The insertion device 3454 can also include a handle (not shown) disposed at a proximal end portion of the insertion device 3454 as described above for previous embodiments.

The insertion device 3454 can be coupled to an expandable implant 3410 similar to, or the same as, the expandable implants described herein. The expandable implant 3410 includes a marker band 3442 at a proximal end portion of the expandable implant 3410, and a connector member 3452 coupled to the marker band 3442. The connector member 3452 can be similar to, or the same as, for example, the connector member 2852 described above and includes a wire 3468 coupled to the marker band 3442 and an implant ball member 3470 coupled to (or formed monolithically or integrally with) the wire 3468.

To insert and deploy the expandable implant 3410 within a patient's body, the expandable implant 3410 is first coupled to the insertion device 3454. Specifically, in this embodiment, the second elongate member 3458 is moved distally (in a direction of arrow B in FIG. 49) such that insertion plunger member 3494 is moved distally outside of the lumen 3457 of the first elongate member 3456. The implant ball member 3470 can then be inserted into the lumen 3457 of the first elongate member 3456. The second elongate member 3458 is then moved distally (in the direction of arrow B in FIG. 49) such that the plunger member 3494 locks or traps the insertion ball member 3470 within the lumen 3457 of the first elongate member 3456 as shown in FIG. 49.

With the implant ball member 3470 trapped within the lumen 3457 of the first elongate member 3456, a locking mechanism (not shown) coupled to the handle (not shown) can be used to lock the second elongate member 3458 in this position relative to the first elongate member 3456. With the insertion device 3454 coupled to the expandable implant 3410, the expandable implant 3410 can be inserted into, for example, an insertion cannula (not shown) to move the expandable implant 3410 to a collapsed configuration. The insertion cannula can be used to insert the implant 3410 into a blood vessel in a similar manner as described above with respect to previous embodiments.

After the expandable implant 3410 has been deployed within, for example, an aneurysm, the insertion device 3454 can be detached from the expandable implant 3410 and removed from the patient's body. Specifically, to detach the insertion device 3454 from the expandable implant 3410, in this embodiment, the second elongate member 3458 is unlocked from the handle and moved distally (in the direction of arrow B in FIG. 49) such that the plunger member 3494 is moved distally allowing the implant ball member 3470 to be free to be moved outside of the lumen 3457 of the first elongate member 3456. The insertion device 3454 can then be removed by pulling the insertion device 3454 proximally.

Figure 50:
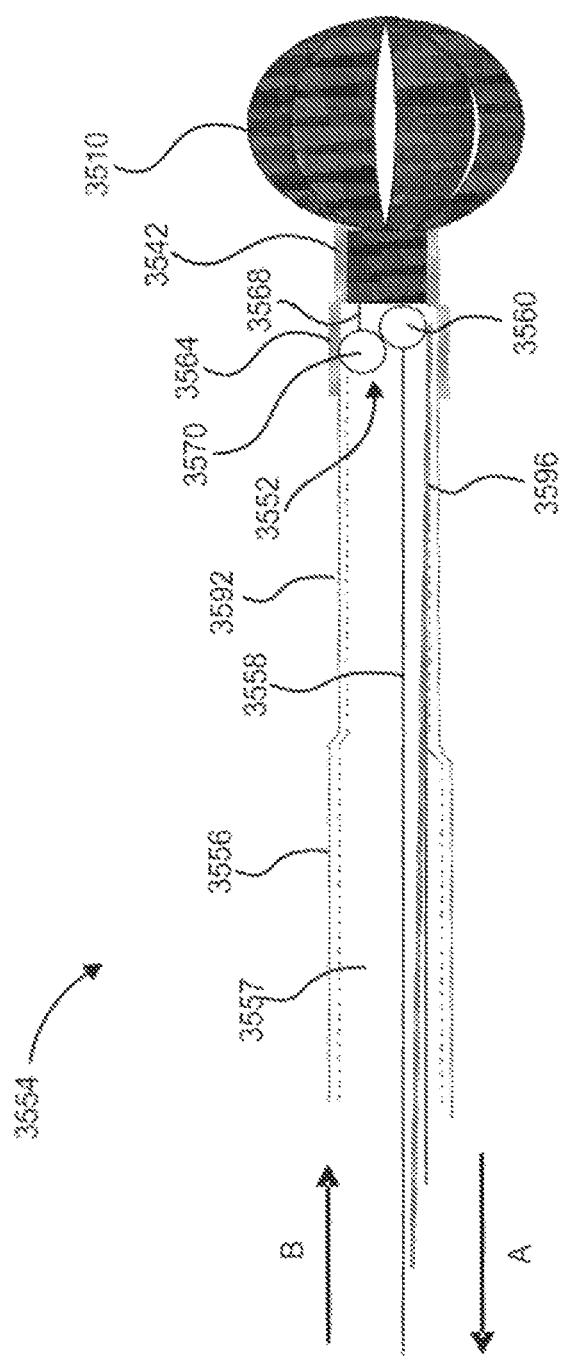

FIG. 50 is a schematic illustration of another embodiment of an insertion device that can be used to insert and deploy an implant, such as an expandable implant as described herein. An insertion device 3554 can be used in conjunction with a cannula or catheter, and can be releasably or removably coupled to an implant, as described for previous embodiments.

The insertion device 3554 includes a first elongate member 3556 defining a lumen 3557 through which a second elongate member 3558 can be movably disposed. The first elongate member 3558 includes a tapered distal end portion 3592 as shown in FIG. 50, but can in alternative embodiments, have a constant diameter. The first elongate member 3556 also includes an outer marker band 3564 coupled to the tapered distal end portion 3592. An insertion ball member 3560 is disposed at a distal end of the second elongate member 3558, as shown in FIG. 50. In this embodiment, the insertion device 3554 also includes an elongate locking member 3596. The locking member 3596 can have a constant diameter or outer perimeter along its length or can be tapered. For example a distal end portion of the locking member 3596 can have a smaller diameter than a proximal end portion of the locking member 3596. The locking member 3596 is used in conjunction with the insertion ball member 3560 to lock the implant ball member 3570 to the insertion device 3554 as described in more detail below. The insertion device 3554 can also include a handle (not shown) disposed at a proximal end portion of the insertion device 3554 as described above for previous embodiments.

As with previous embodiments, the insertion device 3554 can be coupled to an expandable implant 3510 similar to, or the same as, the expandable implants described herein. The expandable implant 3510 includes a marker band 3542 at a proximal end portion, and a connector member 3552 coupled to the marker band 3542. The connector member 3552 can be similar to, or the same as, for example, the connector members described above and includes a wire 3568 coupled to the marker band 3542 and an implant ball member 3570 coupled to (or formed monolithically or integrally with) the wire 3568.

To insert and deploy the expandable implant 3510 within a patient's body, the expandable implant 3510 is coupled to the insertion device 3554. Specifically, in this embodiment, the locking member 3596 is moved proximally (in the direction of arrow A in FIG. 50) such that a distal end portion of the locking member 3596 is disposed proximally of the insertion ball member 3560. This allows the implant ball member 3570 to be inserted into the lumen 3557 of the first elongate member 3556. In other words, the insertion ball member 3560 and the implant ball member 3570 can each be sized (e.g., each can have a diameter) such that when the locking member 3596 is moved proximally, disengaging the insertion ball member 3560, the implant ball member 3570 can be moved in and out of the lumen 3557 while the implant ball member 3570 is disposed within the lumen 3557. After the implant ball member 3570 is placed within the lumen 3557 of the first elongate member 3556, the locking member 3596 can be moved distally (in a direction of arrow B in FIG. 50) such that the distal end portion of the locking member 3596 is wedged between an inner wall of the first elongate member 3556 and the insertion ball member 3560. With the locking member 3596 in this position, the implant ball member 3570 will be held or trapped within the lumen 3557 of the first elongate member 3556 as shown in FIG. 50.

With the implant ball member 3570 trapped within the lumen 3557 of the first elongate member 3556, a locking mechanism (not shown) coupled to the handle (not shown) can be used to lock the locking member 3596 in position relative to the first elongate member 3556. With the insertion device 3554 coupled to the expandable implant 3510, the expandable implant 3510 can be inserted into, for example, an insertion cannula (not shown) to move the expandable implant 3510 to a collapsed configuration. The insertion cannula can be used to insert the implant 3510 into a blood vessel in a similar manner as described above with respect to previous embodiments.

After the expandable implant 3510 has been deployed within, for example, an aneurysm, the insertion device 3554 can be detached from the expandable implant 3510 and removed from the patient's body. Specifically, to detach the insertion device 3554 from the expandable implant 3510, in this embodiment, the locking member 3596 is unlocked from the handle and moved proximally (in the direction of arrow A in FIG. 50) such that the distal end portion of the locking member 3596 is moved proximally away from the insertion ball member 3560 allowing the implant ball member 3570 to be free to be moved outside of the lumen 3557 of the first elongate member 3556. The insertion device 3554 can then be removed by pulling the insertion device 3554 proximally.

Figure 51:
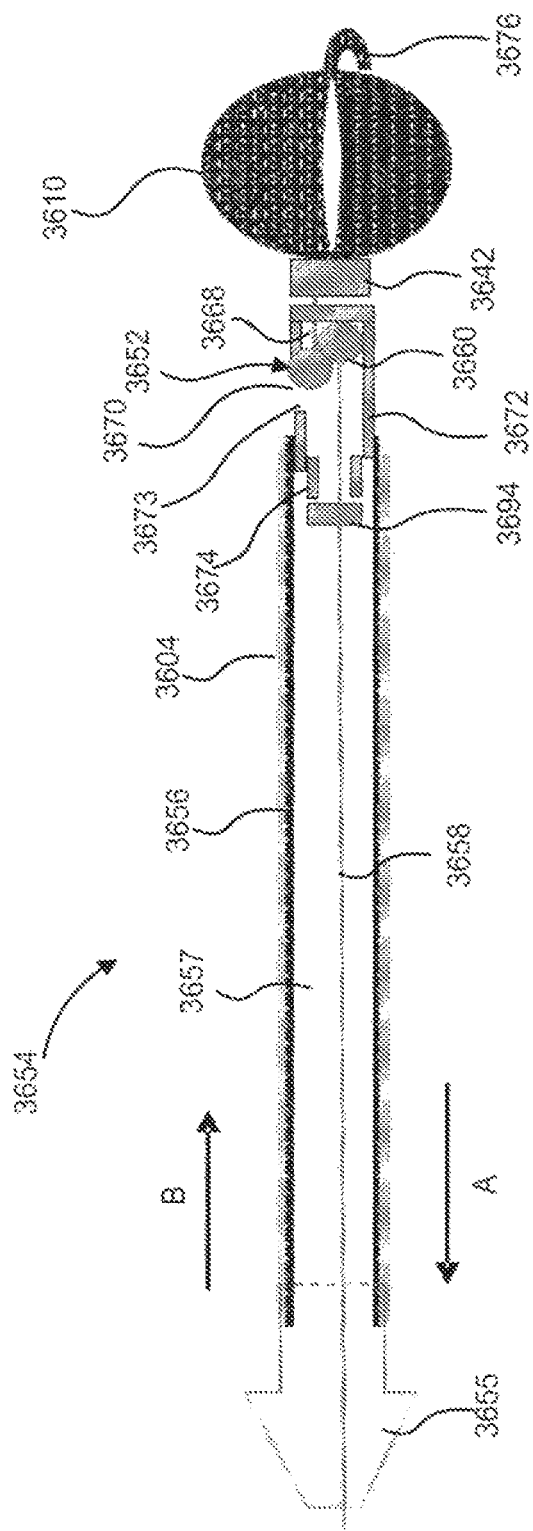

FIG. 51 is a schematic illustration of another embodiment of an insertion device that can be used to insert and deploy an implant, such as an expandable implant as described herein. An insertion device 3654 can be used in conjunction with a cannula or catheter, and can be releasably or removably coupled to an expandable implant, as described for previous embodiments.

The insertion device 3654 includes a first elongate member 3656 defining a lumen 3657 through which a second elongate member 3658 can be movably disposed. The first elongate member 3656 also includes an extension member 3672 and a stopper 3674 disposed within the lumen 3657. The extension member 3672 defines an opening or window 3673. An insertion ball member 3660 is disposed at a distal end of the second elongate member 3658 and a bumper member 3694 disposed at a spaced distance proximally of the insertion ball member 3660, as shown in FIG. 51. The insertion device 3654 can also include a handle 3655 disposed at a proximal end portion of the insertion device 3654 as described above for previous embodiments.

As with previous embodiments, the insertion device 3654 can be coupled to an expandable implant 3610 similar to, or the same as, the expandable implants described herein. In this embodiment, the expandable implant 3610 includes a marker band 3642 at a proximal end portion, and a connector member 3652 coupled to the marker band 3642. The connector member 3652 can be similar to, or the same as, for example, the connector members described above and includes a wire 3668 coupled to the marker band 3642 and an implant ball member 3670 coupled to (or formed monolithically or integrally with) the wire 3668.

The expandable implant 3610 can also include a lead-in portion 3676 (also referred to herein as "lead-in member") disposed at a distal end portion of the expandable implant 3610. The lead-in portion 3676 can be formed with, for example, a shape memory material such as nitinol, such that the lead-in portion 3676 has a biased curved shape when not constrained within, for example a cannula. The curved shape of the lead-in portion 3676 can reduce or eliminate possible sharp edges when inserting the expandable implant 3610 within a vasculature of a patient. The lead-in portion 3676 can be a separate component coupled to the expandable implant 3610 or can be formed integrally or monolithically with the expandable implant 3610. In some embodiments, the lead-in portion 3676 can be crimped to the distal end portion of the expandable implant 3610. In some embodiments, the lead-in portion 3676 can be formed integrally or monolithically with a wire member or radiopaque wire (as described for example with respect to FIGS. 23 and 24) that extends through the expandable implant 3610. For example, such a wire member can extend beyond the distal end portion of the expandable implant 3610 and form the lead-in portion 3676.

To insert and deploy the expandable implant 3610 within a patient's body, the expandable implant 3610 is coupled to the insertion device 3654. Specifically, in this embodiment, the second elongate member 3658 is moved proximally (in a direction of arrow A in FIG. 51) such that the insertion ball member 3660 is disposed proximally of the window 3673 defined in the extension member 3672. This allows the implant ball member 3670 to be inserted through an opening (not shown) defined at a distal end of the first elongate member 3656 and into the lumen 3657 of the first elongate member 3656. For example, the insertion ball member 3660 and the implant ball member 3670 can each be sized (e.g., each can have a diameter) such that collectively the insertion ball member 3660 and the implant ball member 3670 have a size (e.g., a diameter) greater than a diameter of the lumen 3657. Thus, the insertion ball member 3660 is moved to a position to provide clearance or space for the implant ball member 3670 to be inserted into the lumen 3657 and disposed near or adjacent to the window 3673. The second elongate member 3658 can then be moved distally (in a direction of arrow B in FIG. 51) such that the insertion ball member 3660 is moved distally and contacts the implant ball member 3670 and moves or pushes the implant ball member 3670 at least partially through the window 3673. The second elongate member 3658 is moved distally until the insertion ball member 3660 is moved to a position distal of the implant ball member 3670, allowing the implant ball member 3670 to move back into the lumen 3657. Further, as the second elongate member 3658 is moved distally, the bumper member 3694 on the second elongate member 3658 can contact the stopper 3674 to limit the movement of the second elongate member 3658 in the distal direction. With the insertion ball member 3660 and the implant ball member 3670 interlocked within the lumen 3657 and the implant ball member 3670 now positioned proximal of the insertion ball member 3660, the implant 3610 is maintained coupled to the insertion device 3654.

With the implant ball member 3670 held or trapped within the lumen 3657 of the first elongate member 3656, a locking mechanism (not shown) coupled to the handle 3655 can be used to lock the second elongate member 3658 in this position relative to the first elongate member 3656. With the insertion device 3654 coupled to the expandable implant 3610, the expandable implant 3610 can be inserted into the lumen of an insertion cannula 3604 to move the expandable implant 3610 to a collapsed configuration. The insertion cannula 3604 can be used to insert the implant 3610 into a blood vessel in a similar manner as described above with respect to previous embodiments.

After the expandable implant 3610 has been deployed within, for example, an aneurysm, the insertion device 3654 can be detached from the expandable implant 3610 and removed from the patient's body. Specifically, to detach the insertion device 3654 from the expandable implant 3610, the second elongate member 3558 is moved proximally such that the insertion ball member 3660 contacts the implant ball member 3670 and moves the implant ball member 3670 at least partially within the window 3673. The second elongate member 3658 is moved proximally until the insertion ball member 3660 is disposed proximal of the window 3673 such that the implant ball member 3670 can move back within the lumen 3657 of the first elongate member 3656. The stopper 3674 can limit the movement of the second elongate member 3658 by engaging the insertion ball member 3660. With the implant ball member 3670 disposed distal of the insertion ball member 3660, the implant 3610 can be released from the insertion device 3654. The insertion device 3654 can then be removed by pulling the insertion device 3654 proximally.

Figure 52:
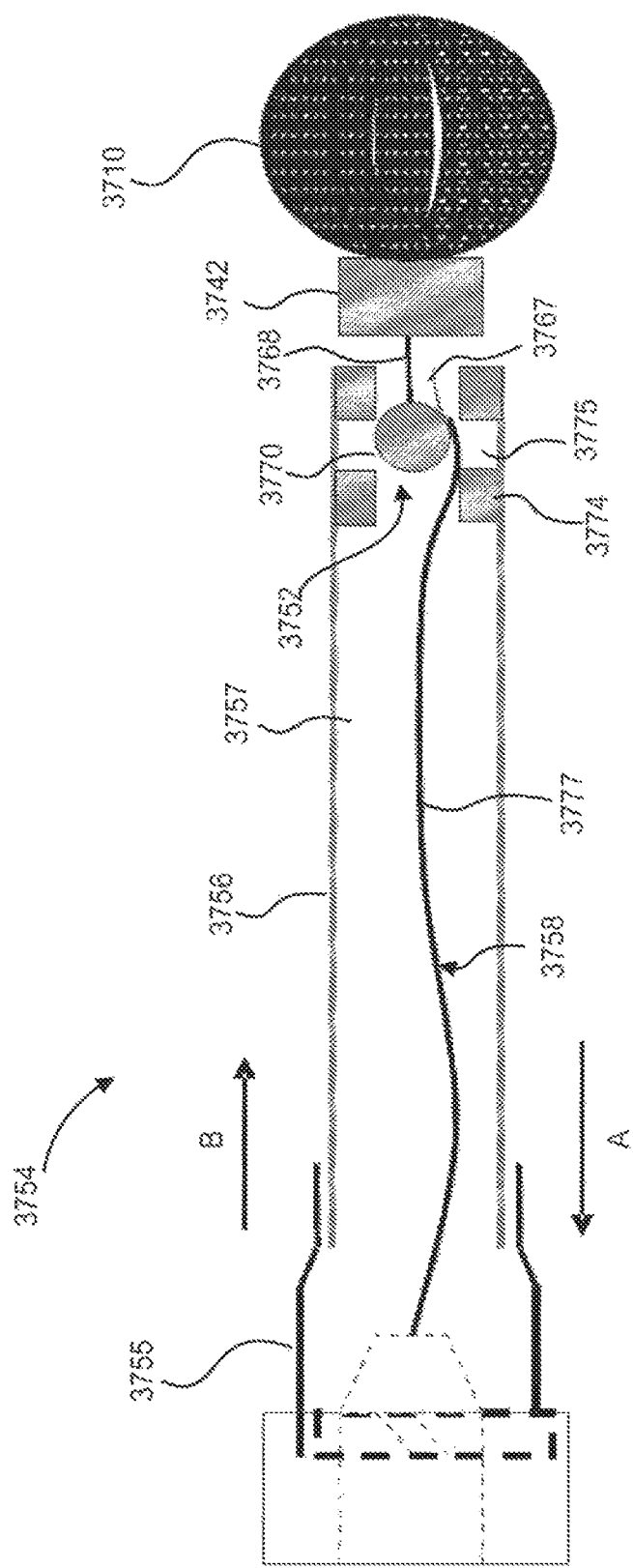

FIG. 52 is a schematic illustration of another embodiment of an insertion device that can be used to insert and deploy an implant, such as an expandable implant as described herein. An insertion device 3754 can be used in conjunction with a cannula or catheter, and can be releasably or removably coupled to an implant, as described for previous embodiments.

The insertion device 3754 includes a first elongate member 3756 defining a lumen 3757 through which a second elongate member 3758 can be movably disposed. The first elongate member 3756 includes an inner stopper 3774 coupled to a distal end portion of the first elongate member 3756 within the lumen 3757. The inner stopper 3774 defines a channel 3775 that can be used to trap or hold an implant 3710 to the insertion device 3654 as described in more detail below.

The second elongate member 3758 includes a distal end portion 3767 that can be smaller in size (e.g., diameter) than a remaining portion 3777 of the second elongate member 3758. In some embodiments, the distal end portion 3767 can be tapered. In some embodiments, the distal end portion 3767 can be a separate component coupled to the remaining portion 3777 of the second elongate member 3758. The second elongate member 3758 can be formed for example, with a shape-memory material and define a bend or bends along its length. The insertion device 3754 also includes a handle 3755 disposed at a proximal end portion of the insertion device 3754.

The insertion device 3754 can be coupled to an expandable implant 3710 similar to, or the same as, the expandable implants described herein. The expandable implant 3710 includes a marker band 3742 and a connector member 3752 coupled to the marker band 3742. The connector member 3752 can be similar to or the same as, for example, the connector members described above for previous embodiments. For example, the connector member 3752 includes a wire 3768 coupled to the marker band 3742 and an implant ball member 3770 coupled to (or formed monolithically or integrally with) the wire 3768.

To insert and deploy the expandable implant 3710 within a patient's body, the expandable implant 3710 is first coupled to the insertion device 3754. Specifically, in this embodiment, the second elongate member 3758 is moved proximally (in a direction of arrow A in FIG. 52) such that the distal end portion 3767 is moved proximally within the lumen 3757. This allows the implant ball member 3770 to be inserted into the lumen 3757 of the first elongate member 3756. The second elongate member 3758 is then moved distally (in the direction of arrow B in FIG. 52) such that the distal end portion 3767 of the second elongate member 3756 engages and urges the implant ball member 3770 at least partially within the channel 3775, trapping or wedging the implant ball member 3770 within the lumen 3757 of the first elongate member 3756 between the tapered distal end portion 3767 and the inner stopper 3774.

With the implant ball member 3770 wedged or trapped within the lumen 3757 of the first elongate member 3756, the expandable implant 3710 will be held to the insertion device 3754. As described above for previous embodiments, a locking mechanism (not shown) coupled to the handle 3755 can be used to lock the second elongate member 3758 in this position relative to the first elongate member 3756. With the insertion device 3754 coupled to the expandable implant 3710, the expandable implant 3710 can be inserted into, for example, an insertion cannula (not shown) to move the expandable implant 3710 to a collapsed configuration, and the insertion cannula can be used to insert the implant 3710 into a blood vessel in a similar manner as described above with respect to previous embodiments.

After the expandable implant 3710 has been deployed within, for example, an aneurysm, the insertion device 3754 can be detached from the expandable implant 3710 and removed from the patient's body. Specifically, to detach the insertion device 3754 from the expandable implant 3710, the second elongate member 3758 is unlocked from the handle 3755 and moved proximally (in the direction of arrow A) such that the tapered distal end portion 3767 is moved proximally and disengages the implant ball member 3770. With the tapered distal end portion 3767 moved proximally, the implant ball member 3770 will be free to move outside of the lumen 3757 of the first elongate member 3756. The insertion device 3754 can then be removed by pulling the insertion device 3754 proximally.

Figure 53:
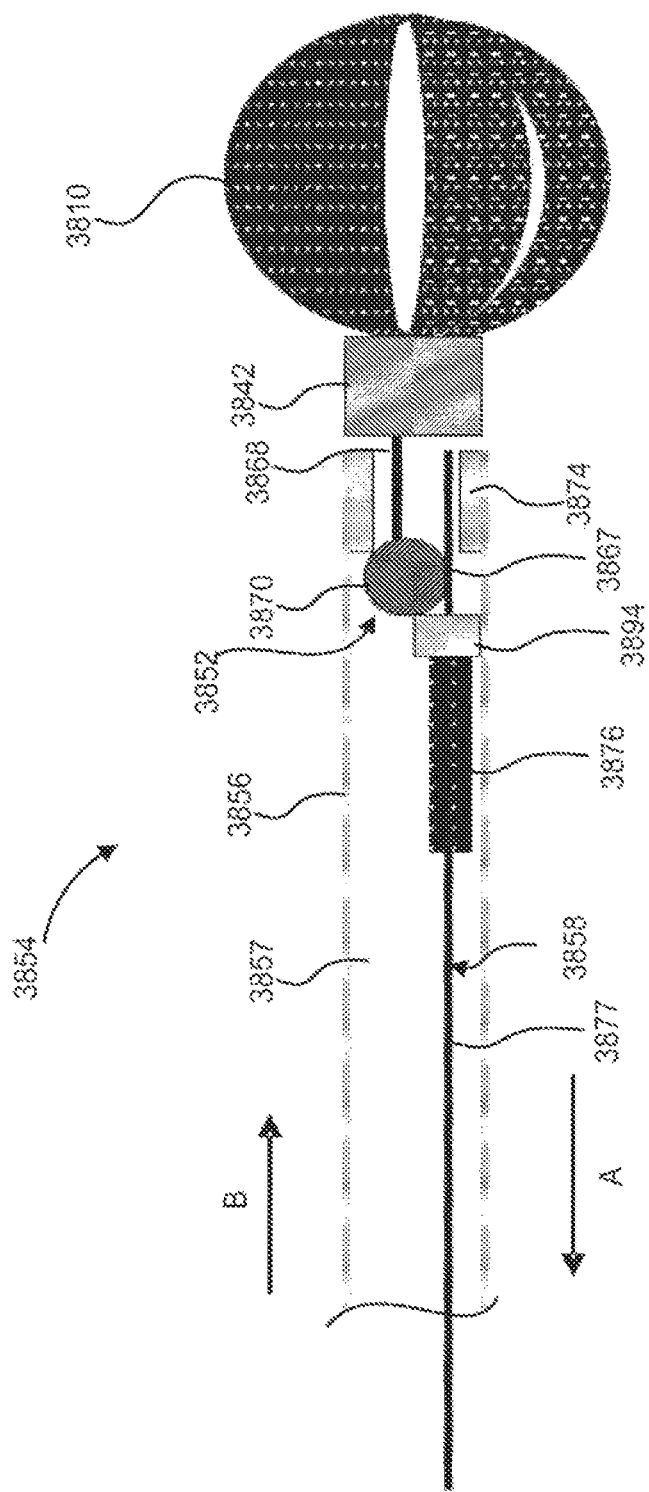

FIG. 53 is a schematic illustration of another embodiment of an insertion device that can be used to insert and deploy an implant, such as an expandable implant as described herein. An insertion device 3854 can be used in conjunction with a cannula or catheter, and can be releasably or removably coupled to an implant, as described for previous embodiments.

The insertion device 3854 includes a first elongate member 3856 defining a lumen 3857 through which a second elongate member 3858 can be movably disposed. The insertion device 3854 can also include a handle (not shown) disposed at a proximal end portion of the insertion device 3854 as described above for previous embodiments. The first elongate member 3856 includes an inner stopper 3874 coupled to a distal end portion of the first elongate member 3856. The inner stopper 3874 can be, for example, and inner marker band as described above for previous embodiments.

The second elongate member 3858 includes a distal end portion 3867 that can engage a portion of an expandable implant as described in more detail below. In some embodiments, the distal end portion 3867 can be tapered. The second elongate member 3858 also includes a bumper member 3894 and a coil member 3876. In some embodiments, the distal end portion 3867 can be a separate component coupled to the bumper member 3894. In some embodiments, the distal end portion 3867 is formed integral or monolithically with a remaining portion 3877 of the second elongate member 3858. For example, the distal end portion and/or the remaining portion 3877 can extend through a lumen (not shown) of the bumper member 3894 and a lumen (not shown) of the coil member 3876, and extend to a proximal end of the insertion device 3854.

The insertion device 3854 can be coupled to an expandable implant 3810 similar to, or the same as, the expandable implants described herein. The expandable implant 3810 includes a marker band 3842 and a connector member 3852 coupled to the marker band 3842. The connector member 3852 can be similar to or the same as, for example, the connector members described above. For example, the connector member 3852 includes a wire 3868 coupled to the marker band 3842 and an implant ball member 3870 coupled to (or formed monolithically or integrally with) the wire 3868.

To insert and deploy the expandable implant 3810 within a patient's body, the expandable implant 3810 is first coupled to the insertion device 3854. Specifically, in this embodiment, the second elongate member 3858 is moved proximally (in a direction of arrow A in FIG. 53) such that the distal end portion 3867 is moved proximally to a position proximal of the inner stopper 3874. This allows the implant ball member 3870 to be inserted through an opening in a distal end of the first elongate member 3856 and into the lumen 3857 of the first elongate member 3856. The second elongate member 3858 is then moved distally (in the direction of arrow B in FIG. 53) such that the distal end portion 3867 of the second elongate member 3856 engages the implant ball member 3870 and traps or wedges the implant ball member 3870 within the lumen 3857 of the first elongate member 3856 between the distal end portion 3867 and the inner stopper 3874.

With the implant ball member 3870 locked or wedged within the lumen 3857 of the first elongate member 3856, the expandable implant 3810 will be held to the insertion device 3854. As described above for previous embodiments, a locking mechanism (not shown) can be coupled to the handle and can be used to lock the second elongate member 3858 in this position relative to the first elongate member 3856. With the insertion device 3854 coupled to the expandable implant 3810, the expandable implant 3810 can be inserted into, for example, an insertion cannula (not shown) (e.g., cannula 102 described above) to move the expandable implant 3810 to a collapsed configuration, and the insertion cannula can be used to insert the implant 3810 into a blood vessel in a similar manner as described above with respect to previous embodiments.

After the expandable implant 3810 has been deployed within, for example, an aneurysm, the insertion device 3854 can be detached from the expandable implant 3810 and removed from the patient's body. Specifically, to detach the insertion device 3854 from the expandable implant 3810, the second elongate member 3858 is unlocked from the handle and moved proximally (in the direction of arrow A) such that the distal end portion 3867 is moved proximally and disengages the implant ball member 3870. With the distal end portion 3867 moved proximally, the implant ball member 3870 will be free to move outside of the lumen 3857 of the first elongate member 3856. The insertion device 3854 can then be removed by pulling the insertion device 3854 proximally.

Figure 54:
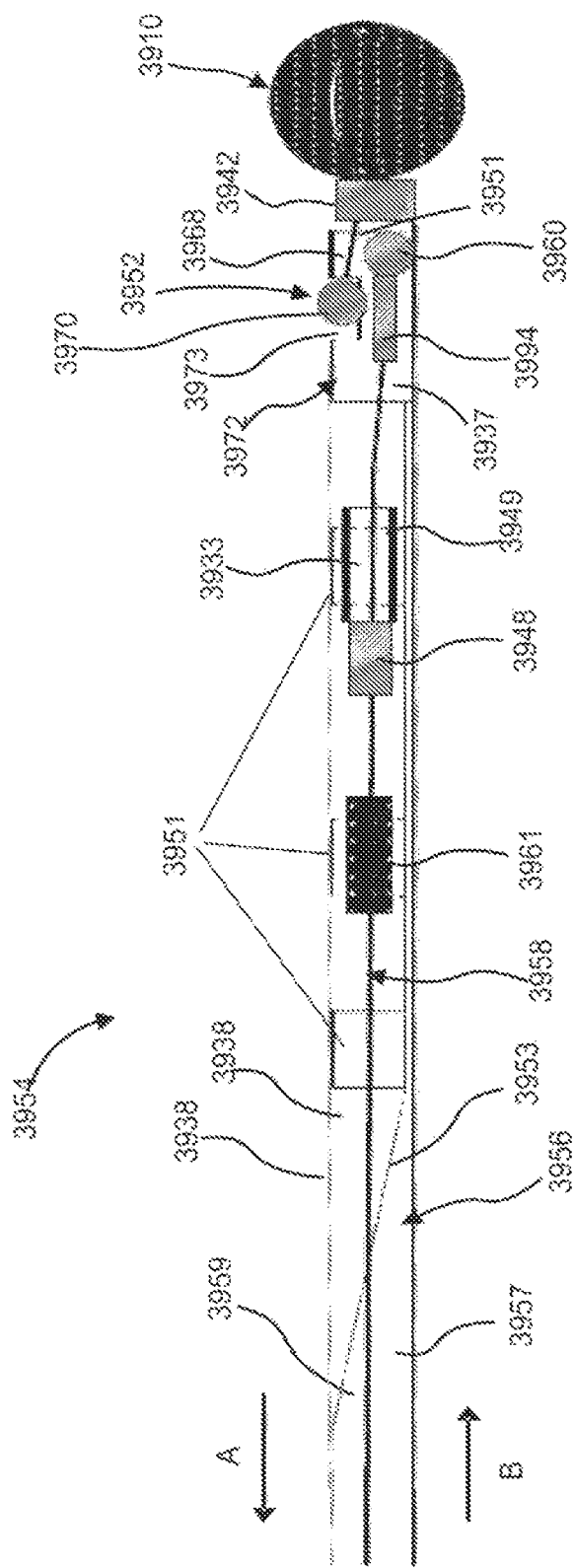

FIG. 54 is a schematic illustration of another embodiment of an insertion device that can be used to insert and deploy an implant, such as an expandable implant as described herein. An insertion device 3954 can be used in conjunction with a cannula or catheter, and can be releasably or removably coupled to an implant, as described for previous embodiments.

The insertion device 3954 includes a first elongate member 3956, a second elongate member 3958 and an outer shrink tube 3938. The first elongate member 3956 defines a lumen 3957 through which the second elongate member 3958 can be movably disposed and the shrink tube 3938 and the first elongate member 3956 collectively define a lumen 3939 that the second elongate member 3958 can also be movably disposed within.

The first elongate member 3956 defines a skived or cutout portion 3953 that extends between an intermediate portion 3959 of the first elongate member 3956 and a distal end portion 3972 of the first elongate member 3956. The outer shrink tube 3938 can be coupled to the first elongate member 3956 at least along a portion of the first elongate member 3956 that defines the skived portion 3953. The skived portion 3953 can reduce the mass of the first elongate member 3956 and allow the first elongate member 3956 to be more flexible along the skived portion. The outer shrink tube 3938 can be, for example, a material that is heat shrunk to the outer surface of the first elongate member 3956 to provide an outer boundary or perimeter of the insertion device 3954 along the skived portion 3953 of the first elongate member 3956. The outer shrink tube 3938 can be formed with a flexible material such that the portion of the first elongate member 3956 including the skived portion 3953 and the outer shrink tube 3938 is flexible and can be maneuvered through tortuous vasculature.

The distal end portion 3972 of the first elongate member 3956 defines a side window 3973 in fluid communication with a lumen 3937 defined by the distal end portion 3972. One or more tab members 3951 (three shown in FIG. 54) are disposed on the first elongate member 3956 at spaced locations along a length of the first elongate member 3956. The tab members 3951 can be, for example, semi-circular or c-shaped defining an open portion or can be circular or ring shaped forming a closed loop. The tab members 3951 can be separate components coupled to the first elongate member 3956 or formed integrally or monolithically with the first elongate member 3956. A sleeve member 3949 is coupled to one of the tab members 3951 and/or to the first elongate member 3956. The sleeve member 3949 can be, for example, welded to the tab member 3951 and/or the first elongate member 3956. The sleeve member 3949 defines a lumen 3933 through which the second elongate member 3958 can be movably disposed.

As shown in FIG. 54, the second elongate member 3958 can be movably disposed through the lumen 3957, the lumen 3939, a lumen 3933 of the sleeve member 3949 and the lumen 3937 of the distal end portion 3972. An insertion ball member 3960 is disposed at a distal end of the second elongate member 3958 and a bumper 3994 is coupled to the second elongate member 3958 proximally of the insertion ball member 3960. In addition, a stopper 3948 is coupled to the second elongate member 3958 at a spaced distance proximal of the bumper 3994 and a radiopaque marker 3961 is coupled to the second elongate member 3958 proximal of the stopper 3948. The bumper 3994, the stopper 3948 and the radiopaque marker 3961 can each be, for example, welded to the second elongate member 3958. The insertion device 3954 can also include a handle (not shown) disposed at a proximal end portion of the insertion device 3954 as described above for previous embodiments.

As with previous embodiments, the insertion device 3954 can be coupled to an expandable implant 3910 similar to, or the same as, the expandable implants described herein. In this embodiment, the expandable implant 3910 includes a marker band 3942 at a proximal end portion, and a connector member 3952 coupled to the marker band 3942. The connector member 3952 can be similar to, or the same as, for example, the connector members described above and includes a wire 3968 coupled to the marker band 3942 and an implant ball member 3970 coupled to (or formed monolithically or integrally with) the wire 3968.

In use, to insert and deploy the expandable implant 3910 within a patient's body, the expandable implant 3910 is first coupled to the insertion device 3954. Specifically, in this embodiment, the second elongate member 3958 is moved proximally (in a direction of arrow A in FIG. 54) such that the insertion ball member 3960 is disposed proximally of the window 3973 defined by the distal end portion 3972 of the first elongate member 3956. This allows the implant ball member 3970 to be inserted through an opening 3963 defined at a distal end of the first elongate member 3956 and into the lumen 3937 of the distal end portion 3972 of the first elongate member 3956. For example, the insertion ball member 3960 and the implant ball member 3970 can each be sized (e.g., each can have a diameter) such that collectively the insertion ball member 3960 and the implant ball member 3970 have a size (e.g., a diameter) greater than a diameter of the lumen 3937. Thus, the insertion ball member 3960 is moved to a position proximal of the window 3973 to provide clearance or space for the implant ball member 3970 to be inserted into the lumen 3937 and disposed near or adjacent to the window 3973. With the implant ball member 3970 disposed near the window 3973, the second elongate member 3958 can then be moved distally (in a direction of arrow B in FIG. 54) such that the insertion ball member 3960 is moved distally and contacts the implant ball member 3970, and moves or pushes the implant ball member 3970 at least partially through the window 3973. The bumper 3994 provides rigidity to the distal portion of the second elongate member 3958 as the insertion ball member 3960 is moved distally. The second elongate member 3958 is moved distally until the insertion ball member 3960 is moved to a position distal of the implant ball member 3970, allowing the implant ball member 3970 to move back at least partially within the lumen 3937. Further, as the second elongate member 3958 is moved distally, the stopper 3948 on the second elongate member 3958 can contact the sleeve member 3949 to limit the movement of the second elongate member 3958 in the distal direction. With the insertion ball member 3960 and the implant ball member 3970 interlocked within the lumen 3937 and the implant ball member 3970 now positioned proximal of the insertion ball member 3960, the implant 3910 is maintained coupled to the insertion device 3954.

With the implant ball member 3970 held or trapped within the lumen 3937 of the distal end portion 3972, a locking mechanism (not shown) can be used to lock the second elongate member 3958 in this position relative to the first elongate member 3956. For example, a locking mechanism can be coupled to a handle (not shown) as described above for previous embodiments. With the insertion device 3954 coupled to the expandable implant 3910, the expandable implant 3910 can be inserted into the lumen of an insertion cannula (not shown) to move the expandable implant 3910 to a collapsed configuration. The insertion cannula can be used to insert the implant 3910 into a blood vessel in a similar manner as described above with respect to previous embodiments.

After the expandable implant 3910 has been deployed within, for example, an aneurysm, the insertion device 3954 can be detached from the expandable implant 3910 and removed from the patient's body. Specifically, to detach the insertion device 3954 from the expandable implant 3910, the second elongate member 3958 is moved proximally (in the direction of arrow A) such that the insertion ball member 3960 contacts the implant ball member 3970 and moves the implant ball member 3970 at least partially through the window 3973. The second elongate member 3958 is moved proximally until the insertion ball member 3960 is disposed proximal of the window 3973 such that the implant ball member 3970 can move back within the lumen 3937 of the distal end portion 3972. The sleeve member 3949 can limit the proximal movement of the second elongate member 3958 by engaging the insertion ball member 3960. For example, the insertion ball member 3960 can have a larger diameter than an inner diameter of the sleeve member 3949. With the implant ball member 3970 disposed distal of the insertion ball member 3960, the implant 3910 can be released from the insertion device 3954. For example, the insertion device 3954 can be removed by pulling the insertion device 3954 proximally and as the insertion device 3954 is moved proximally, the implant ball member 3970 can move through the distal opening 3963 leaving the implant 3910 implanted within the patient's body.

Figure 55:
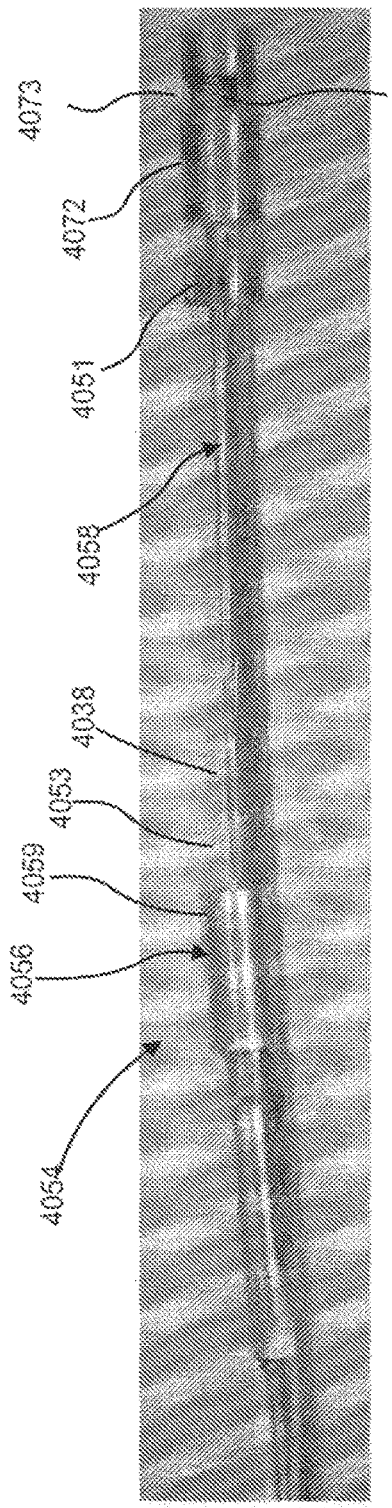
FIG. 55 is a side view of a portion of an insertion device according to an embodiment.
Figure 56:
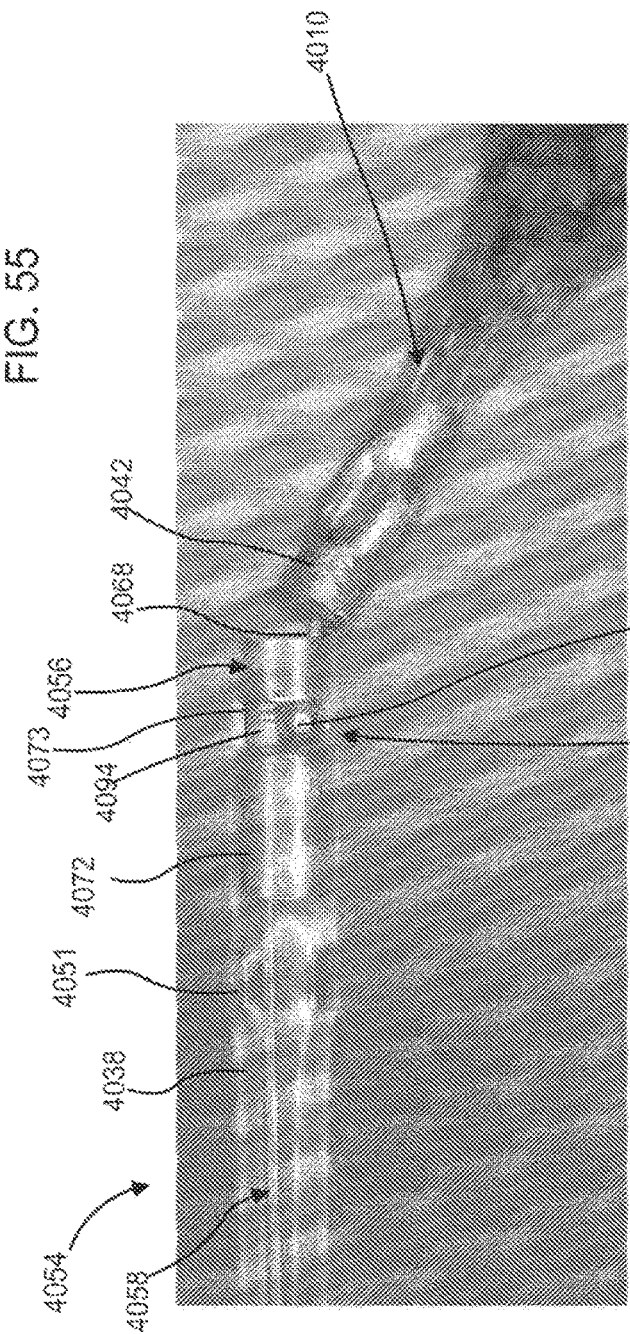
FIG. 56 is a side view of a portion of the insertion device of FIG. 55 shown coupled to an expandable implant.

FIGS. 55 and 56 illustrate another embodiment of an insertion device. An insertion device 4054 includes a first elongate member 4056, a second elongate member 4058 and an outer shrink tube 4038. The first elongate member 4056 defines a lumen (not shown) through which the second elongate member 4058 can be movably disposed and the shrink tube 4038 and the first elongate member 4056 collectively define a lumen (not shown) that the second elongate member 4058 can also be movably disposed within. The insertion device 4054 can be used in conjunction with a cannula or catheter, and can be releasably or removably coupled to an implant, as described for previous embodiments.

The first elongate member 4056 defines a skived or cutout portion 4053 that extends between an intermediate portion 4059 of the first elongate member 4056 and a distal end portion 4072 of the first elongate member 4056. The first elongate member 4056 can also include additional skived or cutout portions (not shown). The outer shrink tube 4038 can be coupled to the first elongate member 4056 at least along a portion of the first elongate member 4056 that defines the skived portion 4053. The skived portion 4053 can reduce the mass of the first elongate member 4056 and allow the first elongate member 4056 to be more flexible along the skived portion. The outer shrink tube 4038 can be, for example, a material that is heat shrunk to the outer surface of the first elongate member 4056 to provide an outer boundary or perimeter of the insertion device 4054 along the skived portion 4053 of the first elongate member 4056. The outer shrink tube 4038 can be formed with a flexible material such that the portion of the first elongate member 4056 including the skived portion 4053 and the outer shrink tune 4038 is flexible and can be maneuvered through tortuous vasculature.

The distal end portion 4072 of the first elongate member 4056 defines a side window 4073 and a lumen (not shown) in fluid communication with the side window 4073. One or more tab members 4051 (only one tab member is shown in FIGS. 55 and 56) are disposed on the first elongate member 4056 at spaced locations along a length of the first elongate member 4056. As shown in FIGS. 55 and 56, in this embodiment, the tab member 4051 is substantially c-shaped defining an open portion. The tab member 4051 can be, for example welded to the first elongate member 4056.

As shown in FIGS. 55 and 56, the second elongate member 4058 can be movably disposed through the lumen of the first elongate member 4056, the lumen defined collectively by the first elongate member 4056 and the outer shrink tube 4038, and the lumen of the distal end portion 4072. An insertion ball member (not shown) is disposed at a distal end of the second elongate member 4058 and a bumper 4094 is coupled to the second elongate member 4058 proximally of the insertion ball member. As shown in FIGS. 55 and 56, in this embodiment, the bumper 4094 includes a spring. In addition, a stopper (not shown) and a radiopaque marker (not shown) can be coupled to the second elongate member 4058 at a spaced distance proximal of the bumper 4094 as with the previous embodiments, and can provide the same function as described above for insertion device 3954. The insertion device 4054 can also include a handle (not shown) disposed at a proximal end portion of the insertion device 4054 as described above for previous embodiments. The bumper 4094, the stopper and the radiopaque marker can each be, for example, welded to the second elongate member 4058.

As with previous embodiments, the insertion device 4054 can be coupled to an expandable implant 4010 similar to, or the same as, the expandable implants described herein. The expandable implant 4010 includes a marker band 4042 at a proximal end portion, and a connector member 4052 coupled to the marker band 4042, The connector member 4052 includes a wire 4068 coupled to the marker band 4042 and an implant ball member 4070 (see FIG. 56) coupled to (or formed monolithically or integrally with) the wire 4068. FIG. 56 illustrates the implant ball member 4070 inserted into the distal end portion 4072 of the first elongate member 4056 and disposed near the window 4073.

In use, the insertion device 4054 can function the same as or similar to the insertion device 3954 described above. For example, the implant 4010 can be coupled to the insertion device 4054 and locked in position by the insertion ball member in the same or similar manner as described above for insertion device 3954. Likewise, the implant 4010 can be released from the insertion device 4054 in the same or similar manner as described above for insertion device 3954.

Figure 57:
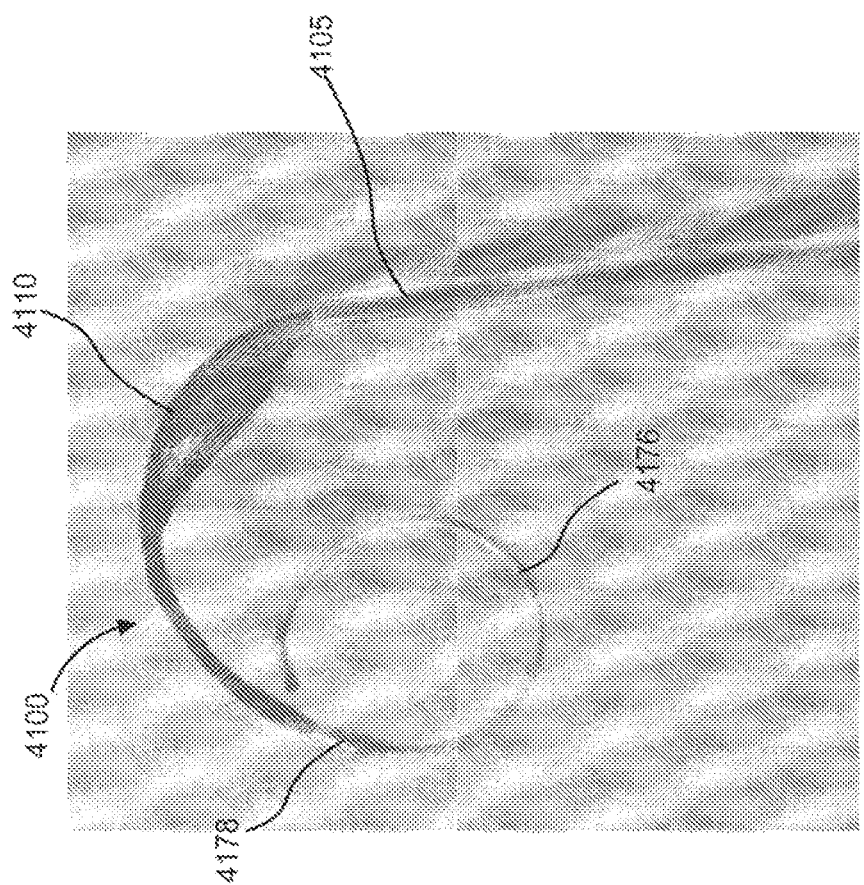
FIG. 57 is a view of a portion of a medical device, shown partially deployed, according to another embodiment.

FIG. 57 illustrates another embodiment of a medical device that includes a lead-in portion or member disposed at a distal end portion of an expandable implant. The medical device 4100 includes an expandable implant 4110 that can be configured the same as or similar to any of the embodiments of an expandable implant described herein. For example, the expandable implant 4110 can be deployed within an aneurysm of a patient as described herein. As shown in FIG. 57, a lead-in member 4176 is coupled to a distal end portion of the expandable implant 4110. In this embodiment, the lead-in member 4176 is coupled to the distal end portion of the expandable implant 4110 with a crimp 4178. The lead-in member 4176 can be formed with, for example a shape memory material such, as nitinol, such that the lead-in member 4176 has a biased curved shape when not constrained within, for example a cannula 4105. Thus, the lead-in member 4176 can provide a smooth surface free of sharp edges when inserting the expandable implant 4110 within a vasculature of a patient. The lead-in member 4176 can have a substantially linear configuration when constrained within the cannula 4105, or a delivery device as described herein. Although not shown in FIG. 57, the medical device 4100 can be delivered within a vasculature of a patient using a delivery device as described herein for other embodiments.

Figure 58:
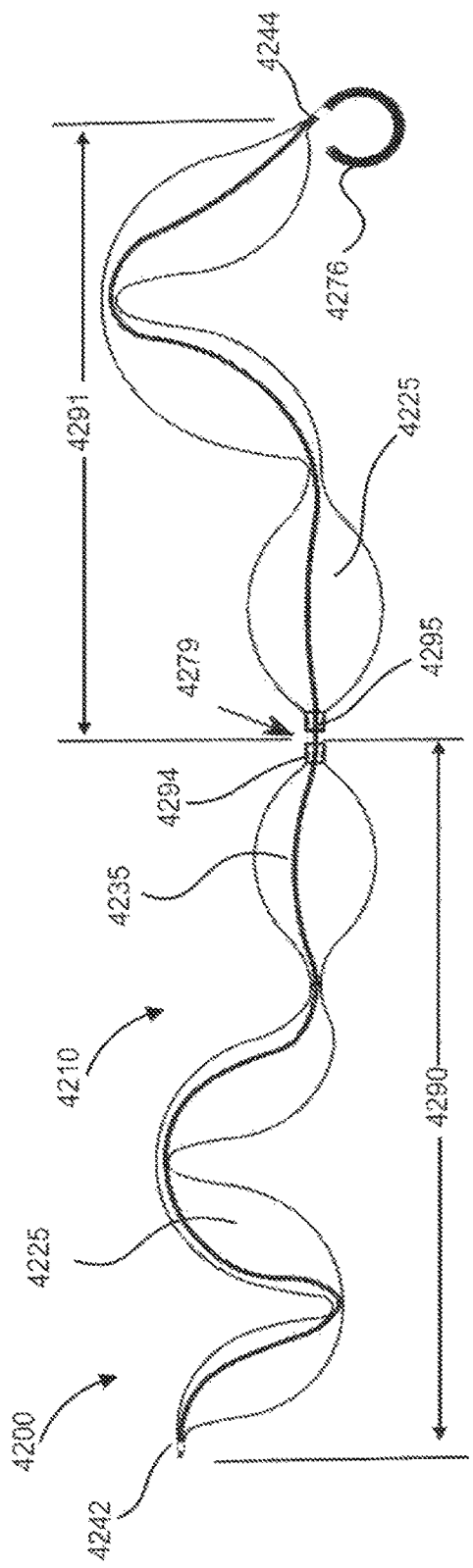
FIG. 58 is a schematic illustration of a portion of a medical device shown in a collapsed configuration, according to another embodiment.
Figure 59:
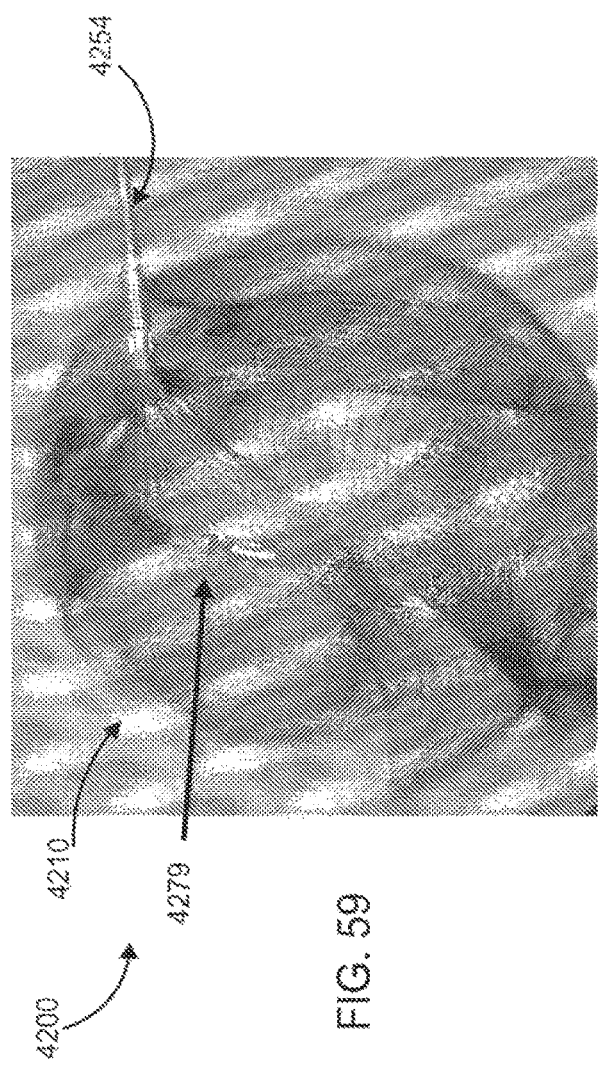
FIG. 59 is a view of the portion of the medical device of FIG. 58, shown in an expanded configuration.
Figure 60:
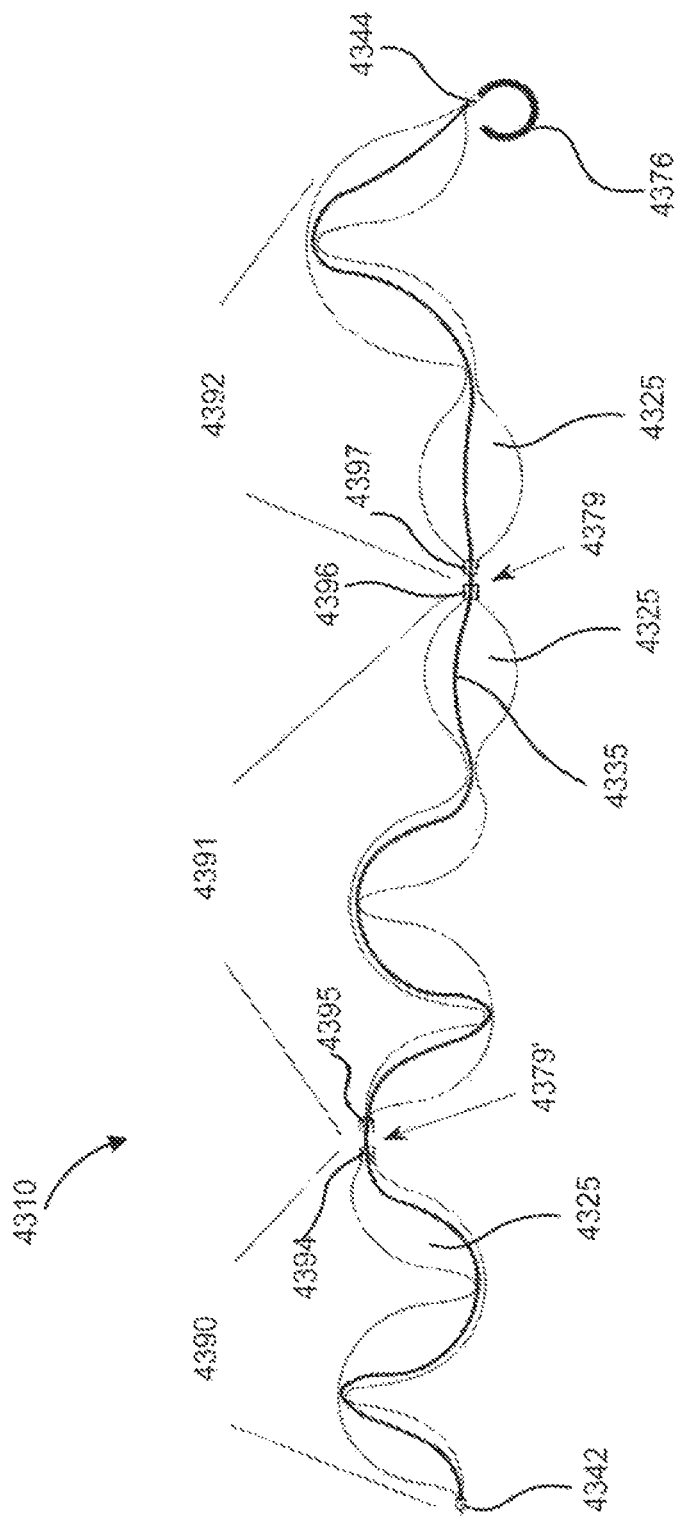
FIG. 60 is a schematic illustration of a portion of an expandable implant, according to another embodiment, shown in a collapsed configuration.

FIGS. 58-60 illustrate a portion of a medical device 4200 according to an embodiment. The medical device 4200 can include the same or similar features and functions as described herein for other embodiments. For example, the medical device 4200 can include an expandable implant 4210 configured to move from the collapsed configuration (e.g., for delivery through a blood vessel) to the expanded configuration (e.g., for deployment within an aneurysm) and an insertion member or device 4254 (shown in FIG. 59) as described herein.

Similar to the expandable implant 1810, the expandable implant 4210 includes a ribbon-like strand of porous mesh that includes one or more petal-like portions or sections 4225 along its length. In this embodiment, there are four petal-like portions 4225 included within an outer petal segment 4291 of the expandable implant 4210 and three petal-like portions 4225 included within an inner petal segment 4290 of the expandable implant 4210.

At least a portion of the porous mesh can be configured to be positioned over a neck of an aneurysm when the expandable implant 4210 is in the expanded configuration. When the expandable implant 4210 is in its expanded configuration, the expandable implant 4210 has a three-dimensional shape (e.g., a substantially spherical shape) with a substantially continuous outer surface such that a portion (e.g., edges) of at least two of the petal-like portions 4225 overlap each other as shown in FIG. 59. For example, as the expandable implant 4210 is being deployed within an aneurysm, the petal-like portions 4225 of the outer petal segment 4191 expands first and forms an outer layer that covers the aneurysm. The petal-like portions 4225 of the inner petal segment 4290 then form a second spherical layer of material inside the petal-like portions 4225 of the outer petal portion 4291 to provide greater surface area to further promote thrombosis.

In this embodiment, a suture strand 4235 extends along the length of the expandable implant 4210 to provide reinforcement to the expandable implant 4210 and can also provide for a radiopaque coil to be disposed over at least a portion of the suture strand 4235 to provide visibility of the expandable implant 4210 during, for example, fluoroscopy. As shown in FIGS. 58 and 59, the suture strand 4235 is disposed along a length of the expandable implant 4210 and across or within the petal-like portions 4225. The suture strand 4235 can be coupled to, for example, marker bands 4242 and 4244 disposed on a proximal end and a distal end, respectively, of the expandable implant 4210.

In this embodiment, the outer petal segment 4291 and the inner petal segment 4290 can be formed as separate components and coupled together by the suture strand 4235. This creates an articulation point or joint 4279 between the outer petal segment 4291 and the inner petal segment 4290. For example, the inner petal segment 4290 can include the marker band 4242 at a proximal end and a marker band 4294 at a distal end. The outer petal segment 4291 can include the marker band 4244 at a distal end and a marker band 4295 at a proximal end. The articulation joint 4279 is defined where the marker band 4294 and the marker band 4295 are coupled to the suture strand 4235.

The articulation joint 4279 can provides greater freedom of motion of the petal-like portions 4225, which can allow more uniform expansion of the petal-like portions 4225. In 4290, the separate construction of the outer petal segment 4291 and the inner petal segment 4290 can allow for one spherical layer of the expandable implant to be formed at a time, which may be advantageous and/or easier to manufacture. The ability to manufacture the expandable implant 4210 in multiple segments can also allow for the addition to, or removal of, segments of an expandable implant to provide a selected length or size of the expandable implant to meet a particular need.

As shown in FIG. 58, the expandable implant 4210 can also include a lead-in member 4276 coupled to a distal end portion of the expandable implant 4210 with the marker band 4244. The lead-in member 4276 can be formed with, for example a shape memory material such, as nitinol, such that the lead-in member 4276 has a biased curved shape when not constrained within, for example a cannula (not shown) as described above for expandable implant 4110. In some embodiments, the lead-in member 4276 can be coupled to the distal end portion of the expandable implant 4210 with a crimp similar to the implant 4110. Although not shown, the expandable implant 4210 can also include a coupling member to releasably couple the expandable implant 4210 to the delivery device 4254 as described above for previous embodiments.

FIG. 60 illustrates another embodiment of a medical device 4300 that includes an expandable implant 4310 that has multiple articulation joints 4379. The medical device 4300 can include the same or similar features and functions as described herein for other embodiments. For example, the medical device 4300 can be configured to move from a collapsed configuration a shown in FIG. 60 (e.g., for delivery through a blood vessel) to an expanded configuration (not shown) (e.g., for deployment within an aneurysm). The medical device 4300 can also include an insertion member or device (not shown in FIG. 60) to which the expandable implant 4310 can be releasably coupled, as described above for previous embodiments.

The expandable implant 4310 includes a ribbon-like strand of porous mesh that includes one or more petal-like portions or sections 4325 along its length. In this embodiment, there are three petal-like portions 4325 included within a first petal segment 4392 of the expandable implant 4310, four petal-like portions 4325 included within a second petal segment 4391, and three petal-like portions 4325 included within a third petal segment 4390 of the expandable implant 4310.

As with the previous embodiment, at least a portion of the porous mesh can be configured to be positioned over a neck of an aneurysm when the expandable implant 4310 is in the expanded configuration. When the expandable implant 4310 is in its expanded configuration, the expandable implant 4310 can have a three-dimensional shape (e.g., a substantially spherical shape) with a substantially continuous outer surface as described above for previous embodiments.

A suture strand 4335 extends along the length of the expandable implant 4310 to provide reinforcement to the expandable implant 4310 and can also provide for a radiopaque coil to be disposed over at least a portion of the suture strand 4335 to provide visibility of the expandable implant 4310 during, for example, fluoroscopy. The suture strand 4335 can be coupled to, for example, marker bands 4342 and 4344 disposed on a proximal end and a distal end, respectively, of the expandable implant 4310.

As shown in FIG. 60, the expandable implant 4310 can also include a lead-in member 4376 coupled to a distal end portion of the expandable implant 4310 with the marker band 4344. The lead-in member 4376 can be formed the same as or similar to the lead-in members described above. Although not shown, the expandable implant 4310 can also include a coupling member to releasably couple the expandable implant 4310 to a delivery device as described above for previous embodiments.

In this embodiment, the first petal segment 4392, the second petal segment 4391 and the third petal segment 4390 can be formed as separate components and coupled together by the suture strand 4335. This creates a first articulation point or joint 4379 between the first petal segment 4392 and the second petal segment 4391, and a second articulation point or joint 4379' between the second petal segment 4391 and the third petal segment 4390. In this embodiment, the first petal segment 4392 includes the marker band 4344 on a distal end and a marker band 4397 on a proximal end, the second petal segment 4391 includes a marker band 4396 on a distal end and a marker band 4395 on a proximal end, and the third petal segment 4390 includes the marker band 4342 at a proximal end and a marker band 4394 at a distal end. The first articulation joint 4379 is defined where the marker band 4397 and the marker band 4396 are coupled to the suture strand 4335, and the second articulation joint 4379' is defined where the marker band 4395 and the marker band 4394 are couple to the suture strand 4335.

As discussed above for expandable implant 4210, the articulation joints 4379, 4379' can provide greater freedom of motion of the petal-like portions 4325 of the expandable implant 4310, which can allow more uniform expansion of the petal-like portions 4325 within an aneurysm. In addition, with three petal segments 4392, 4391, 4390, the expandable implant 4310 can have a greater density when deployed within an aneurysm which can further enhance thrombosis.

In alternative embodiments, an expandable implant can have a different number of articulation joints and a different number of petal segments than described above for expandable implants 4210 and 4310. In sonic embodiments, it may be desirable to have at least two petal-like portions (e.g., 4225, 4325) between the articulation joints. In other words it may be desirable for each petal segment to have at least two petal-like portions. A greater number of articulation points or joints can provide increased freedom of motion of the petal-like portions, which can lead to a more uniform expansion of the expandable implant. The petal segments or layers can also have variable stiffness. For example, in an expandable implant, such as, expandable implant 4310, it may be desirable for the first petal segment to have a greater stiffness such that the first petal segment (e.g., petal segment 4392) can frame the aneurysm as the expandable implant is being deployed within the aneurysm. In this example it may be desirable for the second petal segment (e.g., petal layer 4391) to have a medium stiffness (e.g., stiffness less than the first petal segment and greater than the third petal segment) to fill the aneurysm, and the third petal segment (e.g., petal segment 4390) to be the softest segment to pack the aneurysm.

The petal width can also be varied between segments. For example, it may be desirable for the distal segment (e.g., first petal segment 4392) to have a greater width than the remaining segments and the proximal petal segments (e.g., the second petal segment 4391 and/or the third petal segment 4390) to be shorter and narrower to fit inside the distal segment (e.g., the first petal segment 4392).

The insertion devices (e.g., 2554, 2654, 2754, 2854, 3254, 3354, 3454, 3554, 3654, 3754, 3854, 3954, 4054) described herein can be used to deliver an expandable implant as described herein. For example, any of the expandable implants described herein can include an outer marker band and an inner marker band coupled to a proximal end portion of the expandable implant that can be used to couple the expandable implant to an insertion device, such as, for example, the insertion devices 2554, 2654 and 2754. In addition, any of the expandable implants described herein can include a connector member (e.g., 1652, 1952, 2452, 2852, 3252, 3352, 3452, 3552, 3652, 3752, 3852, 3952, 4052) as described above, including a wire and ball member configured to be coupled to an insertion device, such as, for example, insertion devices 2854, 3254, 3354, 3454, 3554, 3654, 3754, 3854, 3954 and 4054. Further, although the ball members (insertion or implant ball members) are shown as circular, any of the ball members described herein can be other shapes, such as, for example, oval, elliptical, square, rectangular, triangular or other desired shape (as shown in a side view).

The various devices described herein can be made of any material suitable for the defined purpose, including, for example, drawn filled tube DFT®. DFT is available as wire, cable or ribbon. DFT is a metal-to-metal composite developed to combine the desired physical and mechanical attributes of two or more materials into a single wire or ribbon system, which can be used for the expandable implant.

Filaments or wires for the braid or mesh (e.g., the expandable implants) can include, for example, filaments of materials such as MP35N, stainless steel, nitinol, cobalt chromium, titanium, platinum, tantalum, tungsten, or alloys thereof, or polyester, polyethylene (PET), Dacron, PEEK, vectron, and suture materials. Each strand may have a diameter between 0.0005"-0.010", e.g., about 0.002". In some embodiments, an outer material of the mesh or braid can be formed with nitinol that is superelastic at body temperature, and an inner material can be radiopaque, or alternatively platinum wires may be included in the braid to provide additional radiopacity. For example, in some embodiments, an expandable implant can include radiopaque material(s) woven within the mesh material such that the expandable implant can be highly visible without the use of a radioactive die.

Suitable materials can be chosen based on their electropositivity. For example, an expandable implant can include titanium, tungsten, or another material listed below in Table 1, or any combination thereof. In use, the electropositive material of the expanded expandable implant creates an electrically favorable region within the vascular defect and through the blood, and the region in the defect containing blood, fluid or tissue is then predisposed for endothelialization to occur.

TABLE 1

| PERIODIC TABLE ELEMENT | ABBREVIATION | FULL NAME | COMPOSITE CHARGE VALUE |
|---|---|---|---|
| 22 | Ti | titanium | 1.36 |
| 23 | V | vanadium | 1.53 |
| 40 | Zr | zirconium | 1.22 |
| 41 | Nb | niobium or columbium | 1.33 |

TABLE 1-continued

| PERIODIC TABLE ELEMENT | ABBREVIATION | FULL NAME | COMPOSITE CHARGE VALUE |
|---|---|---|---|
| 42 | Mo | molybdenum | 1.47 |
| 72 | Hf | hafnium | 1.16 |
| 73 | Ta | tantalum | 1.30 |
| 74 | W | tungsten | 1.47 |

In some embodiments, the expandable implants described herein can be formed with tubular braid, or sheets of woven filaments (forming a mesh, weave or fabric). The filaments can be wire or polymer or other suitable material. The expandable implants can be braided wire (e.g. NiTi wire), and can include a mixture of wire types and wire sizes (e.g. NiTi and Platinum wire, and e.g. 0.001" wire braided with 0.00125" wire). The expandable implants can also be made with polymer fibers, or polymer fibers and metal wire mixed together. In some embodiments, the filaments or wires for the braid or mesh can be formed with a radiopaque material. In some embodiments, the filaments or wires for the braid or mesh can include, for example, a wire coextruded with a platinum core surrounded by nitinol (NiTi). In other words, the wire includes two concentric circles when viewed in a cross-sectional view, with the center or core wire being platinum, and the outer wire being nitinol. The percentage of platinum can be, for example, between 5% platinum to 50% platinum and several variations in between (e.g., 10%, 15%, 20%, 25%, 30%, 35%, 40%, 45%). Said another way, a percentage of a diameter of the wire can be, for example 5% to 50% platinum. In some embodiments, the percentage of platinum to nitinol is 30% platinum and 70% nitinol. In some embodiments, the expandable implants can be formed with one or more bioabsorbable materials. In some embodiments, after the expandable implant is formed, the mesh of the implant can be etched to remove an outer oxide layer. This can provide corrosion reduction and/or help thrombosis form faster.

The expandable implants described herein can be formed with one or more soft pliable materials such that the expandable implant can be deployed, for example, in a ruptured or unruptured aneurysm. In some embodiments an expandable implant as described herein can be formed with one or more materials such that the expandable implant has variable stiffness. For example, a first portion of the expandable implant can be formed with a first material and a second portion of the expandable implant can be formed with a second material different than the first material, or the first material can have a different thickness than the second material. For example, in some embodiments, a distal end portion of the expandable implant can be formed with a first material and a proximal end portion of the expandable implant can be formed with a second material different than the first material. In some embodiments, a proximal end portion of an expandable implant can be formed with a first material that provides for greater stiffness than a second material with which a distal end portion of the expandable implant is formed. Such an embodiment may be desirable such that the softer distal end portion of the implant can be deployed within an aneurysm and the stiffer proximal end portion can provide more structure to help support the implant at, for example, a neck of the aneurysm.

The mesh of the expandable implants can be made by a variety of different forms, including, but not limited to, braiding, weaving, welding, or laser cutting. The mesh can have an operating length, for example, in a range of about 0.5 cm to about 70 cm. In some embodiments, the mesh can have a length of 30 cm. In some embodiments, the mesh can have a diameter in a range of about 0.5-60 mm. In some embodiments, the mesh can have a diameter of up to about 10 mm when expanded (e.g., about 9.5 mm for an outer porous member or portion, about 8 mm for an inner porous member or portion). The mesh can have a single density or can have two or more densities. For example, in some embodiments, the number of variable densities can be in a range of about 2 to about 10. For example, a first density can be about 100 PPI and a second density can be about 40 PPI (PPI=pies per inch). The braid pattern can be any pattern suitable, for example, a one-over-one configuration, or two-over-one configuration, etc. Strand count for the mesh can be in a range of about 4 strands to about 288 strands. In some embodiments, the strand count is about 48 strands. Common multiples of 4, 8, 16, 24, 32, 64, 72, 96, 128, 144, 192 and 288 strands for braid are available using commercial braiders.

A single expandable implant can include wires of the same size or a combination of 2 different wire sizes. For example, the expandable implant can have 24 wires of 0.001" and 24 wires of 0.0005". The thicker wires can impart additional strength to the expandable implant and the thinner wire can provide density. In addition, any combination of wire count, wire diameter, braid angle or pics per inch can be used to make the mesh of the expandable implant.

CONCLUSION

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. For example, the expandable implant can be inserted into the catheter concurrently with positioning of the expandable catheter adjacent the aneurysm.

The embodiments have been particularly shown and described, but it will be understood that various changes in form and details may be made. For example, although various embodiments have been described as having particular features and/or combinations of components, other embodiments are possible having any combination or subcombination of any features and/or components from any of the embodiments described herein. The specific configurations of the various components can also be varied.

For example, although the embodiments (e.g., medical device 1010) illustrated and described herein include one or two porous members or portions (e.g., porous members 1020, 1030), in other embodiments, any suitable number of porous members or portions can be included. For example, in some embodiments, the medical device 1010 can also include a third porous member (not shown) having a first end and a second end and coupled to at least one of the first porous member 1020 and the second porous member 1030. Like the first and second porous members 1020, 1030, the third porous member can have a collapsed configuration for insertion through the blood vessel and an expanded configuration for occupying the sac of the aneurysm. The third porous member can be substantially elongate and have a width in its expanded configuration that is greater than its width in its collapsed configuration.

In another example, a radiopaque marker of a medical device illustrated and described can be differently positioned on an expandable implant of the medical device. Moreover, the size and specific shape of the various components can be different than the embodiments shown, while still providing the functions as described herein.

We claim:

1. A method for treating an aneurysm, comprising:
   intravascularly delivering an expandable implant to the aneurysm, the implant comprising a first mesh and a second mesh, wherein the first mesh and the second mesh are positioned relative to one another along a length of the implant such that, when the implant is positioned within a delivery catheter during intravascular delivery of the implant, a proximal end of the first mesh is coupled to a distal end of the second mesh, wherein at least one of the first and second meshes comprises a flattened, tubular mesh;
   expanding the first mesh in the aneurysm to form a hollow globular frame within the aneurysm, the globular frame enclosing an interior cavity; and
   expanding the second mesh within the interior portion of the globular frame of the first mesh.

2. The method of claim 1, further comprising delivering a flexible, curved member to the aneurysm before positioning the first mesh.

3. The method of claim 1, wherein the second mesh is a tubular mesh.

4. The method of claim 1, wherein a proximal end of the first mesh is coupled to a distal end of the second mesh via an articulating joint.

5. The method of claim 1, wherein the first mesh is a braid.

6. The method of claim 1, wherein the second mesh is a braid.

7. The method of claim 1, wherein each of the first and second meshes is a braid.

8. The method of claim 1, wherein the first and second meshes are separate, discrete meshes.

9. The method of claim 1, wherein a proximal end of the second mesh includes a marker band.

10. The method of claim 1, wherein at least a portion of the implant is radiopaque.

11. A method for treating an aneurysm, comprising:
    intravascularly delivering an expandable implant to the aneurysm, the implant having a first mesh and a second mesh, wherein the first mesh and the second mesh are positioned relative to one another along a length of the implant such that, when the implant is positioned within a delivery catheter during intravascular delivery of the implant, an entire length of the first mesh is distal to an entire length of the second mesh, wherein at least one of the first and second meshes comprises a flattened tubular mesh;
    expanding the first mesh in the aneurysm to form a hollow frame within the aneurysm; and
    expanding the second mesh within an interior cavity defined by the frame.

12. The method of claim 11, further comprising delivering a flexible, curved member to the aneurysm before positioning the first mesh.

13. The method of claim 11, wherein the second mesh is a tubular mesh.

14. The method of claim 11, further comprising positioning a portion of the first mesh across a neck of the aneurysm.

15. The method of claim 11, wherein the first mesh is a braid.

16. The method of claim 11, wherein the second mesh is a braid.

17. The method of claim 11, wherein each of the first and second meshes is a braid.

18. The method of claim 11, wherein the first and second meshes are separate, discrete meshes.

19. The method of claim 11, wherein a proximal end of the second mesh includes a marker band.

20. The method of claim 11, wherein at least a portion of the implant is radiopaque.

* * * * *